US012808850B2

(12) United States Patent
Heindl et al.

(10) Patent No.: US 12,808,850 B2
(45) Date of Patent: Nov. 24, 2026

(54) METHOD FOR DETERMINING AT LEAST ONE ANALYTE OF INTEREST

(71) Applicant: Roche Diagnostics Operations, Inc., Indianapolis, IN (US)

(72) Inventors: Dieter Heindl, Munich (DE); Martin Rempt, Penzberg (DE); Manuel Josef Seitz, Berg (DE); Christoph Zuth, Eglfing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 570 days.

(21) Appl. No.: 18/107,996

(22) Filed: Feb. 9, 2023

(65) Prior Publication Data

US 2023/0266283 A1 Aug. 24, 2023

Related U.S. Application Data

(63) Continuation of application No. PCT/EP2021/072155, filed on Aug. 9, 2021.

(30) Foreign Application Priority Data

Aug. 10, 2020 (EP) .................................... 20190319

(51) Int. Cl.
*G01N 30/72* (2006.01)
*G01N 33/53* (2006.01)
(Continued)

(52) U.S. Cl.
CPC ......... *G01N 30/72* (2013.01); *G01N 33/5304* (2013.01); *G01N 33/54386* (2013.01);
(Continued)

(58) Field of Classification Search
CPC .. H01J 49/164; H01J 49/0418; H01J 49/0031; G01N 33/54386; G01N 2560/00; G01N 30/72
See application file for complete search history.

(56) References Cited

U.S. PATENT DOCUMENTS 12,196,767 B2 * 1/2025 Lee ........................ G01N 21/31
2004/0219531 A1 * 11/2004 DiCesare ............. H01J 49/164
435/6.13

(Continued)

FOREIGN PATENT DOCUMENTS

CN 103592361 A * 2/2014
CN 103592361 B * 9/2015

(Continued)

OTHER PUBLICATIONS

Zhao, Yaju, et al. "MoS2/Ag nanohybrid: A novel matrix with synergistic effect for small molecule drugs analysis by negative-ion matrix-assisted laser desorption/ionization time-of-flight mass spectrometry." Analytica Chimica Acta 937 (2016): 87-95 (Year: 2016).*

(Continued)

*Primary Examiner* — Wyatt A Stoffa
(74) *Attorney, Agent, or Firm* — Taft Stettinius & Hollister LLP

(57) ABSTRACT

The present invention relates to a method for determining at least one analyte of interest. The present invention further relates to a sample element, a device, a kit and the use thereof for determining at least one analyte of interest.

8 Claims, 50 Drawing Sheets

(51) Int. Cl.

| | |
|---|---|
| ***G01N 33/543*** | (2006.01) |
| ***H01J 49/16*** | (2006.01) |
| *H01J 49/00* | (2006.01) |
| *H01J 49/04* | (2006.01) |

(52) U.S. Cl.

CPC ........ *H01J 49/164* (2013.01); *G01N 2560/00* (2013.01); *H01J 49/0031* (2013.01); *H01J 49/0418* (2013.01)

(56) References Cited

U.S. PATENT DOCUMENTS

| | | | |
|---|---|---|---|
| 2016/0141166 | A1 | 5/2016 | Toriumi et al. |
| 2022/0084804 | A1 | 3/2022 | Lee et al. |

FOREIGN PATENT DOCUMENTS

| | | | |
|---|---|---|---|
| CN | 105929017 | B | 4/2018 |
| CN | 110940724 | A | 3/2020 |
| JP | 2004184137 | A | 7/2004 |
| KR | 1020200094028 | A | 8/2020 |
| WO | 200123863 | A2 | 4/2001 |
| WO | 2006118595 | A2 | 11/2006 |
| WO | 2015019861 | A1 | 2/2015 |
| WO | 2020159088 | A1 | 8/2020 |
| WO | 2022034018 | A1 | 2/2022 |

OTHER PUBLICATIONS

Kim, Young-Kwan, et al. "A layer-by-layer assembled MoS 2 thin film as an efficient platform for laser desorption/ionization mass spectrometry analysis of small molecules." Nanoscale 9.30 (2017): 10854-10860 (Year: 2017).*

Dong, Xiaoli et al.; Graphene as a Novel Matrix for the Analysis of Small Molecules by MALDI-TOF MS; Analytical Chemistry; Jul. 15, 2010; pp. 6208-6214; vol. 82, No. 14.

Kailasa, Suresh Kumar et al.; Comparison of ZnS Semiconductor Nanoparticles Capped with Various Functional Groups as the Matrix and Affinity Probes for Rapid Analysis of Cyclodextrins and Proteins in Surface-Assisted Laser Desorption/Ionization Time-of-Flight Mass Spectrometry; Analytical Chemistry; Dec. 15, 2008; pp. 9681-9688; vol. 80, No. 24.

Kim, Young-Kwan et al.; The Structural Influence of Graphene Oxide on Its Fragmentation during Laser Desorption/Ionization Mass Spectrometry for Efficient Small-Molecule Analysis; Chemistry A European Journal; 2015; pp. 7217-7223; vol. 21.

Kim, Young-Kwan et al.; A layer-by-layer assembled MoS2 thin film as an efficient platform for laser desorption/ionization mass spectrometry analysis of small molecules; Nanoscale; 2017; pp. 10854-10860; vol. 9, No. 30.

Zhao, Yaju et al.; Disposable MoS2 Arrayed MALDI MS Chip for High-Throughput and Rapid Quantification of Sulfonamides in Multiple Real Samples; ACS Sensors; 2018; pp. 806-814; vol. 3, No. 4.

Zhao, Yaju et al.; MoS2/Ag nanohybrid: A novel matrix with synergistic effect for small molecule drugs analysis by negative-ion matrix-assisted laser desorption/ionization time-of-flight mass spectrometry; Analytical Chimica Acta; 2016; pp. 87-95; vol. 937.

International Search Report; European Patent Office; International Application No. PCT/EP2021/072155; Nov. 25, 2021; 4 pages.

Written Opinion of the International Searching Authority; European Patent Office; International Application No. PCT/EP2021/072155; Nov. 25, 2021; 16 pages.

Extended European Search Report; European Patent Office; European Application No. 20190319.2; Feb. 2, 2021; 14 pages.

Zhao, Yaju et al.; Supporting Information for Disposable MoS2 Arrayed MALDI MS Chip for High-Throughput and Rapid Quantification of Sulfonamides in Multiple Real Samples; ACS Sensors; 2018; 14 pages; available at https://pubs.acs.org/doi/suppl/10.1021/acssensors.8b00051/suppl_file/se8b00051_si_001.pdf.

Kailasa, Suresh Kumar et al.; Supporting Information for Comparison of ZnS Semiconductor Nanoparticles Capped with Various Functional Groups as the Matrix and Affinity Probes for Rapid Analysis of Cyclodextrins and Proteins in Surface-Assisted Laser Desorption/Ionization Time-of-Flight Mass Spectrometry; Analytical Chemistry; Dec. 15, 2008; 11 pages; available at https://pubs.acs.org/doi/10.1021/ac8015664.

International Preliminary Report on Patentability, The International Bureau of WIPO, International Application No. PCT/EP2021/072155, Feb. 7, 2023, 17 pages.

Japanese Office Action, Japan Patent Office, Japanese Application No. 2023-509757, Feb. 25, 2025, 6 pages.

* cited by examiner

METHOD FOR DETERMINING AT LEAST ONE ANALYTE OF INTEREST

CROSS-REFERENCE TO RELATED APPLICATIONS

This application is a continuation of International PCT Application No. PCT/EP2021/072155 filed on Aug. 9, 2021, which claims priority to European Patent Application No. 20190319.2 filed on Aug. 10, 2020, the contents of each application are incorporated herein by reference in their entireties.

FIELD OF THE INVENTION

The present invention relates to a method for determining at least one analyte of interest. The present invention further relates to a sample element, a device, a kit and the use thereof for determining at least one analyte of interest.

BACKGROUND OF THE INVENTION

The SELDI (Surface enhanced laser desorption ionization) process using inorganic matrices, like $MoS_2$ or $WS_2$ after several preparation steps to address low molecular weight components has recently gained interest to be alternative to common use of organic matrices such as DHB etc.

The main problem of organic (classical) matrices are that the sample and the matrix components need to come together in liquid solution followed by drying and therefore co-crystallization. Resulting ion species of organic matrix assisted laser desorption are protonated species $[M+H]^+$. Inorganic matrices mostly give metallated species e.g. $[M+Na]^+$ which is mostly driven by only a heat transfer from matrix to the analyte and therefore no need for a co-crystallization is needed.

The prior art describes the process for the preparation of the inorganic matrix a) in which silver ions are incorporated or the substances like $MoS_2/WS_2$ are used, or b) is exfoliated using a method called Lithium intercalation or c) is exfoliated using a high boiling solvent, which can mean that the boiling solvent has a boiling point >100° C. at 1 bar.

However, these methods need manual steps and come up with an instable process and/or material, which is hard to control or solvents which are challenging to fully remove (Xu et al. ACS Sens. 2018, 3, 806-814; Xu et al. Anal. Chim. Acta 2016, 937, 87-95; Rotello et al. Nanoscale 2017, 9, 10854-10860) and CN 105929017B.).

There is thus an urgent need in the art to overcome the above mentioned problems.

It is an object of the present invention to provide a method for determining at least one analyte of interest. Further, it is an object of the present invention to provide a sample element, a device, a kit and the use thereof for determining at least one analyte of interest.

This object is or these objects are solved by the subject matter of the independent claims. Further embodiments are subjected to the dependent claims.

SUMMARY OF THE INVENTION

In the following, the present invention relates to the following aspects:

In a first aspect, the present invention relates to a method for determining at least one analyte of interest comprising the following steps:

a) Preparing a sample comprising a matrix and the at least one analyte of interest on a surface of a sample holder, b) Ionizing the at least one analyte of interest via laser irradiation having a wavelength of smaller than 400 nm, and c) Determining the analyte of interest using mass spectrometry.

The matrix comprises at least one transition metal sulfide, and wherein the transition metal sulfide is formed as particles. Preferably the transition metal sulfide is a transition metal disulfide, which is selected from the group consisting of $MoS_2$, $TiS_2$, $SnS_2$ and combinations thereof, Step a) Comprises:

Applying the sample in liquid form on the surface of a sample holder and drying the sample. Preferably, the applying step comprises (i) a combined applying of the matrix and the analyte of interest, followed by drying, or (ii) a sequentially applying of the matrix and the analyte of interest, wherein in case of the sequentially applying of the matrix and the analyte of interest, the drying is followed after each sequentially applying of the matrix and the analyte of interest.

In a second aspect, the present invention relates to the use of the method of the first aspect of the present invention for determining the at least one analyte of interest.

In a third aspect, the present invention relates to a sample element for ionizing of at least one analyte of interest via laser irradiation having a wavelength of smaller than 400 nm, wherein the sample element comprises a sample holder and a sample, wherein the sample comprises a matrix and the at least one analyte of interest, wherein the sample holder comprises an electrically conductive surface, which faces the laser irradiation, wherein the matrix and the analyte of interest are arranged on the electrically conductive surface in the beam path of the laser irradiation, wherein the matrix comprises or consists of a transition metal sulfide, preferably a transition metal disulfide, which is formed as particles having a particle size in the range of 1 nm to 6 μm.

In a fourth aspect, the present invention relates to he use of the sample element the third aspect of the present invention for determining at least one analyte of interest.

In a fifth aspect, the present invention relates to a device for determining at least one analyte of interest comprising a laser irradiation source capable of emitting laser irradiation with a wavelength of smaller than 400 nm, the sample element of the third aspect of the present invention, a mass spectrometry unit. The mass spectrometry unit is capable of determining the analyte of interest.

In a sixth aspect, the present invention relates to the use of the device of the fifth aspect of the present invention for determining at least one analyte of interest.

In a seventh aspect, the present invention relates to a kit suitable to perform a method of the first aspect of the invention comprising (A) a matrix comprising at least one transition metal sulfide, preferably at least one transition metal disulfide, which is formed as particles, (B) an organic solvent or mixtures thereof, (C) optionally at least one internal standard.

In a eight aspect, the present invention relates to the use of a kit of the seventh aspect of the invention in a method of the first aspect of the invention.

LIST OF FIGURES

DETAILED DESCRIPTION OF THE INVENTION

Figure 1A:
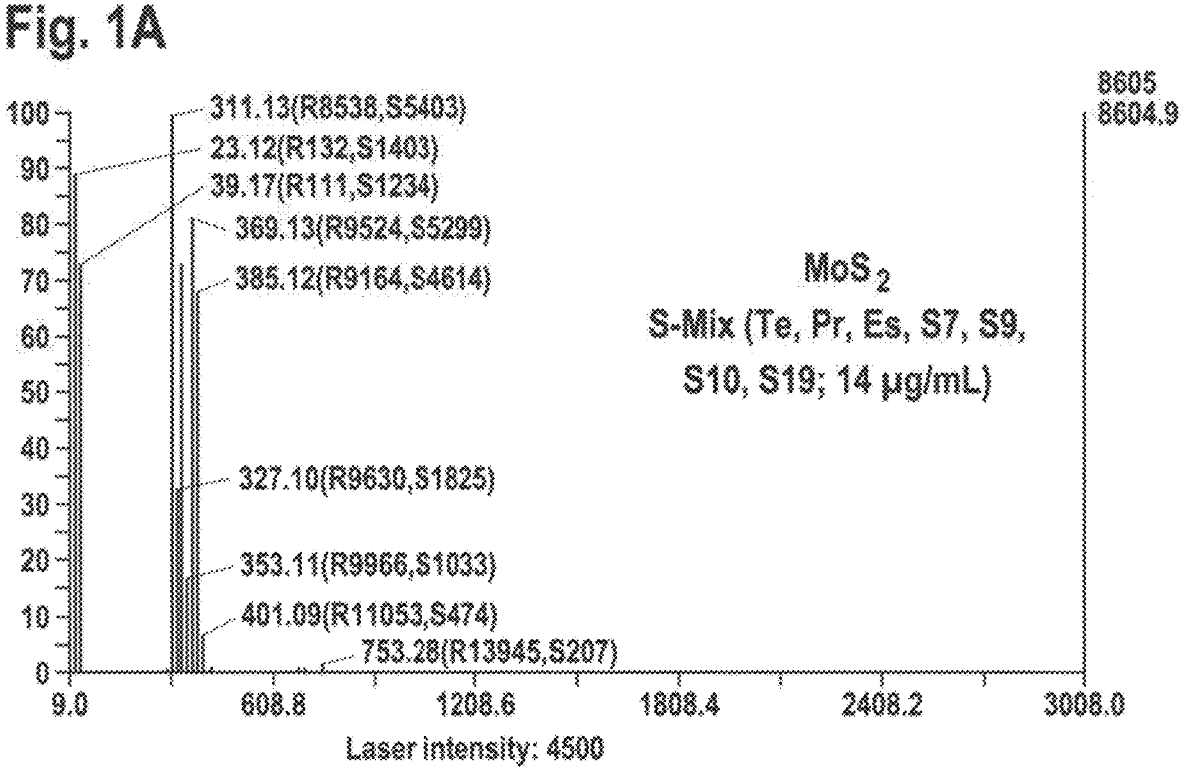
FIG. 1A to FIG. 1D show the MS spectra of a steroid mixture and therapeutically substance mixture, respectively.

Before the present invention is described in detail below, it is to be understood that this invention is not limited to the particular embodiments and examples described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

In the context of the present disclosure, the term "analyte", "analyte molecule", or "analyte(s) of interest" are used interchangeably referring the chemical species to be analysed via mass spectrometry. Chemical species suitable to be analysed via mass spectrometry, i.e. analytes, can be any kind of molecule present in a living organism, include but are not limited to nucleic acid (e.g. DNA, mRNA, miRNA, rRNA etc.), amino acids, peptides, proteins (e.g. cell surface receptor, cytosolic protein etc.), metabolite or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term "biomarker" refers to a substance within a biological system that is used as an indicator of a biological state of said system.

Analytes or an analyte of interest may be present in a biological or clinical sample. The term "biological or clinical sample" are used interchangeably herein, referring to a part or piece of a tissue, organ or individual, typically being smaller than such tissue, organ or individual, intended to represent the whole of the tissue, organ or individual. Upon analysis a biological or clinical sample provides information about the tissue status or the health or diseased status of an organ or individual. Examples of biological or clinical samples include but are not limited to fluid samples such as blood, serum, plasma, synovial fluid, spinal fluid, urine, saliva, and lymphatic fluid, or solid biological or clinical samples such as dried blood spots and tissue extracts. Further examples of biological or clinical samples are cell cultures or tissue cultures.

The term "Mass Spectrometry" ("Mass Spec" or "MS") or "mass spectrometric determination" or "mass spectrometric analysis" relates to an analytical technology used to identify compounds by their mass. MS is a methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net charge equal to one or more units. Negative ions are those having a net negative charge of one or more units, while positive ions are those having a net positive charge of one or more units. The MS method may be performed either in "negative ion mode", wherein negative ions are generated and detected, or in "positive ion mode" wherein positive ions are generated and detected.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Most sample workflows in MS further include sample preparation and/or enrichment steps, wherein e.g. the analyte(s) of interest are separated from the matrix using e.g. gas or liquid chromatography. Typically, for the mass spectrometric measurement, the following three steps are performed:

1. a sample comprising an analyte of interest is ionized. Ionization source include but are not limited to electrospray ionization (ESI), atmospheric pressure chemical ionization (APCI) and matrix-assisted laser desorption/ionization (MALDI).
2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated Ni gas may be used to improve removal of solvent. The gas-phase ionization in APCI can be more effective than ESI for analyzing less-polar entity.

"High-field asymmetric-waveform ion-mobility spectrometry (FAIMS)" is an atmospheric pressure ion mobility technique that separates gas-phase ions by their behavior in strong and weak electric fields.

"Multiple reaction mode" or "MRM" is a detection mode for a MS instrument in which a precursor ion and one or more fragment ions arc selectively detected.

Mass spectrometric determination may be combined with additional analytical methods including chromatographic methods such as gas chromatography (GC), liquid chromatography (LC), particularly HPLC, and/or ion mobility-based separation techniques. In a preferred embodiment, the mass spectrometric determination is free of additional analytical methods including chromatographic methods such as gas chromatography (GC), liquid chromatography (LC), particularly HPLC, and/or ion mobility-based separation techniques.

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), addition of hemolizing reagent (HR) to whole blood samples, and the addition of enzymatic reagents to urine samples. Also the addition of internal standards (ISTD) is considered as pre-treatment of the sample.

The term "hemolysis reagent" (HR) refers to reagents which lyse cells present in a sample, in the context of this invention hemolysis reagents in particular refer to reagents which lyse the cell present in a blood sample including but not limited to the erythrocytes present in whole blood samples. A well known hemolysis reagent is water ($H_2O$). Further examples of hemolysis reagents include but are not limited to deionized water, liquids with high osmolarity (e.g. 8M urea), ionic liquids, and different detergents.

Typically, an "internal standard" (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. $^{2}H$, $^{13}C$, or $^{15}N$ etc. label) of the analyte of interest.

In addition to the pre-treatment, the sample may also be subjected to one or more enrichment steps. In the context of the present disclosure, the term "first enrichment process" or "first enrichment workflow" refers to an enrichment process which occurs subsequent to the pre-treatment of the sample and provides a sample comprising an enriched analyte relative to the initial sample. The first enrichment workflow may comprise chemical precipitation (e.g. using acetonitrile) or the use of a solid phase. Suitable solid phases include but are not limited to Solid Phase Extraction (SPE) cartridges, and beads. Beads may be non-magnetic, magnetic, or paramagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores. The beads may be immunofunctionalized.

In the context of the present disclosure the term "second enrichment process" or "second enrichment workflow" refers to an enrichment process which occurs subsequent to the pre-treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase. In embodiments of the present invention, the method or sample element or device or kit are free of a chromatography step and chromatography unit, respectively.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a norrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC modi include hydrophilic interaction chromatography (HILIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

A "kit" is any manufacture (e.g., a package or container) comprising at least one reagent, e.g., a medicament for treatment of a disorder, or a probe for specifically detecting a biomarker gene or protein of the invention. The kit is preferably promoted, distributed, or sold as a unit for performing the method of the present invention. Typically, a kit may further comprise carrier means being compartmentalized to receive in close confinement one or more container means such as vials, tubes, and the like. In particular, each of the container means comprises one of the separate elements to be used in the method of the first aspect. Kits may further comprise one or more other reagents including but not limited to reaction catalyst. Kits may further comprise one or more other containers comprising further materials including but not limited to buffers, internal standard, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

The term "silver nanoparticles" means in the context of at least one aspect or all aspects of the present invention, that aggregates of elemental silver atoms and/or silver oxide structures are introduced intentionally on the surface by a reduction of silver ions.

The term "free of intercalated lithium" means in the context of at least one aspect or all aspects of the present invention, that the sample, in particular the matrix does not comprise lithium, which is included or inserted in the sample, in particular the matrix, by a chemical intercalation process.

The term "free of a lithium mediated exfoliation step" means in the context of at least one aspect or all aspects of the present invention, that lithium intercalated bulk material is not used in the ultrasonic exfoliation process. A lithium intercalated bulk material comprises or consists of unexfoliated multilayers in numbers of at least 10 layers with lithium atoms intercalated in between.

The term "free of a sodium hydroxide assisted exfoliation step" means in the context of at least one aspect or all aspects of the present invention, that the exfoliation step does not comprise sodium hydroxide with a pH>8 together with a high boiling solvent (boiling point >100° C. at 1 bar), e.g. N-methyl-2-pyrrolidone (NMP).

The term "free of a porous nanostructuring step" means in the context of at least one aspect or all aspects of the present invention, that no chemical or electrochemical etching process is applied to increase the porosity or the number of defects on the corresponding surface.

The term "bulk material" means in the context of at least one aspect or all aspects of the present invention, that the transition metal sulfide material, preferably the transition metal disulfide, comprises or consists of multilayers with particle sizes from the respective middle point of larger than 20 nm in all directions.

The term "single spot" means in the context at least one aspect or of all aspects of the present invention, that a predefined volume, e.g. 0.7 μL, of the corresponding suspension or solution is applied onto the surface at once.

The term "dried-droplet method" means in the context of at least one aspect or all aspects of the present invention, that the applied single droplet is dried either by atmospheric conditions or in vacuum.

The term "liquid form" can mean in the context of at least one aspect or all aspects of the present invention, that either the matrix suspension or analyte solution are solubilized in water or organic solvents or combinations thereof. Preferably, the sample is in liquid form at the operating temperature.

The term "applying" means in the context of at least one aspect or all aspects of the present invention, that the liquid sample form is located on the surface, e.g via a pipetting workflow. A pipetting workflow might be carried out with the following steps: 1) Filling the pipette with either matrix suspension or analyte solution, 2) locating the position on the surface of the sample holder and 3) releasing the desired volume of liquid on the surface of the sample holder.

The term "drying" means in the context of at least one aspect or all aspects of the present invention, that the applied liquid is evaporated to dryness either, e.g. by atmospheric conditions or e.g. in vacuum.

The term "electrically conductive surface" means in the context of at least one aspect or all aspects of the present invention, that the corresponding material has a sheet resistance smaller than or equal to 100 Ω/sq, preferably smaller than or equal to 60 Ω/sq. For example, 1 mm thick copper tape with about 17 μΩ/sq, 1 mm thick aluminium tape with about 28 μΩ/sq, or a 300 Å thick ITO coating on glass with about 60 Ω/sq can be used as the corresponding material.

The term "direct ionization" means in the context of at least one aspect or all aspects of the present invention, that only a desorption of the corresponding ions occurs, but no further adduct formation.

The term "MALDI" can mean in the context of at least one aspect or all aspects of the present invention, that with the support of a matrix or coated surface, the ultraviolet laser light gets absorbed and the resulting heat energy gets transferred from the matrix to the analyte(s), leading therefore to a desorption and ionization of the analyte(s).

The term "MALDI-TOF measurements in a positive mode" means in the context of at least one aspect or all aspects of the present invention, that the mass spectrometer is operated in the positive ionization mode. The positive ionization mode is known for a skilled person and thus is not explained in detail.

The term "laser irradiation" means in the context of at least one aspect or all aspects of the present invention, that a focused beam of monochromatic light is utilized, preferably with a pulse frequency larger than 1 Hz.

Embodiments

In a first aspect, the present invention relates to a method for determining at least one analyte of interest comprising the following steps:

a) Preparing a sample comprising a matrix and the at least one analyte of interest on a surface of a sample holder,
b) Ionizing the at least one analyte of interest via laser irradiation having a wavelength of smaller than 400 nm, and
c) Determining the analyte of interest using mass spectrometry.

The matrix comprises at least one transition metal sulfide, preferably at least one transition metal disulfide, and the transition metal sulfide is formed as particles. Preferably the transition metal sulfide or the transition metal disulfide is selected from the group consisting of $MoS_2$, $TiS_2$, $SnS_2$ and combinations thereof, More preferably, the transition metal sulfide or the transition metal disulfide is $MoS_2$. Step a) comprises:

Applying the sample in liquid form on the surface of a sample holder and drying the sample. Preferably, the applying comprises (i) a combined applying of the matrix and the analyte of interest, followed by drying, or
(ii) a sequentially applying of the matrix and the analyte of interest, wherein in case of the sequentially applying of the matrix and the analyte of interest, the drying is followed after each sequentially applying of the matrix and the analyte of interest.

The inventors surprisingly found that subject matters of the present invention, in particular the method according to the first aspect of the invention, show a simple and robust way to overcome the above-mentioned disadvantages.

The said method is suitable to enhance certain metal adducts ($Na^+$, $K^+$, $Rb^+$, $Cs^+$) to the analyte molecule to get the analyte as a moiety.

A further enhancement to stabilize a certain metal adduct by addition of crown-ethers can be observed.

The said method is capable to detect alkali ions and possible also earth-alkali ions by direct ionization, e.g. $Na^+$, $K^+$, $Rb^+$, $Cs^+$, $Mg^{2+}$, $Ca^{2+}$, $Sr^{2+}$, $Ba^{2+}$ etc.

The said method aims to make a matrix assisted laser desorption process capable to measure low molecular weight analytes with pre-coated consumables using a very easy process of production therefore.

The said method presents the utilization of bulk material, e.g. based upon $MoS_2$ or $WS_2$ or $TiS_2$ or $SnS_2$ after dissolution in an organic solvent and direct application as well as a method of using sonication process step to come up with a high concentrated suspension of the inorganic material.

The inventors could shown that for the usability of the inorganic matrices like $MoS_2$ or $WS_2$ or $TiS_2$ or $SnS_2$, no further silver intercalation or lithium mediated exfoliation nor porous nanostructuring (directed) is needed as described in the prior art. The only sample processing step a) of preparing the sample, e.g. of pipetting and air or vacuum drying is necessary to gain a sufficient MS Signal after laser irradiation.

In embodiments of the first aspect of the invention, the method or sample is free of silver nanoparticles.

In embodiments of the first aspect of the invention, the method or sample is free of intercalated lithium. In particular, the matrix is free of intercalated lithium.

In embodiments of the first aspect of the invention, the method or sample is free of a lithium mediated exfoliation step. In particular, the matrix is free of a lithium mediated exfoliation step.

In embodiments of the first aspect of the invention, the method or sample is free of a sodium hydroxide assisted exfoliation step. In particular, the matrix is free of a sodium hydroxide assisted exfoliation step.

In embodiments of the first aspect of the invention, the method or sample is free of a porous nanostructuring step. In particular, the matrix which is free of a porous nanostructuring step.

According to step a), the sample is prepared on a surface of a sample holder. The sample comprises a matrix and the at least one analyte of interest or more than one analyte, e.g. 2 or 3 or 4 or 5 or 6 or 7 or 8 or 9 or 10 or 11 or 12 or 13 or 14 or 15. The sample preparation step a) comprises at least one applying step and at least one drying step. The sample in a liquid form is applied on the surface of the sample holder. The sample is dried, preferably after the at least one applying step is performed.

The applying of the sample in liquid form can be a combined applying of the matrix and the analyte of interest, followed by drying. For example, the matrix and the analyte of interest are mixed, then applied on the surface of the sample holder and then dried, wherein preferably one layer structure comprising matrix and analyte of interest is formed.

Alternatively, the applying is a sequentially applying of the matrix and the analyte of interest, wherein in case of the sequentially applying of the matrix and the analyte of interest, the drying is followed after each sequentially applying of the matrix and the analyte of interest. For example, the matrix is applied, then dried for forming a first layer, and then the analyte of interest is applied, then dried for forming a second layer. The first and second layers can form a layer structure. Alternatively, the analyte of interest is applied, then dried for forming a first layer, and then the matrix is applied, then dried for forming a second layer. The first and second layers can form a layer structure.

The matrix comprises at least one transition metal sulfide, preferably at least one transition metal disulfide, wherein the transition metal sulfide is formed as particles.

In embodiments of the first aspect of the invention, the matrix is applied on the surface of the sample holder, then dried. After applying and drying of the matrix, the analyte of interest or a mixture of analytes is applied on the surface of the sample holder, in particular directly on the matrix, and then dried. In particular, an at least two layer structure comprising a matrix layer and an analyte layer is formed, wherein the matrix layer is directly arranged on the surface of the sample holder and between the surface of the sample holder and the analyte layer. Additionally more than two layer can form the layer structure. For example, at least two matrix layers and at least two analyte layers form the layer structure or at least one matrix layer and at least two analyte layers form the layer structure or at least two matrix layers and at least one analyte layer form the layer structure.

In embodiments of the first aspect of the invention, the matrix is dissolved in an organic solvent and sonicated to form a suspension of transition metal sulfide particles, preferably transition metal disulfide particles. In particular, the transition metal sulfide particles, preferably the transition metal disulfide particles, have a particle in the range of 1 nm to 7 μm, preferably 50 nm to 150 nm, more preferably 80 nm to 130 nm.

In embodiments of the first aspect of the invention, the transition metal sulfide particles are transition metal disulfide particles directly obtained by a sonification process from non-intercalated bulk material.

In embodiments of the first aspect of the invention, in step a) the particles of the transition metal sulfide, preferably the transition metal disulfide, have a particle size in the range of 1 nm to 6 μm.

In embodiments of the first aspect of the invention, in step a) the particles of the transition metal sulfide, preferably the transition metal disulfide, have a particle size in the range of 1 nm to 1000 nm.

In embodiments of the first aspect of the invention, in step a) the particles of the transition metal sulfide, preferably the transition metal disulfide, have a particle high in the range of 1 nm to 1000 nm, preferably in the range of 20 nm to 300 nm, more preferably in the range of 20 nm to 100 nm. The particle size and/or the particle high can be determined by scanning electron microscope (SEM), transmission electron microscopy (TEM) or atomic/scanning force microscope (AFM).

In embodiments of the first aspect of the invention, in step a) the particles of the transition metal sulfide, preferably the transition metal disulfide, have a particle size in the range of 50 nm to 500 nm.

In embodiments of the first aspect of the invention, in step a) the particles of the transition metal sulfide, preferably the transition metal disulfide, have a particle size in the range of 50 nm to 300 nm.

In embodiments of the first aspect of the invention, in step a) the particles of the transition metal sulfide, preferably the transition metal disulfide, have a particle size in the range of 80 nm to 150 nm.

In embodiments of the first aspect of the invention, the transition metal sulfide, preferably the transition metal disulfide, is bulk material.

In embodiments of the first aspect of the invention, the transition metal of the transition metal sulfide, preferably the transition metal disulfide, is selected from the group consisting of tungsten, molybdenum, titanium and tin.

In embodiments of the first aspect of the invention, the transition metal sulfide, preferably the transition metal disulfide, is selected from the group consisting of $WS_2$, $MoS_2$, $TiS_2$, $SnS_2$ and combinations thereof, preferably $MoS_2$, $TiS_2$, $SnS_2$ and combinations thereof, more preferably $MoS_2$.

In embodiments of the first aspect of the invention, the organic solvent has a boiling point ≤100° C. Preferably, the organic solvent is selected from the following group: water, acetonitrile, alcohol, e.g. isopropanol, and combinations thereof.

In embodiments of the first aspect of the invention, the sample is applied on the sample holder as a single spot via a dried-droplet method.

In embodiments of the first aspect of the invention, the sample is applied in liquid form on the surface of the sample holder.

In embodiments of the first aspect of the invention, after step a) each of the matrix and the analyte of interest forms a layer structure, wherein the layer structure of the matrix is formed between the surface of the sample holder and the layer structure of the analyte of interest.

In embodiments of the first aspect of the invention, the layer structure of the matrix is formed as a monolayer or single layer. Preferably, the monolayer has a thickness of 20-300 nm, more preferably 20 nm to 100 nm.

In embodiments of the first aspect of the invention, the layer structure of the analyte of interest is formed as a monolayer.

In embodiments of the first aspect of the invention, the at least one analyte of interest is embedded in the matrix and/or arranged on the surface of the matrix, which is arranged facing away of the surface of the sample holder.

In embodiments of the first aspect of the invention, before step a) a further step a1) is carried out:

a1) Sonication of the Matrix.

In embodiments of the first aspect of the invention, the sonication process a1) is carried out by the use of a probe-type ultrasonic homogenizer or an ultrasonic bath. The using of the probe-type ultrasonic homogenizer and the ultrasonic bath is known for a skilled person and thus not explained in detail.

In embodiments of the first aspect of the invention, the sample holder is capable of holding or carrying the sample.

In embodiments of the first aspect of the invention, the sample holder comprises or consists of a material, which is selected from the group consisting of steel, copper, ITO and aluminium.

In embodiments of the first aspect of the invention, the sample holder comprises a surface facing the laser irradiation and/or facing a laser irradiation source capable of emitting laser irradiation with a wavelength of smaller than 400 nm.

In embodiments of the first aspect of the invention, the sample holder is a MALDI-steel-plate or ITO-glass slide or copper conductive tape.

In embodiments of the first aspect of the invention, the surface is an electrically conductive surface.

In embodiments of the first aspect of the invention, the electrically conductive surface can be structured or undefined.

In embodiments of the first aspect of the invention, the surface, preferably the electrically conductive surface, comprises structures, wherein the structures are shaped as rectangle or pentagon or hexagon in plan view. The rectangle can be rectangular or square.

In embodiments of the first aspect of the invention, the structuring can be performed as follows: A stamp or a stamping roller, that contains a negative of the aimed structure, is pressed against the surface, predominantly an aluminium or copper tape. The material of the stamp, preferably steel, must be consisting of a higher hardness compared to the surface. After releasing the stamp, evenly arranged cavities are formed with depths of about 500 μm. The structures of the cavities are either e.g. quadratic or hexagonal, arranged in a symmetrical assembly.

In embodiments of the first aspect of the invention, the matrix is formed as a layer having a size thickness in the range of 100 nm to 100 μm.

In embodiments of the first aspect of the invention, crown ether, particularly 18-crown-6, is added in step a). The crown ether acting as complexation reagent, binding the naturally occurring sodium and potassium ions, that are present on the transition metal sulfides, preferably the transition metal disulfide.

In embodiments of the first aspect of the invention, said method is capable of detecting alkali ions and/or earth-alkali ions by a direct ionization in step b).

In embodiments of the first aspect of the invention, the alkali ions and/or earth-alkali ions are selected from the following group: $Na^+$, $K^+$, $Rb^+$, $Cs^+$, $Mg^{2+}$, $Ca^{2+}$, $Ba^{2+}$.

In embodiments of the first aspect of the invention, the analyte of interest has a molecular weight of smaller than 2000 Da.

In embodiments of the first aspect of the invention, the analyte of interest is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

In embodiments of the first aspect of the invention, the analyte of interest comprises a functional group. The functional group is capable of reaction with a reactive unit Q of a surface or a compound.

In embodiments of the first aspect of the present invention, the functional group is selected from the group consisting of carbonyl group, diene group, hydroxyl group, amine group, imine group, ketone group, aldehyde group, thiol group, diol group, phenolic group, expoxid group, disulfide group, nucleobase group, carboxylic acid group, terminal cysteine group, terminal serine group and azide group.

In embodiments of the first aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group. Aldoses (aldehyde and keto) exist as acetal and hemiacetals, a sort of masked form of the parent aldehyde/keto.

In embodiments of the first aspect of the present invention, the carbonyl group is an amide group, the skilled person is well aware that the amide group as such is a stable group, but that it can be hydrolyzed to convert the amide group into an carboxylic acid group and an amino group. Hydrolysis of the amide group may be achieved via acid/base catalysed reaction or by enzymatic process either of which is well-known to the skilled person. In embodiments of the first aspect of the present invention, wherein the carbonyl group is a masked aldehyde group or a masked keto group, the respective group is either a hemiacetal group or acetal group, in particular a cyclic hemiacetal group or acetal group. In embodiments of the first aspect of the present invention, the acetal group, is converted into an aldehyde or keto group before reaction with the compound.

In embodiments of the first aspect of the present invention, the carbonyl group is a keto group. In embodiments of the first aspect of the present invention, the keto group may be transferred into an intermediate imine group before reacting with the reactive unit of compounds. In embodiments of the first aspect of the present invention, the analyte molecule comprising one or more keto groups is a ketosteroid. In particular embodiments of the first aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 16-ketoestradiol, 16-alpha-hydroxyestrone, 2-hydroxyestrone-3-methylether, prednisone, prednisolone, pregnenolone, progesterone, dehydroepiandrosterone (DHEA), 17-hydroxypregnenolone, 17-hydroxyprogesterone, androsterone, epiandrosterone, Δ4-androstenedione, 11-deoxycortisol, corticosterone, 21-deoxycortisol, 11-deoxycorticosterone, allopregnanolone and aldosterone.

In embodiments of the first aspect of the present invention, the carbonyl group is a carboxyl group. In embodiments of the first aspect of the present invention, the carboxyl group reacts directly with the compound or it is converted into an activated ester group before reaction with the compound. In embodiments of the first aspect of the present invention, the analyte molecule comprising one or more carboxyl groups is selected from the group consisting of Δ8-tetrahydrocannabinolic acid, benzoylecgonin, salicylic acid, 2-hydroxybenzoic acid, gabapentin, pregabalin, valproic acid, vancomycin, methotrexate, mycophenolic acid, montelukast, repaglinide, furosemide, telmisartan, gemfibrozil, diclofenac, ibuprofen, indomethacin, zomepirac, isoxepac and penicillin. In embodiments of the first aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenyalanine, valine, proline and glycine.

In embodiments of the first aspect of the present invention, the carbonyl group is an aldehyde group. In embodiments of the first aspect of the present invention, the aldehyde group may be transferred into an intermediate imine group before reacting with the reactive unit of compounds. In embodiments of the first aspect of the present invention, the analyte molecule comprising one or more aldehyde groups is selected from the group consisting of pyridoxal, N-acetyl-D-glucosamine, alcaftadine, streptomycin and josamycin.

In embodiments of the first aspect of the present invention, the carbonyl group is an carbonyl ester group. In embodiments of the first aspect of the present invention, the analyte molecule comprising one or more ester groups is selected from the group consisting of cocaine, heroin, Ritalin, aceclofenac, acetylcholine, amcinonide, amiloxate, amylocaine, anileridine, aranidipine artesunate and pethidine.

In embodiments of the first aspect of the present invention, the carbonyl group is an anhydride group. In embodiments of the first aspect of the present invention, the analyte molecule comprising one or more anhydride groups is selected from the group consisting of cantharidin, succinic anhydride, trimellitic anhydride and maleic anhydride.

In embodiments of the first aspect of the present invention, the analyte molecule comprises one or more diene groups, in particular to conjugated diene groups, as functional group. In embodiments of the first aspect of the present invention, the analyte molecule comprising one or more diene groups is a secosteroid. In embodiments, the secosteroid is selected from the group consisting of cholecalciferol (vitamin D3), ergocalciferol (vitamin D2), calcifediol, calcitriol, tachysterol, lumisterol and tacalcitol. In particular, the secosteroid is vitamin D, in particular vitamin D2 or D3 or derivates thereof. In particular embodiments, the secosteroid is selected from the group consisting of vitamin D2, vitamin D3, 25-hydroxyvitamin D2, 25-hydroxyvitamin D3 (calcifediol), 3-epi-25-hydroxyvitamin D2, 3-epi-25-hydroxyvitamin D3, 1,25-dihydroxyvitamin D2, 1,25-dihydroxyvitamin D3 (calcitriol), 24,25-dihydroxyvitamin D2, 24,25-dihydroxyvitamin D3. In embodiments of the first aspect of the present invention, the analyte molecule comprising one or more diene groups is selected from the group consisting of vitamin A, tretinoin, isotretinoin, alitretinoin, natamycin, sirolimus, amphotericin B, nystatin, everolimus, temsirolimus and fidaxomicin.

In embodiments of the first aspect of the present invention, the analyte molecule comprises one or more hydroxyl group as functional group. In embodiments of the first aspect of the present invention, the analyte molecule comprises a single hydroxyl group or two hydroxyl groups. In embodiments wherein more than one hydroxyl group is present, the two hydroxyl groups may be positioned adjacent to each other (1,2-diol) or may be separated by 1, 2 or 3 C atoms (1,3-diol, 1,4-diol, 1,5-diol, respectively). In particular embodiments of the first aspect, the analyte molecule comprises a 1,2-diol group. In embodiments, wherein only one hydroxyl group is present, said analyte is selected from the group consisting of primary alcohol, secondary alcohol and tertiary alcohol. In embodiments of the first aspect of the present invention, wherein the analyte molecule comprises one or more hydroxyl groups, the analyte is selected from the group consisting of benzyl alcohol, menthol, L-carnitine, pyridoxine, metronidazole, isosorbide mononitrate, guaifenesin, clavulanic acid, Miglitol, zalcitabine, isoprenaline, aciclovir, methocarbamol, tramadol, venlafaxine, atropine, clofedanol, alpha-hydroxyalprazolam, alpha-Hydroxytriazolam, lorazepam, oxazepam, Temazepam, ethyl glucuronide, ethylmorphine, morphine, morphine-3-glucuronide, buprenorphine, codeine, dihydrocodeine, p-hydroxypropoxyphene, 0-desmethyltramadol, Desmetramadol, dihydroquinidine and quinidine. In embodiments of the first aspect of the present invention, wherein the analyte molecule comprises more than one hydroxyl groups, the analyte is selected from the group consisting of vitamin C, glucosamine, mannitol, tetrahydrobiopterin, cytarabine, azacitidine, ribavirin, floxuridine, Gemcitabine, Streptozotocin, adenosine, Vidarabine, cladribine, estriol, trifluridine, clofarabine, nadolol, zanamivir, lactulose, adenosine monophosphate, idoxuridine, regadenoson, lincomycin, clindamycin, Canagliflozin, tobramycin, netilmicin, kanamycin, ticagrelor, epirubicin, doxorubicin, arbekacin, streptomycin, ouabain, amikacin, neomycin, framycetin, paromomycin, erythromycin, clarithromycin, azithromycin, vindesine, digitoxin, digoxin, metrizamide, acetyldigitoxin, deslanoside, Fludarabine, clofarabine, gemcitabine, cytarabine, capecitabine, vidarabine, and plicamycin.

In embodiments of the first aspect of the present invention, the analyte molecule comprises one or more thiol group (including but not limited to alkyl thiol and aryl thiol groups) as functional group. In embodiments of the first aspect of the present invention, the analyte molecule comprising one or more thiol groups is selected from the group consisting of thiomandelic acid, DL-captopril, DL-thiorphan, N-acetylcysteine, D-penicillamine, glutathione, L-cysteine, zofenoprilat, tiopronin, dimercaprol, succimer.

In embodiments of the first aspect of the present invention, the analyte molecule comprises one or more disulfide group as functional group. In embodiments of the first aspect of the present invention, the analyte molecule comprising one or more disulfide groups is selected from the group consisting of glutathione disulfide, dipyrithione, selenium sulfide, disulfiram, lipoic acid, L-cystine, fursultiamine, octreotide, desmopressin, vapreotide, terlipressin, linaclotide and peginesatide. Selenium sulfide can be selenium disulfide, $SeS_2$, or selenium hexasulfide, $Se_2S_6$.

In embodiments of the first aspect of the present invention, the analyte molecule comprises one or more epoxide group as functional group. In embodiments of the first aspect of the present invention, the analyte molecule comprising one or more epoxide groups is selected from the group consisting of Carbamazepine-10,11-epoxide, carfilzomib, furosemide epoxide, fosfomycin, sevelamer hydrochloride, cerulenin, scopolamine, tiotropium, tiotropium bromide, methylscopolamine bromide, eplerenone, mupirocin, natamycin, and troleandomycin.

In embodiments of the first aspect of the present invention, the analyte molecule comprises one or more phenol groups as functional group. In particular embodiments of the first aspect of the present invention, analyte molecules comprising one or more phenol groups are steroids or steroid-like compounds. In embodiments of the first aspect of the present invention, the analyte molecule comprising one or more phenol groups is a steroid or a steroid-like compound having an A-ring which is $sp^2$ hybridized and an OH group at the 3-position of the A-ring. In particular embodiments of the first aspect of the present invention, the steroid or steroid-like analyte molecule is selected from the group consisting of estrogen, estrogen-like compounds, estrone (El), estradiol (E2), 17a-estradiol, 17b-estradiol, estriol (E3), 16-epiestriol, 17-epiestriol, and 16, 17-epiestriol and/or metabolites thereof. In embodiments, the metabolites are selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHEl), 2-methoxyestrone (2-MeOEl), 4-methoxyestrone (4-MeOEl), 2-hydroxyestrone-3-methyl ether (3-MeOEl), 2-methoxyestradiol (2-MeOE2), 4-methoxyestradiol (4-MeOE2), 2-hydroxyestrone (2-OHE1), 4-hydroxyestrone (4-OHE1), 2-hydroxyestradiol (2-OHE2), estrone (El), estrone sulfate (Els), 17a-estradiol (E2a), 17b-estradiol (E2B), estradiol sulfate (E2S), equilin (EQ), 17a-dihydroequilin (EQa), 17b-dihydroequilin (EQb), Equilenin (EN), 17-dihydroequilenin (ENa), 17a-dihydroequilenin, 170-dihydroequilenin (ENb), Δ8,9-dehydroestrone (dEl), Δ8,9-dehydroestrone sulfate (dEls), Δ9-tetrahydrocannabinol, mycophenolic acid. β or b can be used interchangeable. α and a can be used interchangeable.

In embodiments of the first aspect of the present invention, the analyte molecule comprises an amine group as functional group. In embodiments of the first aspect of the present invention, the amine group is an alkyl amine or an aryl amine group. In embodiments of the first aspect of the present invention, the analyte comprising one or more amine groups is selected from the group consisting of proteins and peptides. In embodiments of the first aspect of the present invention, the analyte molecule comprising an amine group is selected from the group consisting of 3,4-methylenedioxyamphetamine, 3,4-methylenedioxy-N-ethylamphetamine, 3,4-methylenedioxymethamphetamine, Amphetamine, Methamphetamine, N-methyl-1,3-benzodioxolylbutanamine, 7-aminoclonazepam, 7-aminoflunitrazepam, 3,4-dimethylmethcathinone, 3-fluoromethcathinone, 4-methoxymethcathinone, 4-methylethcathinone, 4-methylmethcathinone, amfepramone, butylone, ethcathinone, elephedrone, methcathinone, methylone, methylenedioxypyrovalerone, benzoylecgonine, dehydronorketamine, ketamine, norketamine, methadone, normethadone, 6-acetylmorphine, diacetylmorphine, morphine, norhydrocodone, oxycodone, oxymorphone, phencyclidine, norpropoxyphene, amitriptyline, clomipramine, dothiepin, doxepin, imipramine, nortriptyline, trimipramine, fentanyl, glycylxylidide, lidocaine, monoethylglycylxylidide, N-acetylprocainamide, procainamide, pregabalin, 2-Methylamino-1-(3,4-methylendioxyphenyl)butan, N-methyl-1,3-benzodioxolylbutanamine, 2-Amino-1-(3,4-methylendioxyphenyl)butan, 1,3-benzodioxolylbutanamine, normeperidine, 0-Destramadol, desmetramadol, tramadol, lamotrigine, Theophylline, amikacin, gentamicin, tobramycin, vancomycin, Methotrexate, Gabapentin sisomicin and 5-methylcytosine.

In embodiments of the first aspect of the present invention, the analyte molecule is a carbohydrate or substance having a carbohydrate moiety, e.g. a glycoprotein or a nucleoside. In embodiments of the first aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the first aspect of the present invention, the disaccharide is selected from the group consisting of sucrose, maltose and lactose. In embodiments of the first aspect of the present invention, the analyte molecule is a substance comprising above described mono-, di-, tri-, tetra-, oligo- or polysaccharide moiety.

In embodiments of the first aspect of the present invention, the analyte molecule comprises an azide group as functional group which is selected from the group consisting of alkyl or aryl azide. In embodiments of the first aspect of the present invention, the analyte molecule comprising one or more azide groups is selected from the group consisting of zidovudine and azidocillin.

Such analyte molecules may be present in biological or clinical samples such as body liquids, e.g. blood, serum, plasma, urine, saliva, spinal fluid, etc., tissue or cell extracts, etc. In embodiments of the first aspect of the present invention, the analyte molecule(s) are present in a biological or clinical sample selected from the group consisting of blood, serum, plasma, urine, saliva, spinal fluid, and a dried blood spot. In some embodiments of the first aspect of the present invention, the analyte molecules may be present in a sample which is a purified or partially purified sample, e.g. a purified or partially purified protein mixture or extract.

In embodiments of the first aspect of the present invention, the reactive unit Q of the surface or compound is selected from the group consisting of a carbonyl reactive unit, a diene reactive unit, a hydroxyl reactive unit, an amino reactive unit, an imine reactive unit, a thiol reactive unit, a diol reactive unit, a phenol reactive unit, an epoxide reactive unit, a disulfide reactive unit, and an azido reactive unit.

According to step b) of said method, the at least one analyte of interest is ionized via laser irradiation having a wavelength of smaller than 400 nm.

In embodiments of the first aspect of the present invention, step b) is performed via a laser irradiation having a wavelength of smaller than or equal to 355 nm.

In embodiments of the first aspect of the present invention, the laser irradiation has a main wavelength of 355 nm.

In embodiments of the first aspect of the present invention, step b) is performed via a Nd:YAG laser or Nd:YLF laser or Nd:YVO4 laser or nitrogen laser, preferably Nd:YAG laser. Nd:YAG laser or Nd:YLF laser or Nd:YVO4 laser or nitrogen laser are known for a skilled person, and thus are not explained in detail.

In embodiments of the first aspect of the present invention, step b) is a matrix-assisted laser desorption and/or ionization process (MALDI).

In embodiments of the first aspect of the present invention, step b) is a MALDI-TOF measurement in a positive mode.

In embodiments of the first aspect of the present invention, step c) is a MALDI-TOF measurement in a positive mode.

In embodiments of the first aspect of the present invention, steps b) and c) are MALDI-TOF measurements in a positive mode.

According to step c) of said method, the analyte of interest is determined using mass spectrometry. The determination can be quantitative and/or qualitative.

In a second aspect, the present invention relates to the use of the method of the first aspect of the present invention for determining the at least one analyte of interest. All embodiments mentioned for the first aspect of the invention apply for the second aspect of the invention and vice versa.

In a third aspect, the present invention relates to a sample element for ionizing of at least one analyte of interest via laser irradiation having a wavelength of smaller than 400 nm,

- wherein the sample element comprises a sample holder and a sample, wherein the sample comprises a matrix and the at least one analyte of interest,
- wherein the sample holder comprises an electrically conductive surface, which faces the laser irradiation,
- wherein the matrix and the analyte of interest are arranged on the electrically conductive surface in the beam path of the laser irradiation,
- wherein the matrix comprises or consists of a transition metal sulfide, preferably a transition metal disulfide, which is formed as particles having a particle size in the range of 1 nm to 6 μm. All embodiments mentioned for the first aspect of the invention and/or second aspect of the invention apply for the third aspect of the invention and vice versa.

In a fourth aspect, the present invention relates to he use of the sample element the third aspect of the present invention for determining at least one analyte of interest. All embodiments mentioned for the first aspect of the invention and/or second aspect of the invention and/or third aspect of the invention apply for the fourth aspect of the invention and vice versa.

In a fifth aspect, the present invention relates to a device for determining at least one analyte of interest comprising

- a laser irradiation source capable of emitting laser irradiation with a wavelength of smaller than 400 nm,
- the sample element of the third aspect of the present invention,
- a mass spectrometry unit. The mass spectrometry unit is capable of determining the analyte of interest.

All embodiments mentioned for the first aspect of the invention and/or second aspect of the invention and/or third aspect of the invention and/or fourth aspect of the invention apply for the fifth aspect of the invention and vice versa.

In embodiments of the fifth aspect of the present invention, the device is a clinical diagnostic system.

A "clinical diagnostics system" is a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g. by performing one or more pre-analytical and/or analytical and/or post-analytical steps. In particular, the clinical diagnostics system can comprise one or more analytical apparatuses, designed to execute respective workflows that are optimized for certain types of analysis, e.g. clinical chemistry, immunochemistry, coagulation, hematology, liquid chromatography separation, mass spectrometry, etc. Thus the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids, and also functional units for sorting, storing, transporting, identifying, separating, detecting. The clinical diagnostic system can comprise a sample preparation station for the automated preparation of samples comprising analytes of interest, optionally a liquid chromatography (LC) separation station comprising a plurality of LC channels and/or optionally a sample preparation/LC interface for inputting prepared samples into any one of the LC channels. The clinical diagnostic system can further comprise a controller programmed to assign samples to pre-defined sample preparation workflows each comprising a pre-defined sequence of sample preparation steps and requiring a pre-defined time for completion depending on the analytes of interest. The clinical diagnostic system can further comprise a mass spectrometer (MS) and an LC/MS interface for connecting the LC separation station to the mass spectrometer. The term "automatically" or "automated" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

In embodiments of the fifth aspect of the present invention, the clinical diagnostic system comprises a sample preparation station.

A "sample preparation station" can be a pre-analytical module coupled to one or more analytical apparatuses or a unit in an analytical apparatus designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing, etc.).

The clinical diagnostic system, e.g. the sample preparation station, may also comprise a buffer unit for receiving a plurality of samples before a new sample preparation start sequence is initiated, where the samples may be individually randomly accessible and the individual preparation of which may be initiated according to the sample preparation start sequence.

The clinical diagnostic system makes use of mass spectrometry more convenient and more reliable and therefore suitable for clinical diagnostics. In particular, high-throughput, e.g. up to 100 samples/hour or more with random access sample preparation and LC separation can be obtained while enabling online coupling to mass spectrometry. Moreover the process can be fully automated increasing the walk-away time and decreasing the level of skills required.

In a sixth aspect, the present invention relates to the use of the device of the fifth aspect of the present invention for determining at least one analyte of interest.

All embodiments mentioned for the first aspect of the invention and/or second aspect of the invention and/or third aspect of the invention and/or fourth aspect of the invention and/or fifth aspect of the invention apply for the sixth aspect of the invention and vice versa.

In a seventh aspect, the present invention relates to a kit suitable to perform a method of the first aspect of the invention comprising (A) a matrix comprising at least one transition metal sulfide, preferably at least one transition metal disulfide, which is formed as particles, (B) an organic solvent or mixtures thereof, (C) optionally at least one internal standard.

All embodiments mentioned for the first aspect of the invention and/or second aspect of the invention and/or third aspect of the invention and/or fourth aspect of the invention and/or fifth aspect of the invention and/or sixth aspect of the invention apply for the seventh aspect of the invention and vice versa.

In a eight aspect, the present invention relates to the use of a kit of the seventh aspect of the invention in a method of the first aspect of the invention.

All embodiments mentioned for the first aspect of the invention and/or second aspect of the invention and/or third aspect of the invention and/or fourth aspect of the invention and/or fifth aspect of the invention and/or sixth aspect of the invention and/or seventh aspect of the invention apply for the eighth aspect of the invention and vice versa.

In further embodiments, the present invention relates to the following aspects:

1. A method for determining at least one analyte of interest comprising the following steps:

a) Preparing a sample comprising a matrix and the at least one analyte of interest on a surface of a sample holder, wherein the matrix comprises at least one transition metal sulfide, preferably at least one transition metal disulfide, wherein the transition metal sulfide, preferably the transition metal disulfide, is formed as particles, wherein step a) comprises:

Applying the sample in liquid form on the surface of a sample holder and drying the sample, b) Ionizing the at least one analyte of interest via laser irradiation having a wavelength of smaller than 400 nm, and c) Determining the analyte of interest using mass spectrometry, wherein preferably the applying comprises (i) a combined applying of the matrix and the analyte of interest, followed by drying, or (ii) a sequentially applying of the matrix and the analyte of interest, wherein in case of the sequentially applying of the matrix and the analyte of interest, the drying is followed after each sequentially applying of the matrix and the analyte of interest.

2. The method of aspect 1, wherein the sample or the method is free of silver nanoparticles.

3. The method of any of the proceeding aspects, wherein the sample or the method is free of intercalated lithium.

4. The method of any of the proceeding aspects, which is free of a lithium mediated exfoliation step.

5. The method of any of the proceeding aspects, which is free of a sodium hydroxide assisted exfoliation step.

6. The method of any of the proceeding aspects, which is free of a porous nano structuring step.

7. The method of any of the proceeding aspects, wherein the matrix is dissolved in an organic solvent and sonicated to form a suspension of transition metal sulfide particles, preferably the transition metal disulfide particles.

8. The method of any of the proceeding aspects, wherein the organic solvent has a boiling point ≤100° C., preferably wherein the organic solvent is selected from the following group: water, acetonitrile, alcohol, e.g. isopropanol, and combinations thereof.

9. The method of any of the proceeding aspects, wherein said method is capable of detecting alkali ions and/or earth-alkali ions by a direct ionization in step b).

10. The method of aspect 8, wherein the alkali ions and/or earth-alkali ions are selected from the following group: $Na^+$, $K^+$, $Rb^+$, $Cs^+$, $Mg^{2+}$, $Ca^{2+}$, $Ba^{2+}$.

11. The method of any of the proceeding aspects, wherein the sample is applied on the sample holder as a single spot via a dried-droplet method.

12. The method of any of the proceeding aspects, wherein the sample is applied on the whole surface of the sample holder.

13. The method of any of the proceeding aspects, wherein after step a) each of the matrix and the analyte of interest forms a layer structure, wherein the layer structure of the matrix is formed between the surface of the sample holder and the layer structure of the analyte of interest.

14. The method of any of the proceeding aspects, wherein the layer structure of the matrix is formed as a monolayer.

15. The method of any of the proceeding aspects, wherein the layer structure of the analyte of interest is formed as a monolayer.

16. The method of any of the proceeding aspects, wherein the at least one analyte of interest is embedded in the matrix and/or arranged on the surface of the matrix, which is arranged facing away of the surface of the sample holder.

17. The method of any of the proceeding aspects, wherein before step a) a further step a1) is carried out:

a1) Sonication of the Matrix.

18. The method of any of the proceeding aspects, wherein the sonication process a1) is carried out by the use of a probe-type ultrasonic homogenizer or an ultrasonic bath.

19. The method of any of the proceeding aspects, wherein in step a) the particles of the transition metal sulfide, preferably the transition metal disulfide, have a particle size in the range of 1 nm to 6 μm.

20. The method of any of the proceeding aspects, wherein in step a) the particles of the transition metal sulfide, preferably the transition metal disulfide, have a particle size in the range of 1 nm to 1000 nm.

21. The method of any of the proceeding aspects, wherein in step a) the particles of the transition metal sulfide, preferably the transition metal disulfide, have a particle size in the range of 50 nm to 500 nm.

22. The method of any of the proceeding aspects, wherein in step a) the particles of the transition metal sulfide, preferably the transition metal disulfide, have a particle size in the range of 50 nm to 300 nm.

23. The method of any of the proceeding aspects, wherein in step a) the particles of the transition metal sulfide, preferably the transition metal disulfide, have a particle size in the range of 80 nm to 150 nm.

24. The method of any of the proceeding aspects, wherein the transition metal sulfide, preferably the transition metal disulfide, is bulk material.

25. The method of any of the proceeding aspects, wherein the transition metal of the transition metal sulfide, preferably the transition metal disulfide, is selected from the group consisting of thungsten, molybdenum, titanium and tin.

26. The method of any of the proceeding aspects, wherein the transition metal sulfide, preferably the transition metal disulfide, is selected from the group consisting of $WS_2$, $MoS_2$, $TiS_2$ and $SnS_2$, preferably $MoS_2$, 27. The method of any of the proceeding aspects, wherein the sample holder comprises or consists of a material, which is selected from the group consisting of steel, copper, ITO and aluminium.

28. The method of any of the proceeding aspects, wherein the sample holder is a MALDI-steel-plate or ITO-glass slide or copper conductive tape.

29. The method of any of the proceeding aspects, wherein the surface comprises structures, wherein the structures are shaped as rectangle or pentagon or hexagon in plan view.

30. The method of any of the proceeding aspects, wherein the surface is an electrically conductive surface.

31. The method of any of the proceeding aspects, wherein the electrically conductive surface is structured.

32. The method of any of the proceeding aspects, wherein the analyte of interest has a molecular weight of smaller than 2000 Da.

33. The method of any of the proceeding aspects, wherein the analyte of interest is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

34. The method of any of the proceeding aspects, wherein the matrix is formed as a layer having a size thickness in the range of 100 nm to 100 μm.

35. The method of any of the proceeding aspects, wherein crown ether, particularly 18-crown-6, is added in step a).

36. The method of any of the proceeding aspects, wherein step b) is performed via a laser irradiation having a wavelength of smaller than or equal to 355 nm.

37. The method of any of the proceeding aspects, wherein step b) is performed via a Nd:YAG laser or nitrogen laser, preferably Nd:YAG laser.

38. The method of any of the proceeding aspects, wherein step b) is a matrix-assisted laser desorption and/or ionization process (MALDI).

39. The method of any of the proceeding aspects, wherein steps b) and c) are MALDI-TOF measurements in a positive mode.

40. Use of the method of any one of aspects 1 to 39 for determining the at least one analyte of interest.

41. A sample element for ionizing of at least one analyte of interest via laser irradiation having a wavelength of smaller than 400 nm, wherein the sample element comprises a sample holder and a sample, wherein the sample comprises a matrix and the at least one analyte of interest, wherein the sample holder comprises an electrically conductive surface, which faces the laser irradiation, wherein the matrix and the analyte of interest are arranged on the electrically conductive surface in the beam path of the laser irradiation, wherein the matrix comprises or consists of a transition metal sulfide, preferably the transition metal disulfide, which is formed as particles having a particle size in the range of 1 nm to 6 μm.

42. Use of the sample element of aspect 41 for determining at least one analyte of interest.

43. A device for determining at least one analyte of interest comprising a laser irradiation source capable of emitting laser irradiation with a wavelength of smaller than 400 nm, the sample element of aspect 41, a mass spectrometry unit.

44. Use of the device of aspect 43 for determining at least one analyte of interest.

45. A kit suitable to perform a method of any one of aspects 1 to 39 comprising (A) a matrix comprising at least one transition metal sulfide, preferably at least one transition metal disulfide, which is formed as particles, (B) an organic solvent or mixtures thereof, (C) optionally at least one internal standard.

46. Use of a kit of aspect 45 in a method of any one of aspects 1 to 39.

EXAMPLES

The following examples are provided to illustrate, but not to limit the presently claimed invention.

Analytes Used for Evaluation:

Solutions of analytes are prepared from molecules of analytical interest, especially steroids and therapeutically relevant substances. For the main experiments, a mixture of seven naturally occurring steroids (namely Pr=Progesterone, Te=Testosterone, Es=Estradiol, S7=Androstenedione, S9=Cortisol, S10=Cortisone, S19=21-Deoxycortisol, each 14 μg/mL in $MeCN/H_2O$=50/50) as well as a mixture of seven therapeutically substances (namely T3=Amikacin (sulfate), T7=Digitoxin, T16=Mycophenolic acid, T37=Lidocain, T41=Digoxin, T62=Voriconazole, T71=Meropenem, 14 μg/mL in $MeCN/H_2O$=50/50) are prepared. Analytes are spotted on the pre-coated $MoS_2$ or $WS_2$ or $TiS_2$ or $SnS_2$ surface applying the dried-droplet method (0.7 μL).

To mimic a realistic matrix background, both analyte mixtures are additionally dissolved with horse serum supernatant (precipitated in MeCN) leading to a final concentration of analytes of 1.4 μg/mL (abbreviated as HSsup+S/T).

Laser Desorption/Ionization on Bulk Material:

The preparation of the suspensions includes weighing of a respective bulk $MoS_2$ or $WS_2$ material (particle size between 90 nm to 40 μm, purchased from Sigma-Aldrich), washing with $MeCN/H_2O$=50/50 and suspending in $MeCN/H_2O$=50/50 with a concentration between 3 mg/mL to 25 mg/mL, preferably 7 mg/mL. $TiS_2$ or $SnS_2$ material is washed with MeCN and suspended in MeCN with a concentration between 5 mg/mL to 30 mg/mL, preferably 14 mg/mL. The hereby formed suspension can be used directly after vortexing to coat a surface suitable for MALDI-MS measurement (commonly on a MALDI-steel-plate, ITO-glass slide, or similar) applying the dried-droplet-method (preferably 0.7 μL). Subsequently after analyte deposition and air-drying, MALDI-TOF measurements are performed in positive mode adjusting the laser intensity to an optimal value of about 4500 units ($MoS_2$ or $WS_2$) or rather 5500-6000 units ($TiS_2$ or 51152) with a total of 2000 laser shots per spot. Analyte signals naturally occurred as alkali adducts ([M+Na]+ and $[M+K]^+$). Resulting mass-to-charge ratios of alkali adducts with steroid analytes are: m/z=295 $[Es+Na]^+$, m/z=309 $[S7+Na]^+$, m/z=311 $[Te+Na]^+$, m/z=337 $[Pr+Na]^+$, m/z=369 $[S19+Na]^+$, m/z=383 $[S10+Na]^+$, m/z=385 $[S9+Na]^+$, m/z=325 $[S7+K]^+$, m/z=327 $[Te+K]^+$, m/z=353 $[Pr+K]^+$, m/z=385 $[S19+K]^+$, m/z=399 $[S10+K]^+$, m/z=401 $[S9+K]^+$. Resulting mass-to-charge ratios of alkali adducts with the therapeutic analytes are: m/z=257 $[T37+Na]^+$, m/z=343 $[T16+Na]^+$, m/z=372 $[T62+Na]^+$, m/z=406 $[T71+Na]^+$, m/z=608 $[T3+Na]^+$, m/z=787 $[T7+Na]^+$, m/z=803 $[T41+Na]^+$, m/z=273 $[T37+K]^+$, m/z=359 $[T16+K]^+$, m/z=388 $[T62+K]^+$, m/z=422 $[T71+K]^+$, m/z=624 $[T3+K]^+$, m/z=803 $[T7+K]^+$, m/z=819 $[T41+K]^+$.

The analyte selection is based on the presence of diverse functional groups, heteroatoms and polarities. In particular, challenging analytes are chosen, including Es (which is supposed to get ionized much better in the negative mode due to its respective basic gas phase character corresponding to the present phenol moiety within the molecule), T3/T7/T41 (which contain different glycan structures) and T71 (what is known for its limited stability). Therefore, not all selected analytes had been expected to succeed, but surprisingly all analytes have been shown to ionize with the presented method. No ion quenching (competition of analytes for the charge to get ionized) occurred. The method shows therefore independent ionization for the analytes.

FIG. 1A to FIG. 1D, FIG. 2A to FIG. 2D, FIG. 3A to FIG. 3D, and FIG. 4A to FIG. 4D show the MS spectra of a analyte mixture, in particular a steroid mixture and therapeutically substance mixture, respectively, which results from the method according to the first aspect of the present invention by using different bulk inorganic matrices. As it can seen from FIG. 1A to FIG. 1D, FIG. 2A to FIG. 2D, FIG. 3A to FIG. 3D, and FIG. 4A to FIG. 4D, the alkali ions $Na^+$ and $K^+$ can be directly detected via the method according to the first aspect of the present invention at m/z=23 and m/z=39, respectively.

Figure 1B:
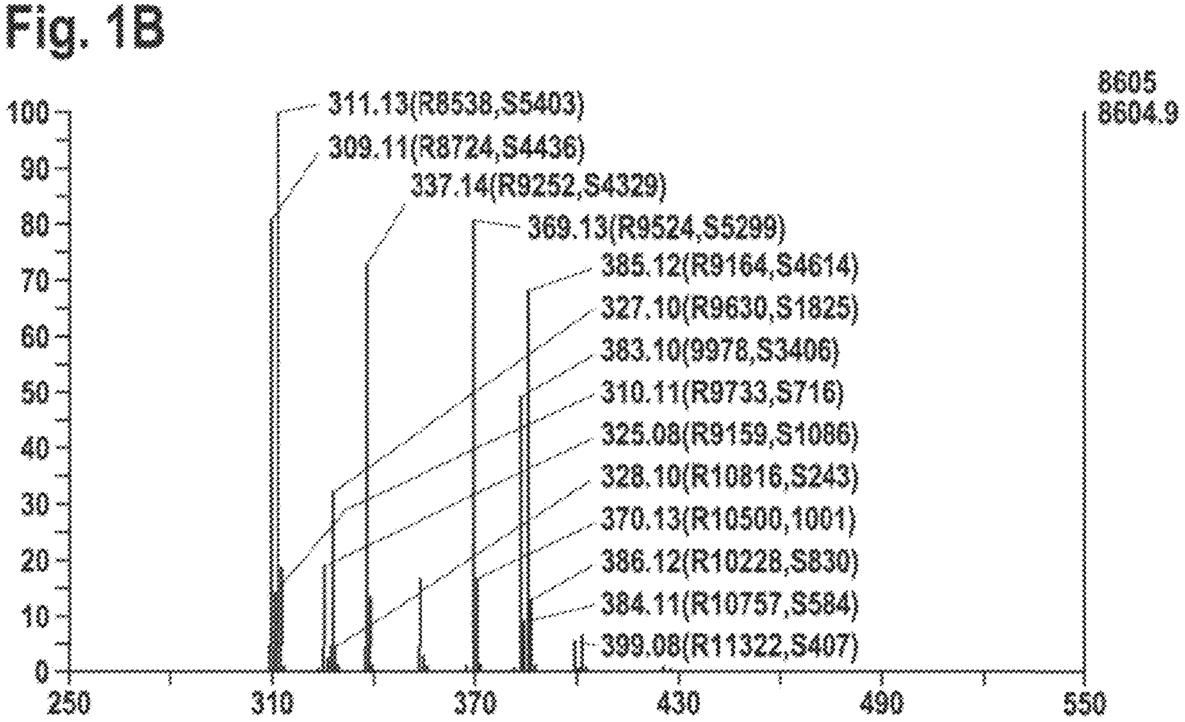

FIG. 1A and FIG. 1B show the relative intensity or absolute intensity as a function of the m/z of a steroid mixture comprising seven steroids: Te, Pr, Es, S7, S9, S10 and S19, each 14 μg/ml. The matrix is a bulk $MoS_2$ matrix having a particle size of about 6 μm. FIG. 1B is an enlargement of the MS spectrum of FIG. 1A in the m/z range of 250 to 550. FIG. 1A and FIG. 1B demonstrate a good desorption of the steroid analytes Te, Pr, S7, S9, S10 and S19, and an ionization mainly by formation of the corresponding sodium adducts $[M+Na]^+$ with minor amounts of potassium adducts formation $[M+K]^+$. Furthermore, no significant background signals can be observed.

Figure 1C:
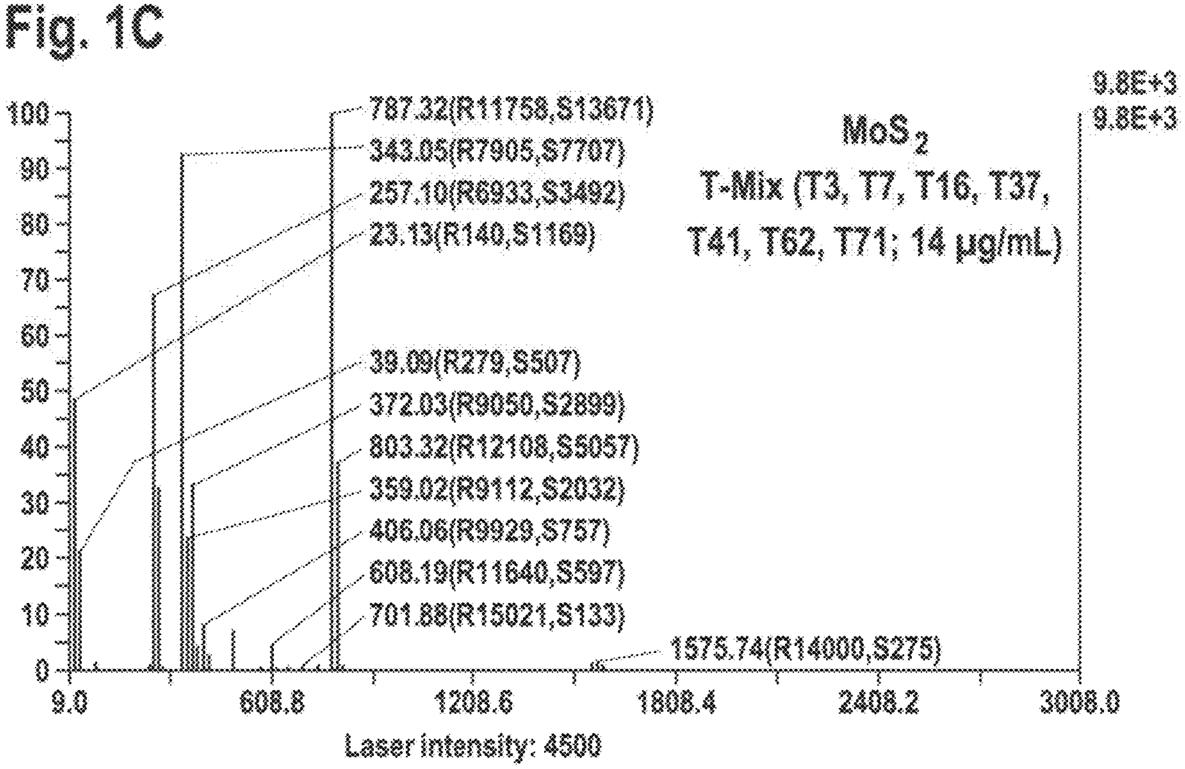
Figure 1D:
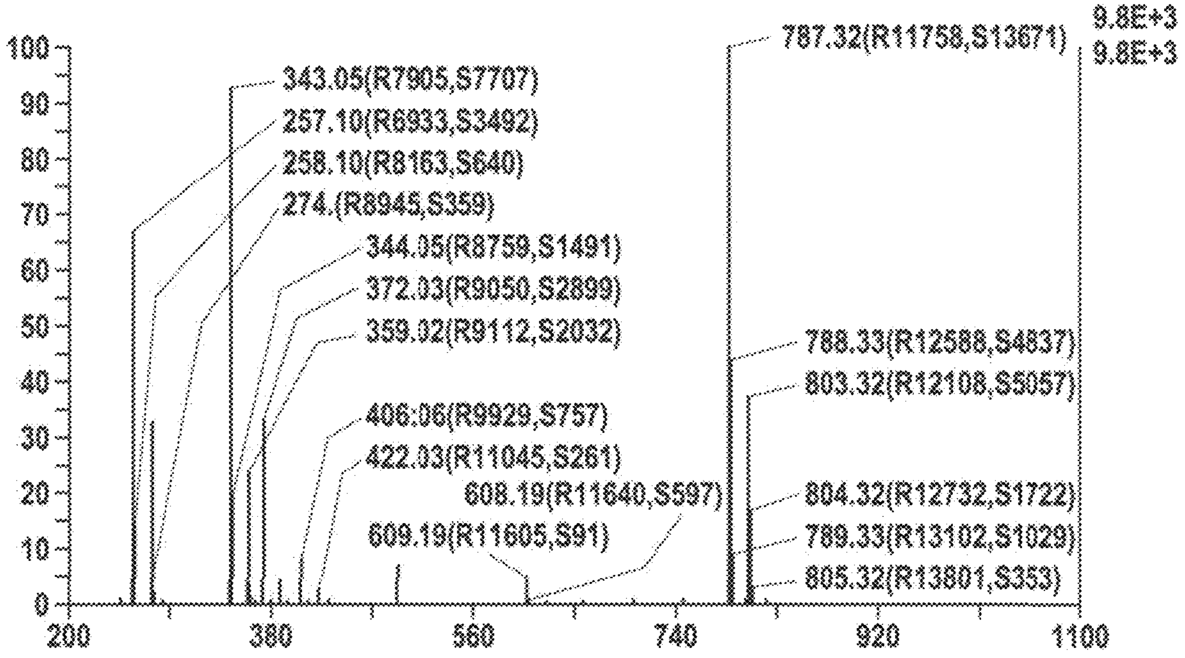

FIG. 1C and FIG. 1D show the relative intensity or absolute intensity as a function of the m/z of a mixture of seven therapeutically substances: T3, T7, T16, T37, T41, T62 and T71, each 14 μg/ml. The matrix is a bulk $MoS_2$ matrix having a particle size of about 6 μm. FIG. 1D is an enlargement of the MS spectrum of FIG. 1C in the m/z range of 200 to 1100. FIG. 1C and FIG. 1D demonstrate the desorption of the therapeutically substances T3, T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 2A:
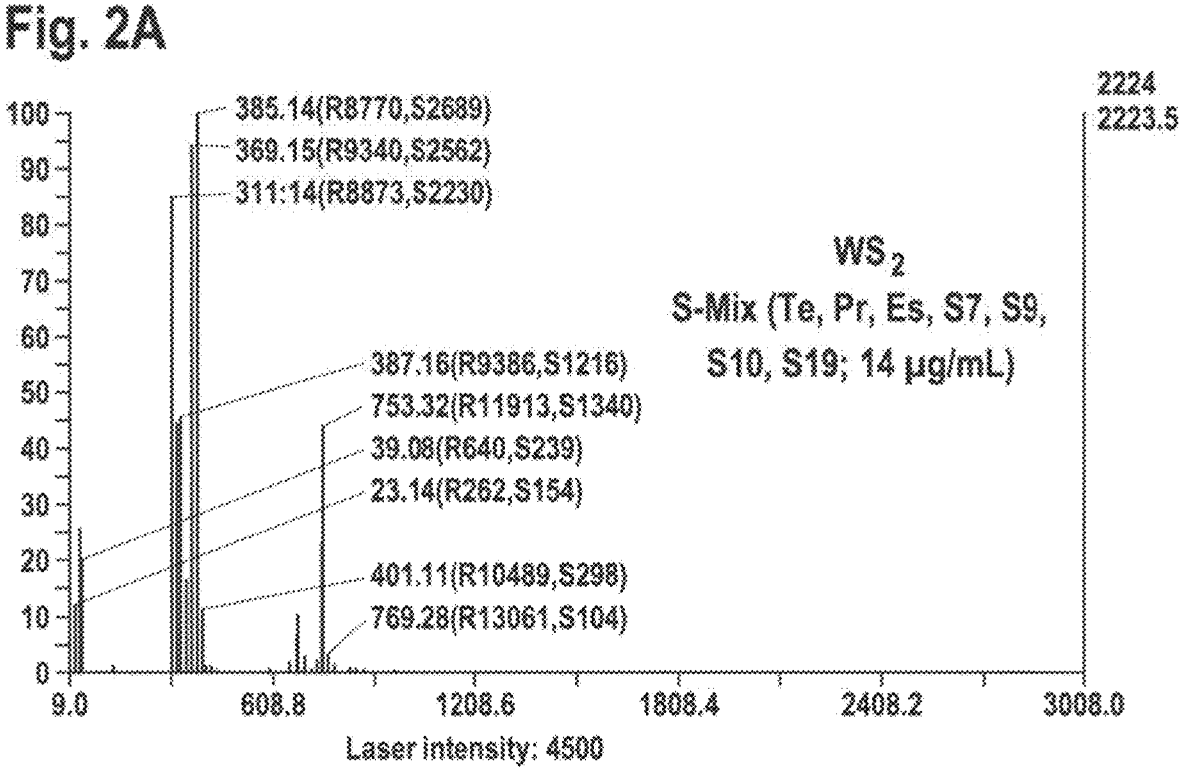
FIG. 2A to FIG. 2D show the MS spectra of a steroid mixture and therapeutically substance mixture, respectively.
Figure 2B:
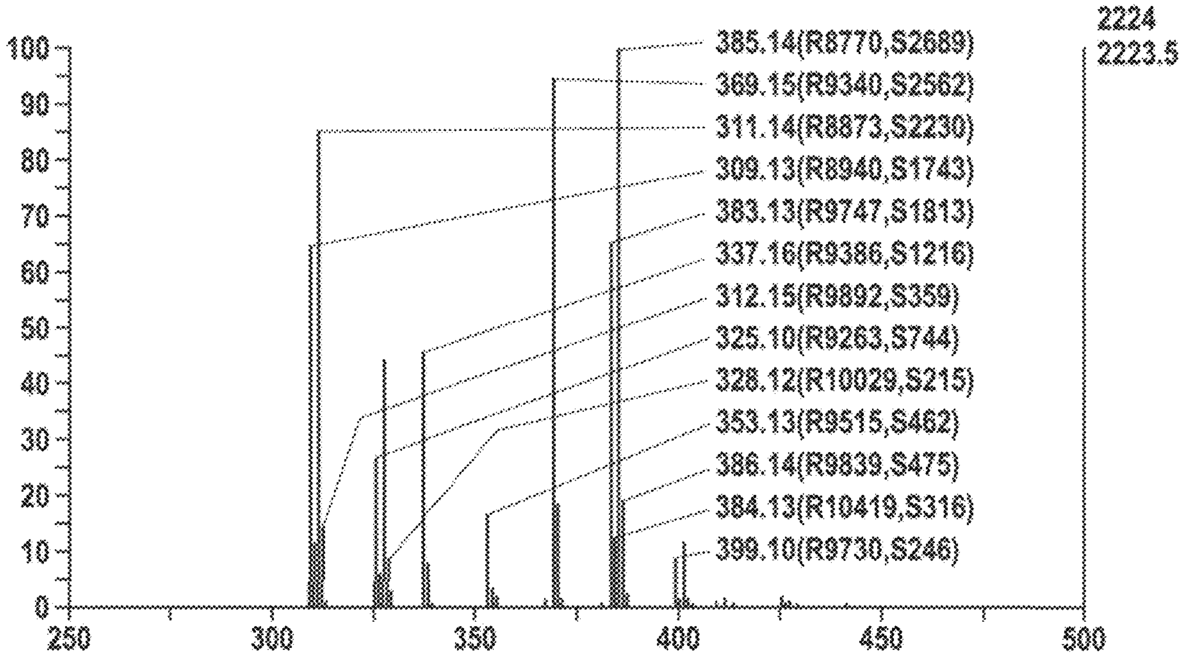

FIG. 2A and FIG. 2B show the relative intensity or absolute intensity as a function of the m/z of a steroid mixture comprising seven steroids: Te, Pr, Es, S7, S9, S10 and S19, each 14 μg/ml. The matrix is a bulk $WS_2$ matrix having a particle size of about 2 μm. FIG. 2B is an enlargement of the MS spectrum of FIG. 2A in the m/z range of 250 to 500. FIG. 2A and FIG. 2B demonstrate the desorption of the steroid analytes Te, Pr, S7, S9, S10 and S19, and an ionization mainly by formation of the corresponding sodium adducts $[M+Na]^+$ with also the potassium adducts formation $[M+K]^+$ and multiple alkali adducts formation (e.g. m/z=753 $[S19-H+Na+K]^+$). Furthermore, no significant background signals can be observed.

Figure 2C:
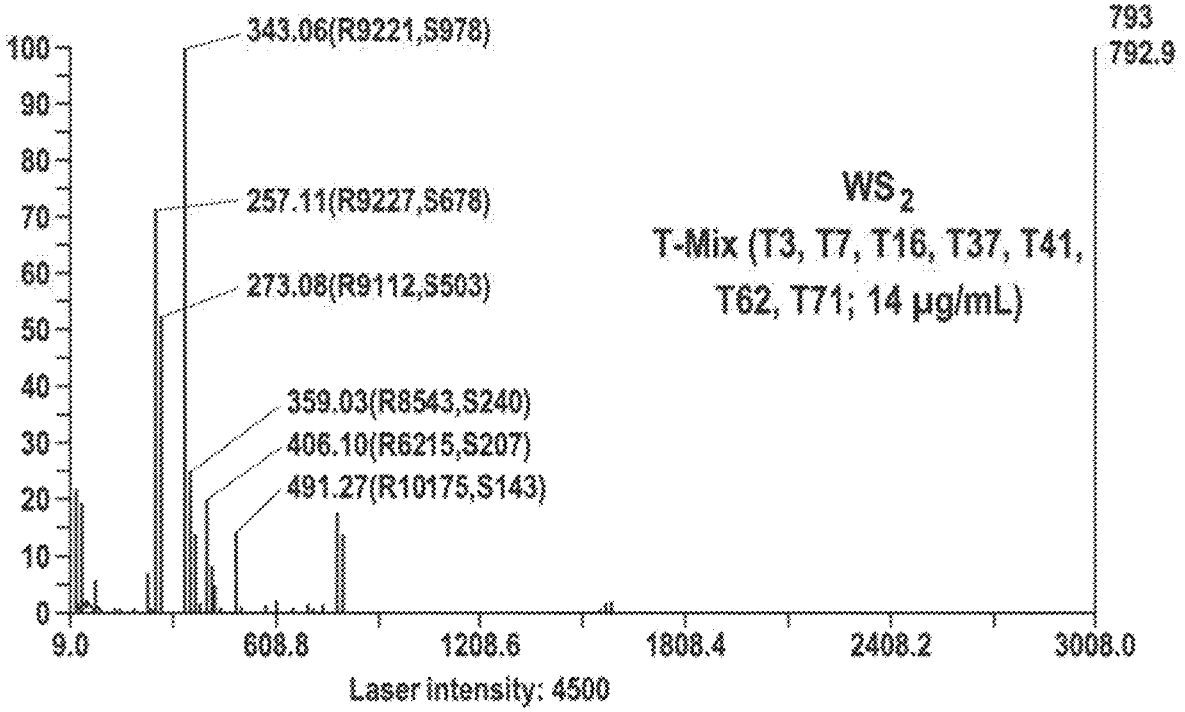
Figure 2D:
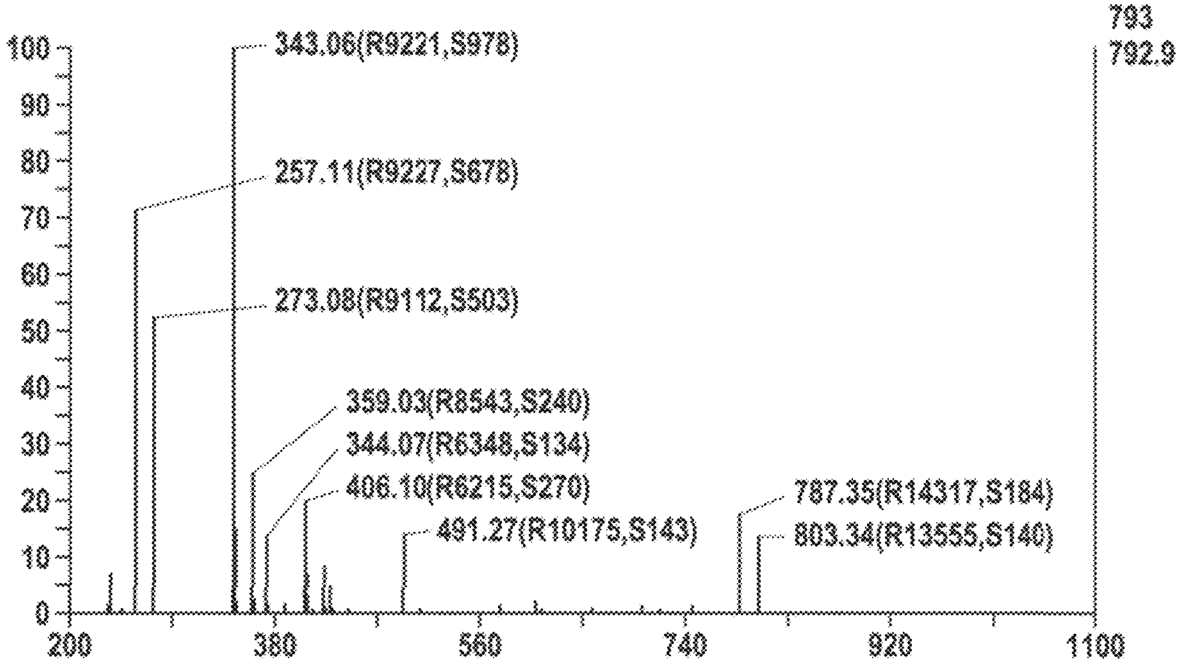

FIG. 2C and FIG. 2D show the relative intensity or absolute intensity as a function of the m/z of a mixture of seven therapeutically substances: T3, T7, T16, T37, T41, T62 and T71, each 14 μg/ml. The matrix is a large bulk $WS_2$ matrix having a particle size of about 2 μm. FIG. 2D is an enlargement of the MS spectrum of FIG. 2C in the m/z range of 200 to 1100. FIG. 2C and FIG. 2D demonstrate the desorption of the therapeutically substances T3, T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 3A:
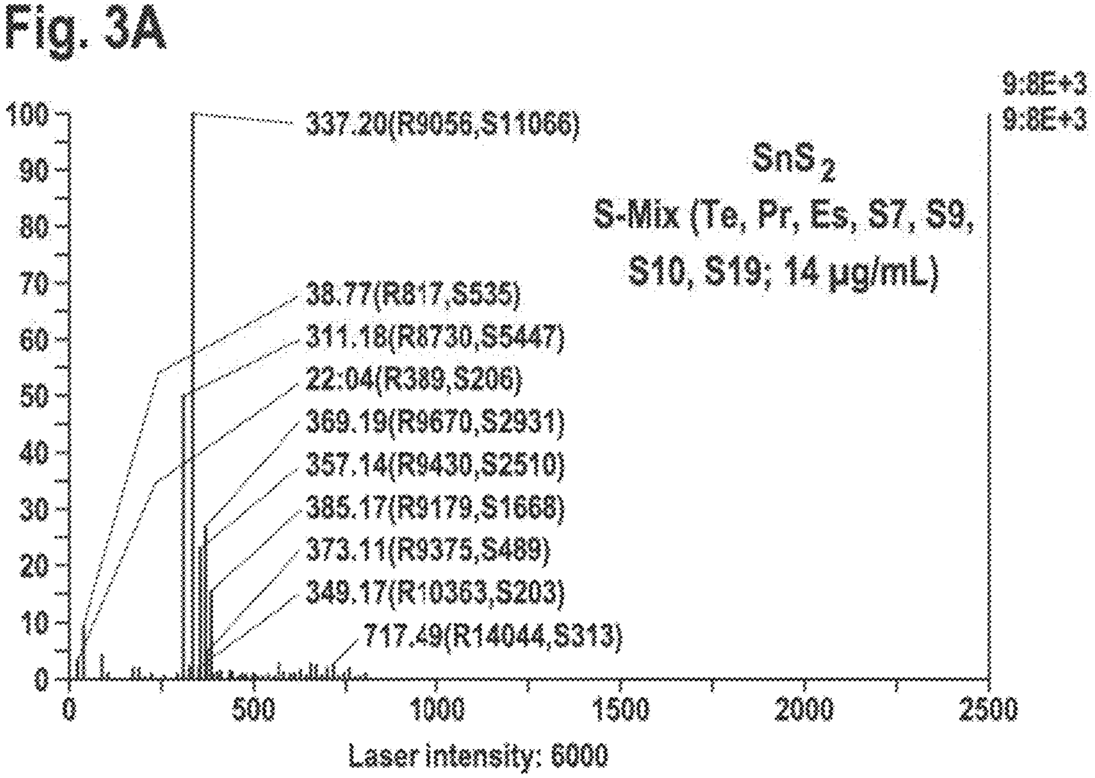
FIG. 3A to FIG. 3D show the MS spectra of a steroid mixture and therapeutically substance mixture, respectively.
Figure 3B:
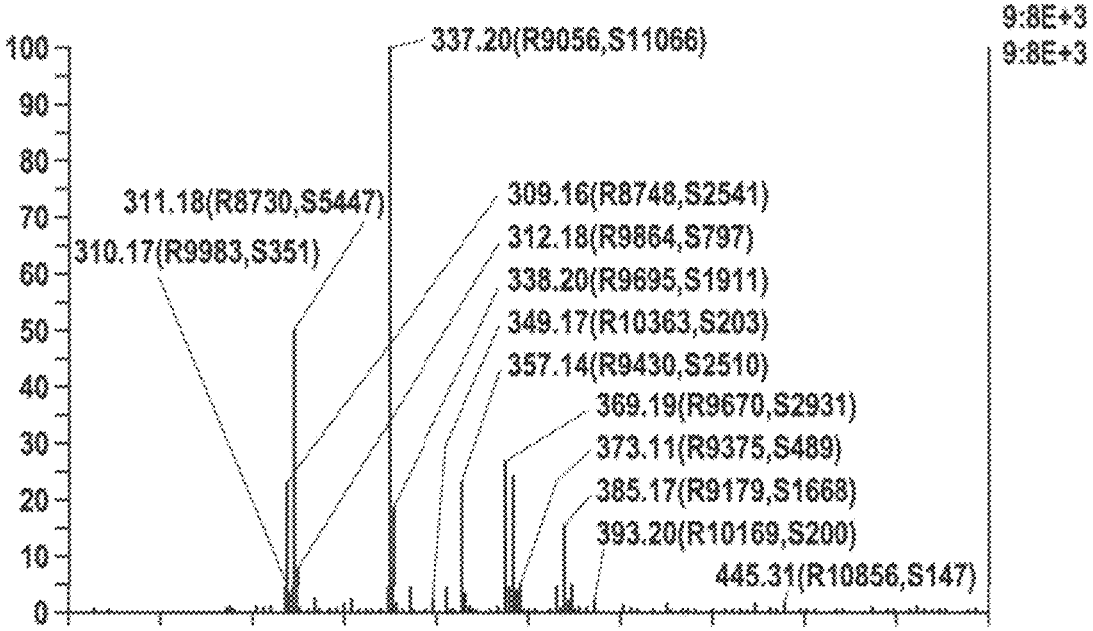

FIG. 3A and FIG. 3B show the relative intensity or absolute intensity as a function of the m/z of a steroid mixture comprising seven steroids: Te, Pr, Es, S7, S9, S10 and S19, each 14 μg/ml. The matrix is a bulk $SnS_2$ matrix. FIG. 3B is an enlargement of the MS spectrum of FIG. 3A in the m/z range of 250 to 500. FIG. 3A and FIG. 3B demonstrate the desorption of the steroid analytes Te, Pr, S7, S9, S10 and S19, and an ionization mainly by formation of the corresponding sodium adducts $[M+Na]^+$ with traces of potassium adducts formation $[M+K]^+$. Furthermore, just small background signals can be observed signals in the range of up to m/z=800.

Figure 3C:
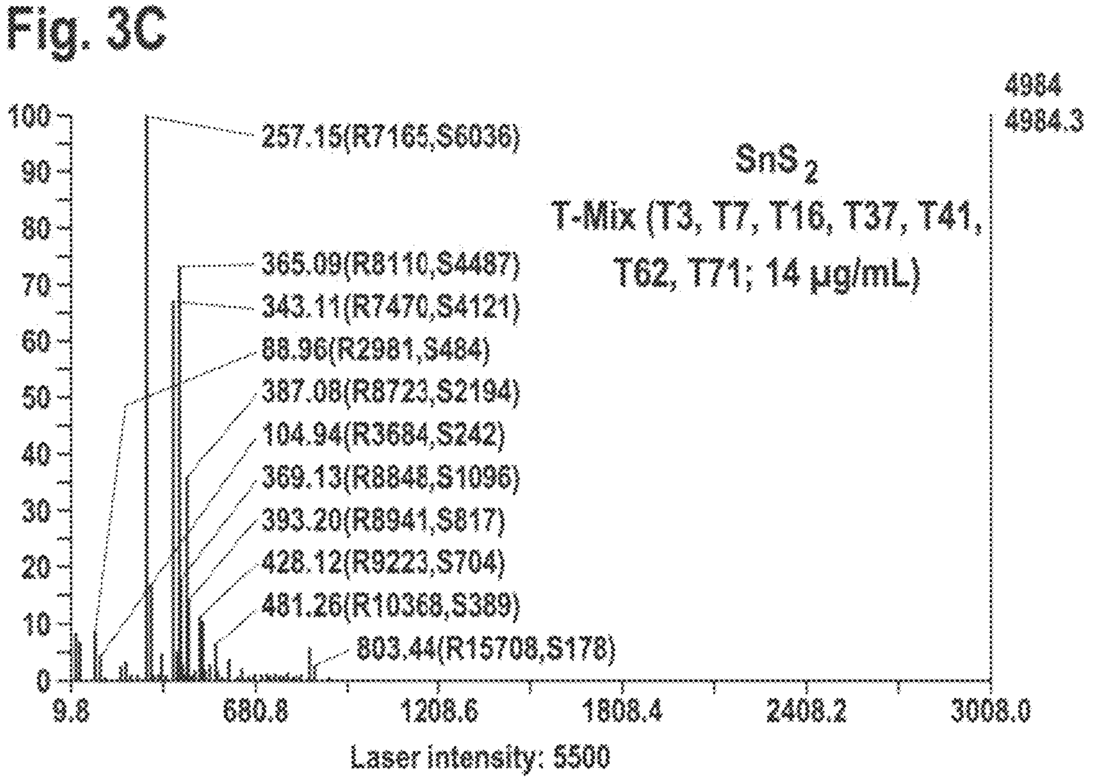
Figure 3D:
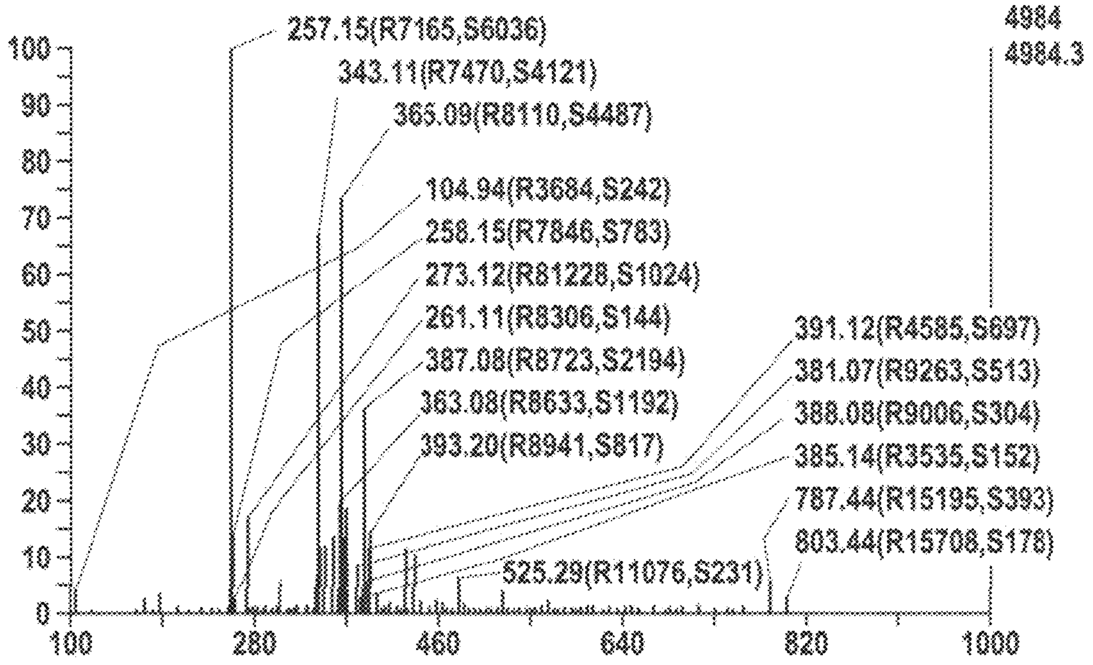

FIG. 3C and FIG. 3D show the relative intensity or absolute intensity as a function of the m/z of a mixture of seven therapeutically substances: T3, T7, T16, T37, T41, T62 and T71, each 14 μg/ml. The matrix is a bulk $SnS_2$ matrix. FIG. 3D is an enlargement of the MS spectrum of FIG. 3C in the m/z range of 100 to 1000. FIG. 3C and FIG. 3D demonstrate a desorption of the therapeutically substances T16, T37 with traces of T7, T41, T62, T71, and an ionization mainly by formation of the corresponding sodium adducts $[M+Na]^+$ with T37 and T16 also forming potassium adducts $[M+K]^+$. Some background can be observed signals in the range of up to m/z=800.

Figure 4A:
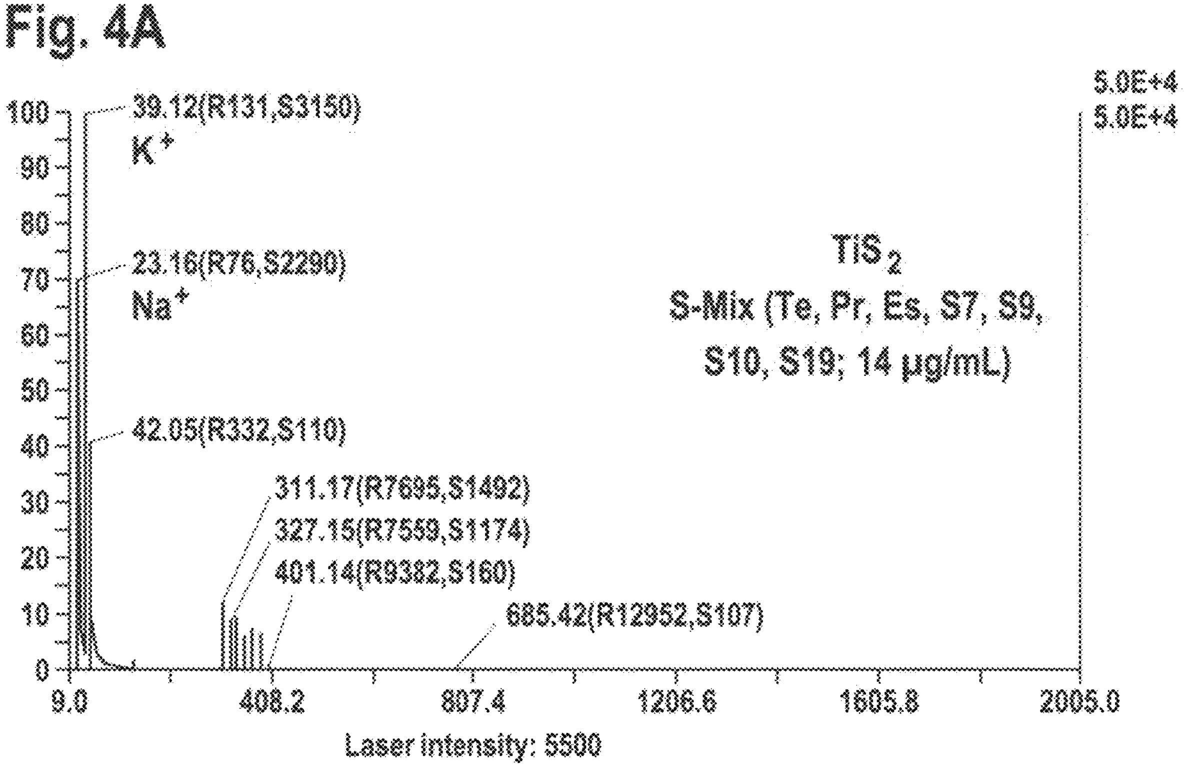
FIG. 4A to FIG. 4D show the MS spectra of a steroid mixture and therapeutically substance mixture, respectively.
Figure 4B:
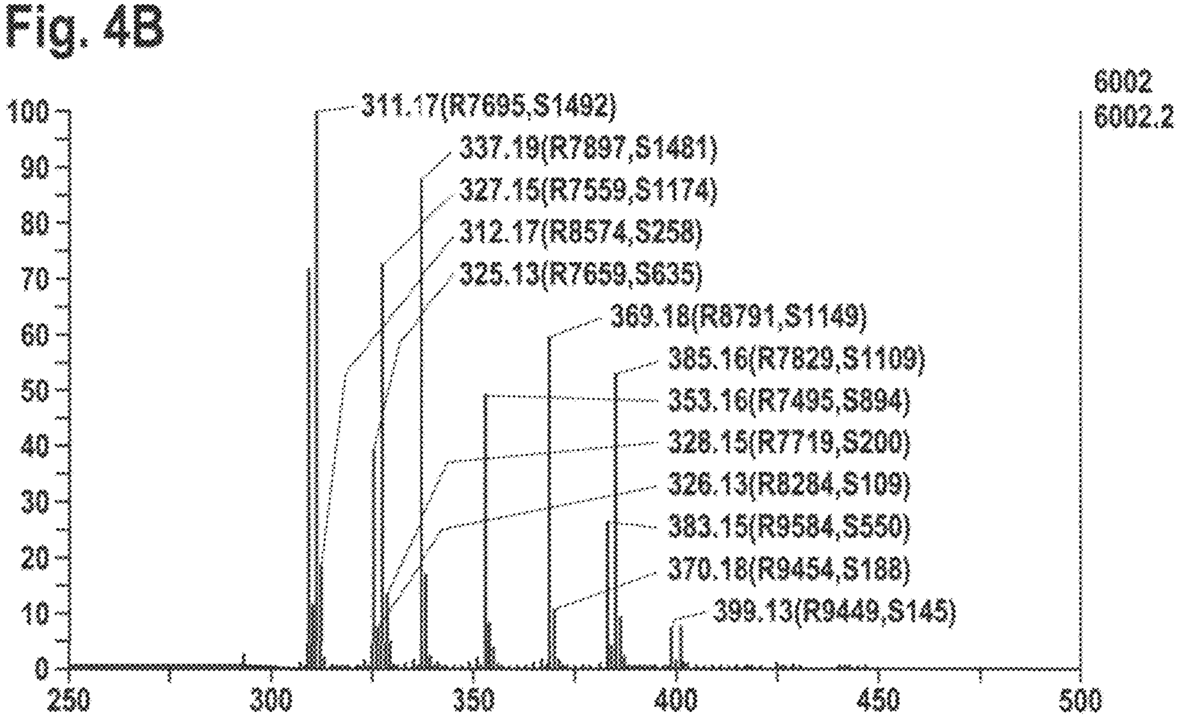

FIG. 4A and FIG. 4B show the relative intensity or absolute intensity as a function of the m/z of a steroid mixture comprising seven steroids: Te, Pr, Es, S7, S9, S10 and S19, each 14 μg/ml. The matrix is a bulk $TiS_2$ matrix. FIG. 4B is an enlargement of the MS spectrum of FIG. 4A in the m/z range of 250 to 500. FIG. 4A and FIG. 4B demonstrate the desorption of the steroid analytes Es, Te, Pr, S7, S9, S10 and S19, and an ionization mainly by formation of the corresponding sodium adducts $[M+Na]^+$ with some potassium adducts formation $[M+K]^+$. Furthermore, no significant background signals can be observed signals.

Figure 4C:
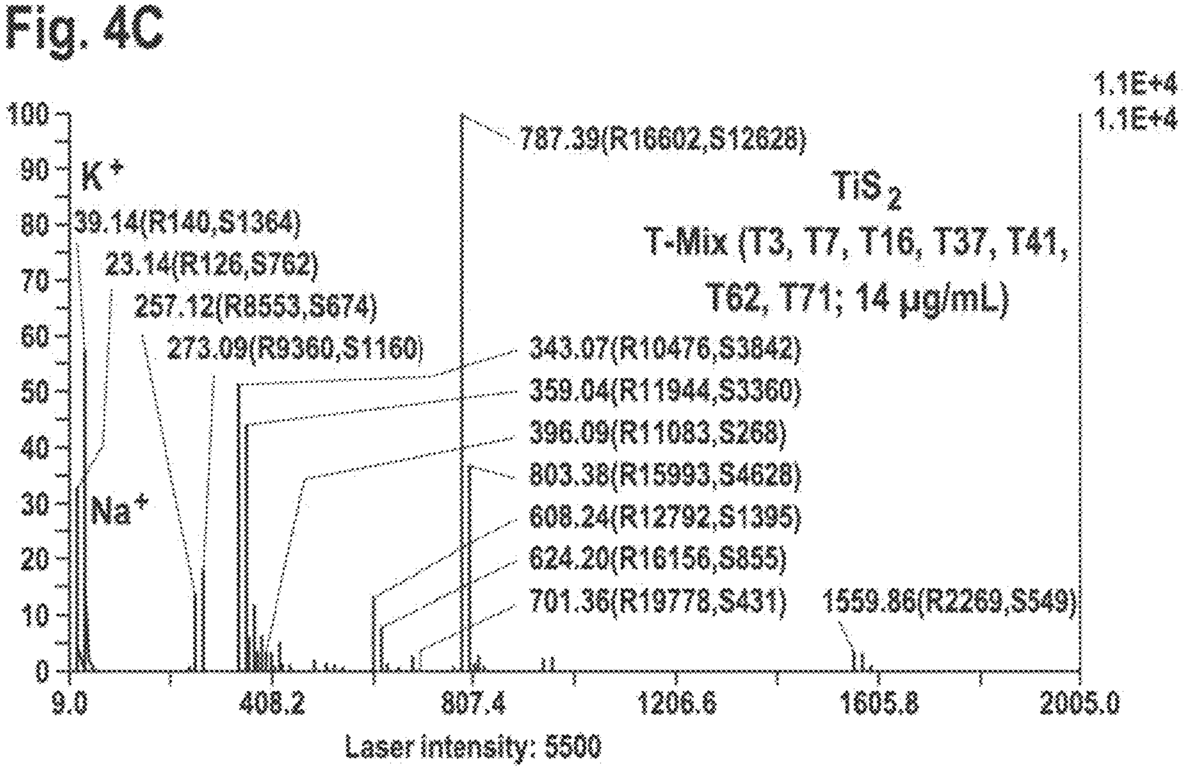
Figure 4D:
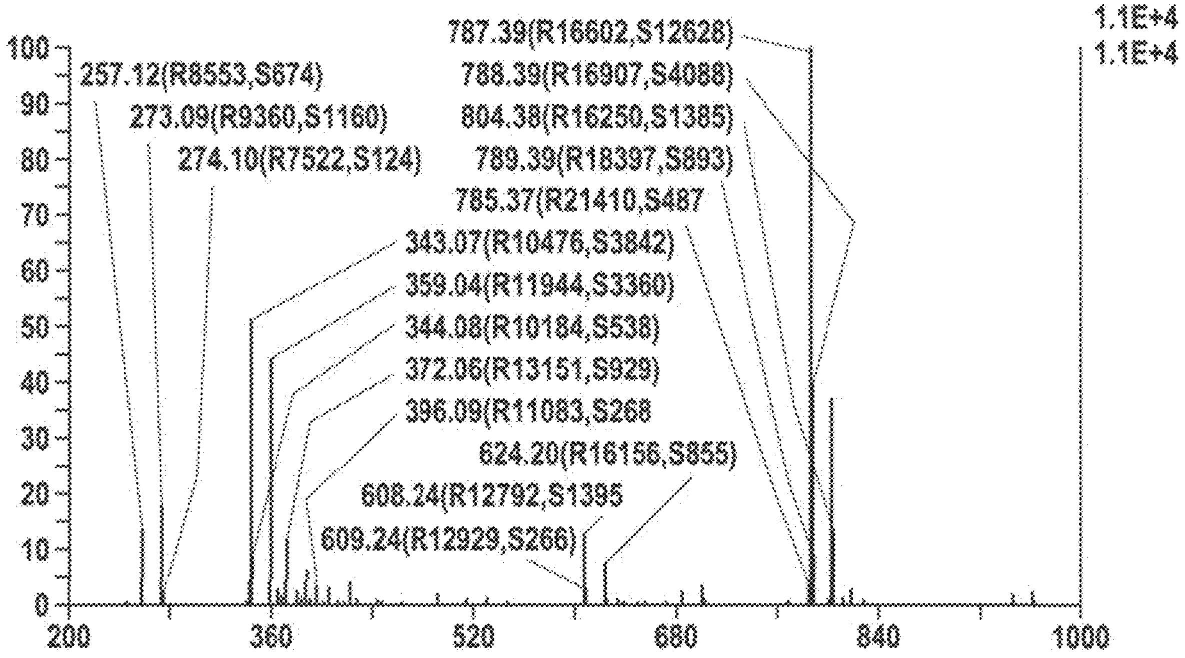

FIG. 4C and FIG. 4D show the relative intensity or absolute intensity as a function of the m/z of a mixture of seven therapeutically substances: T3, T7, T16, T37, T41, T62 and T71, each 14 μg/ml. The matrix is a bulk $TiS_2$ matrix. FIG. 4D is an enlargement of the MS spectrum of FIG. 4C in the m/z range of 200 to 1000. FIG. 4C and FIG. 4D demonstrate the desorption of the therapeutically substances T3, T7, T16, T37, T41, T62 and T71, and an ionization mainly by formation of the corresponding sodium adducts $[M+Na]^+$ with some analytes (T37, T16, T62, T71, T3) also forming potassium adducts $[M+K]^+$. Furthermore, no significant background signals can be observed.

Laser Desorption/Ionization on Sonicated Material:

The preparation of stable $MoS_2$ or $WS_2$ dispersions include weighing of a respective bulk $MoS_2$ or $WS_2$ material (particle size between 90 nm to 40 μm, preferably 6 μm for $MoS_2$ or 2 μm for $WS_2$), washing with $MeCN/H_2O=50/50$ and suspending in $MeCN/H_2O=50/50$ with a concentration between 3 mg/mL to 10 mg/mL, preferably 7 mg/mL. Subsequent ultrasonic treatment using an ultrasonic probe (200 W, 30 min, water bath) resulting in the formation of the respective $MoS_2$ or $WS_2$ dispersion. Residual bulk material is removed in a simple centrifugation (5000 rpm) step. The obtained dispersions can be used directly to coat a surface suitable for MALDI-MS measurement (commonly on a MALDI-steel-plate, ITO-glass slide, or similar) applying the dried-droplet method (preferably 2×0.7 μL). Subsequently after analyte deposition and air-drying, MALDI-TOF measurements are performed in positive mode adjusting the laser intensity to an optimal value of about 4500 units with a total of 2000 laser shots per spot. Analyte signals naturally occurred as alkali adducts ($[M+Na]^+$ and $[M+I(]^+$).

FIG. 5A to FIG. 5D and FIG. 6A to FIG. 6D show the MS spectra of a steroid mixture and therapeutically substance mixture, respectively, which results from the method according to the first aspect of the present invention by using different bulk inorganic matrices. In contrast to FIG. 1A to FIG. 1D, FIG. 2A to FIG. 2D, FIG. 3A to FIG. 3D, and FIG. 4A to FIG. 4D, the bulk material was additional ultrasonicated, e.g. by using a probe sonicator. As it can seen from FIG. 5A to FIG. 5D and FIG. 6A to FIG. 6D, the alkali ions $Na^+$ and $K^+$ can be directly detected via the method according to the first aspect of the present invention at m/z=23 and m/z=39, respectively.

Figure 5A:
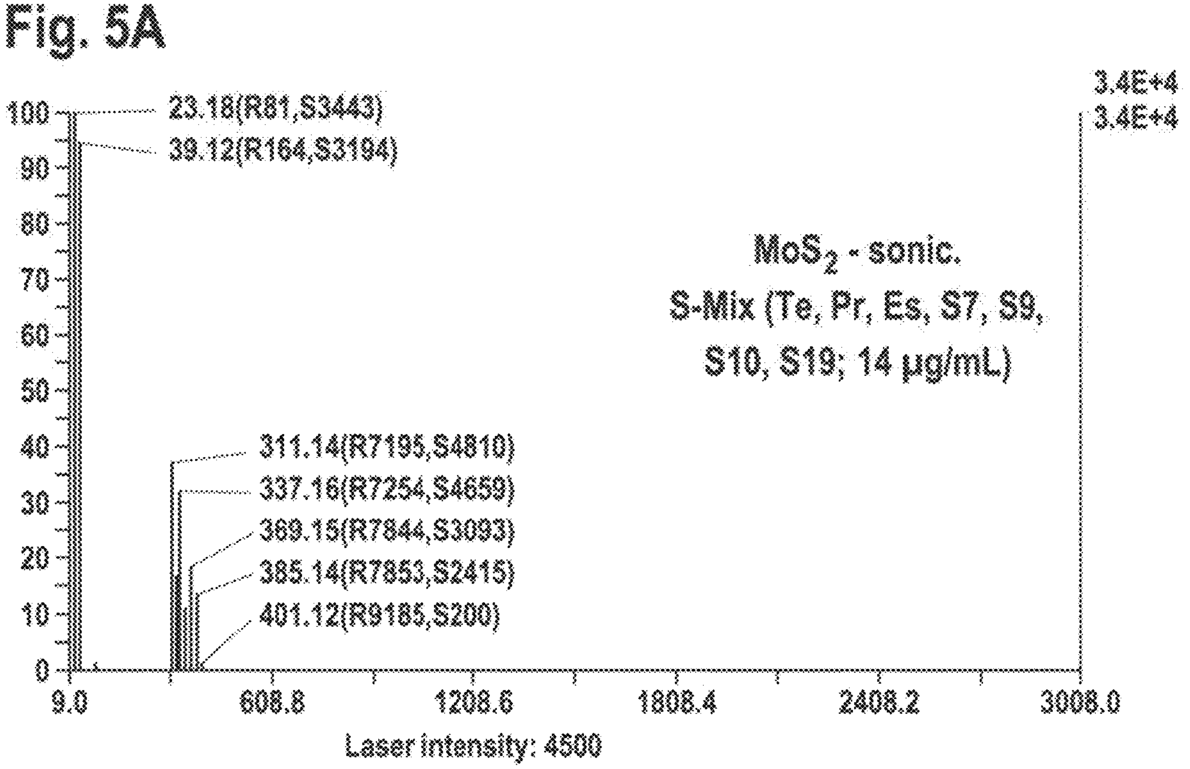
FIG. 5A to FIG. 5D show the MS spectra of a steroid mixture and therapeutically substance mixture, respectively.
Figure 5B:
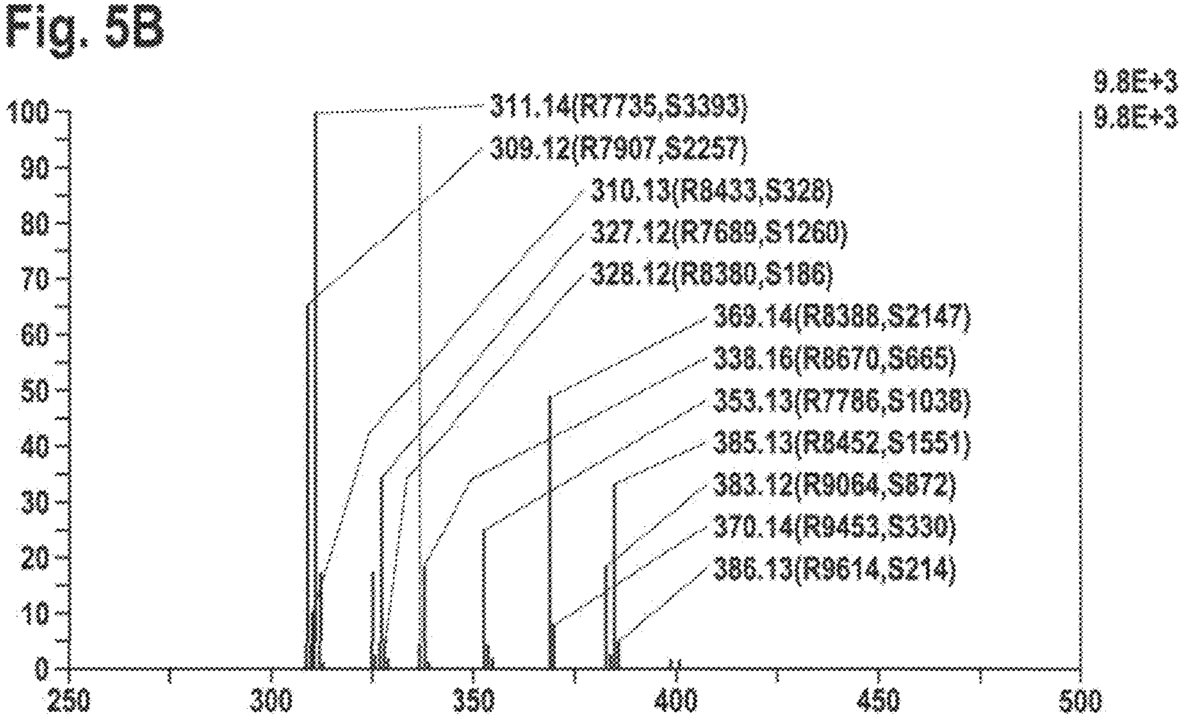

FIG. 5A and FIG. 5B show the relative intensity or absolute intensity as a function of the m/z of a steroid mixture comprising seven steroids: Te, Pr, Es, S7, S9, S10 and S19, each 14 μg/ml. The matrix is a bulk $MoS_2$ matrix having a particle size of about 6 μm, which was sonicated. FIG. 5B is an enlargement of the MS spectrum of FIG. 5A in the m/z range of 250 to 500. FIG. 5A and FIG. 5B demonstrate the desorption of the steroid analytes Te, Pr, S7, S9, S10 and S19, and an ionization mainly by formation of the corresponding sodium adducts $[M+Na]^+$ with also potassium adducts formation $[M+K]^+$. Furthermore, no significant background signals can be observed.

Figure 5C:
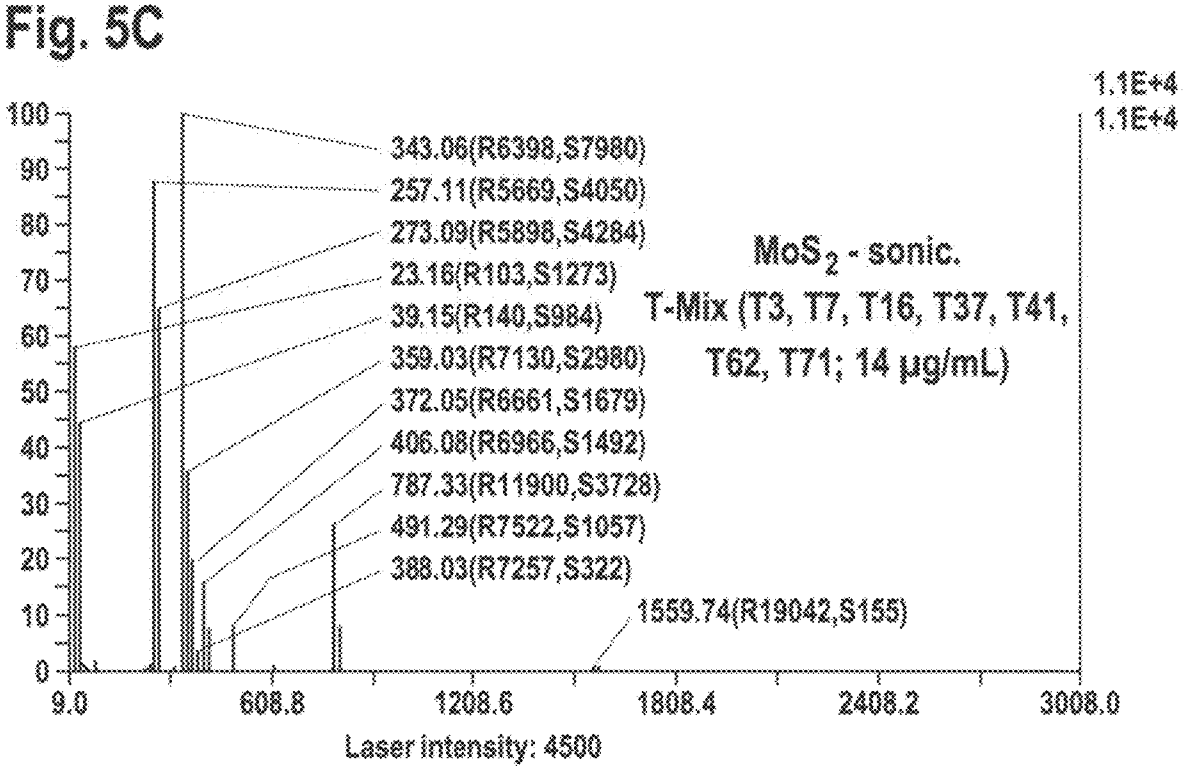
Figure 5D:
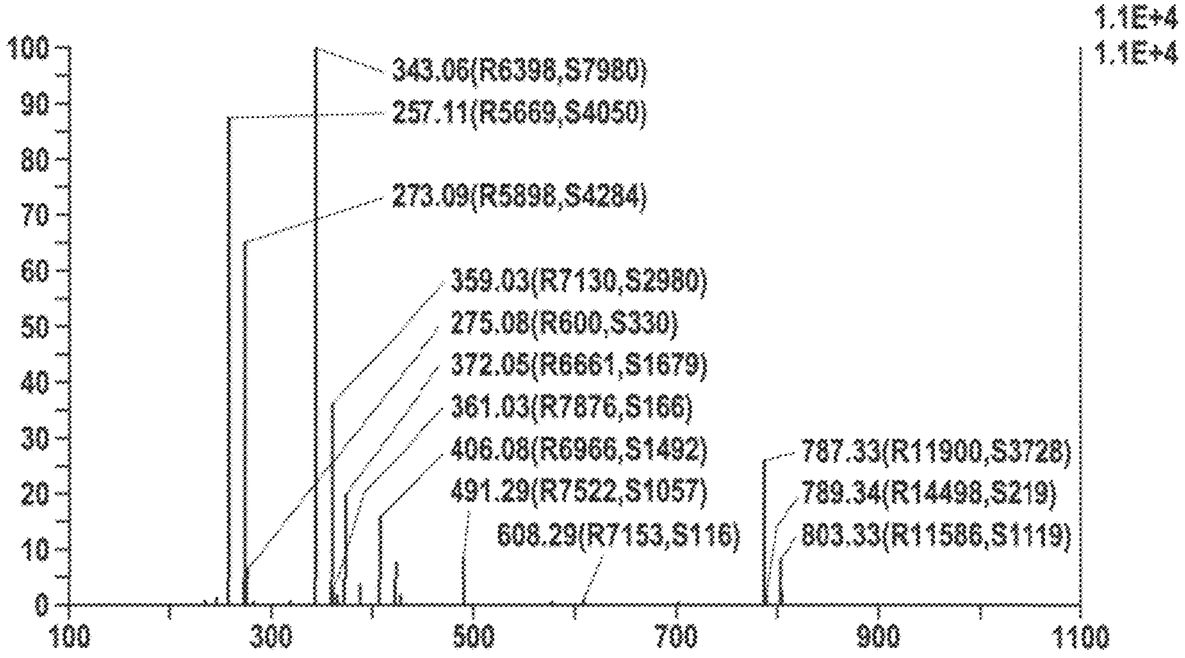

FIG. 5C and FIG. 5D show the relative intensity or absolute intensity as a function of the m/z of a mixture of seven therapeutically substances: T3, T7, T16, T37, T41, T62 and T71, each 14 μg/ml. The matrix is a bulk $MoS_2$ matrix having a particle size of about 6 μm, which was sonicated. FIG. 5D is an enlargement of the MS spectrum of FIG. 5C in the m/z range of 100 to 1100. FIG. 5C and FIG. 5D demonstrate the desorption of the therapeutically substances T3, T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 6A:
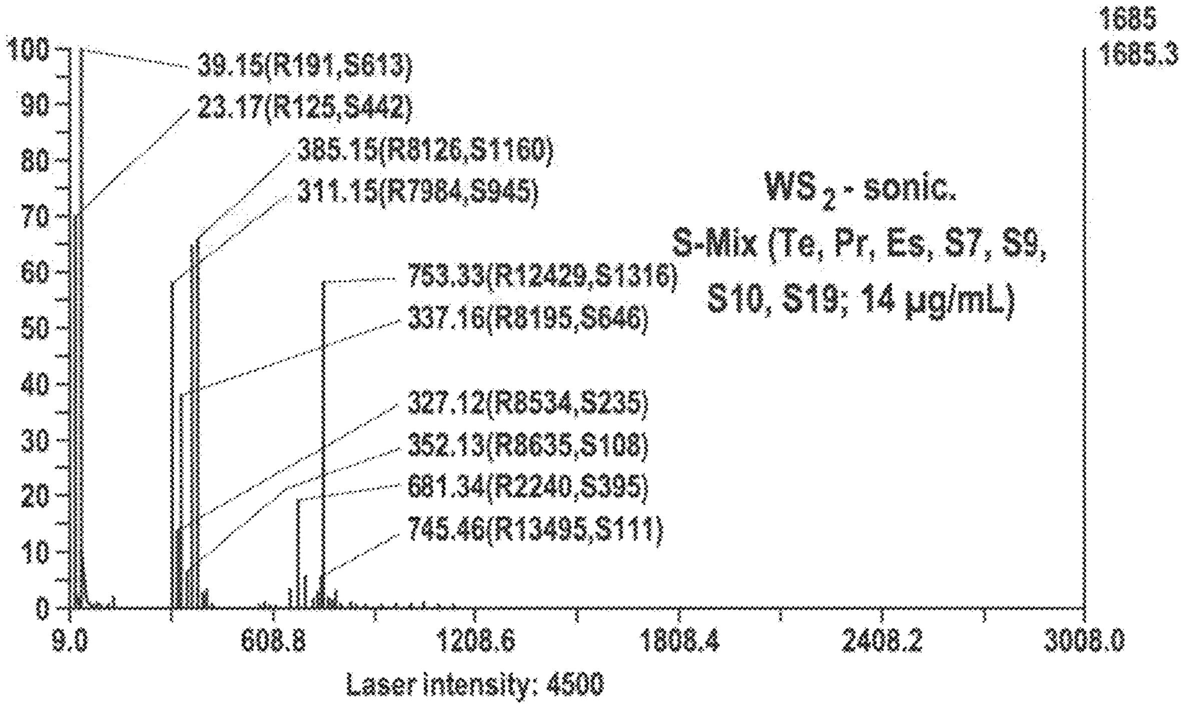
FIG. 6A to FIG. 6D show the MS spectra of a steroid mixture and therapeutically substance mixture, respectively.
Figure 6B:
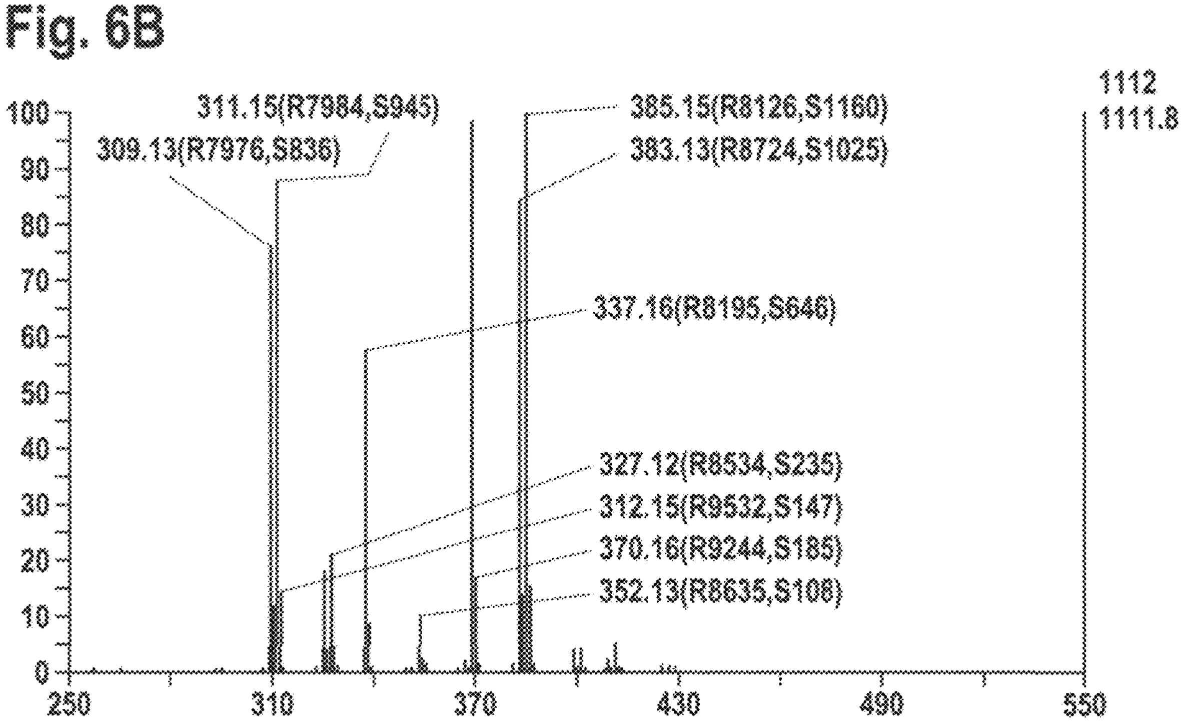

FIG. 6A and FIG. 6B show the relative intensity or absolute intensity as a function of the m/z of a steroid mixture comprising seven steroids: Te, Pr, Es, S7, S9, S10 and S19, each 14 μg/ml. The matrix is a bulk $WS_2$ matrix having a particle size of about 2 μm, which was sonicated. FIG. 6B is an enlargement of the MS spectrum of FIG. 6A in the m/z range of 250 to 550. FIG. 6A and FIG. 6B demonstrate the desorption of the steroid analytes Te, Pr, S7, S9, S10 and S19, and an ionization mainly by formation of the corresponding sodium adducts $[M+Na]^+$ with also the potassium adducts formation $[M+K]^+$ and multiple alkali adducts formation (e.g. m/z=753 $[S19-H+Na+K^+]$). Furthermore, no significant background signals can be observed.

Figure 6C:
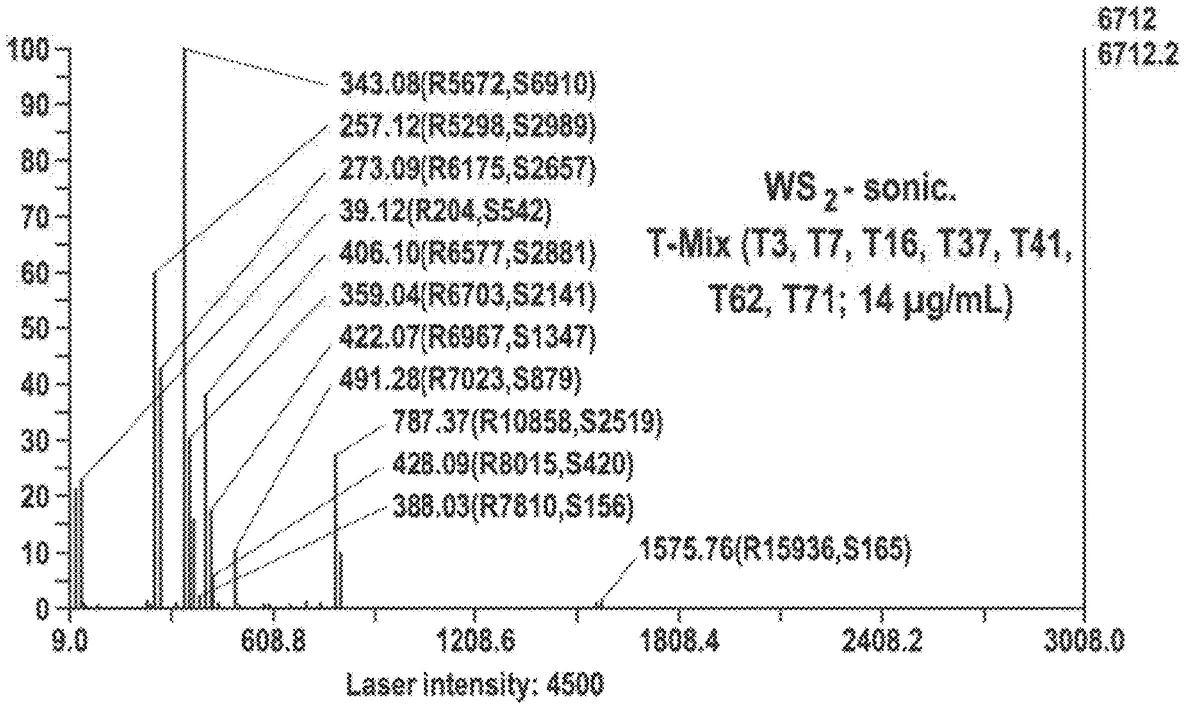
Figure 6D:
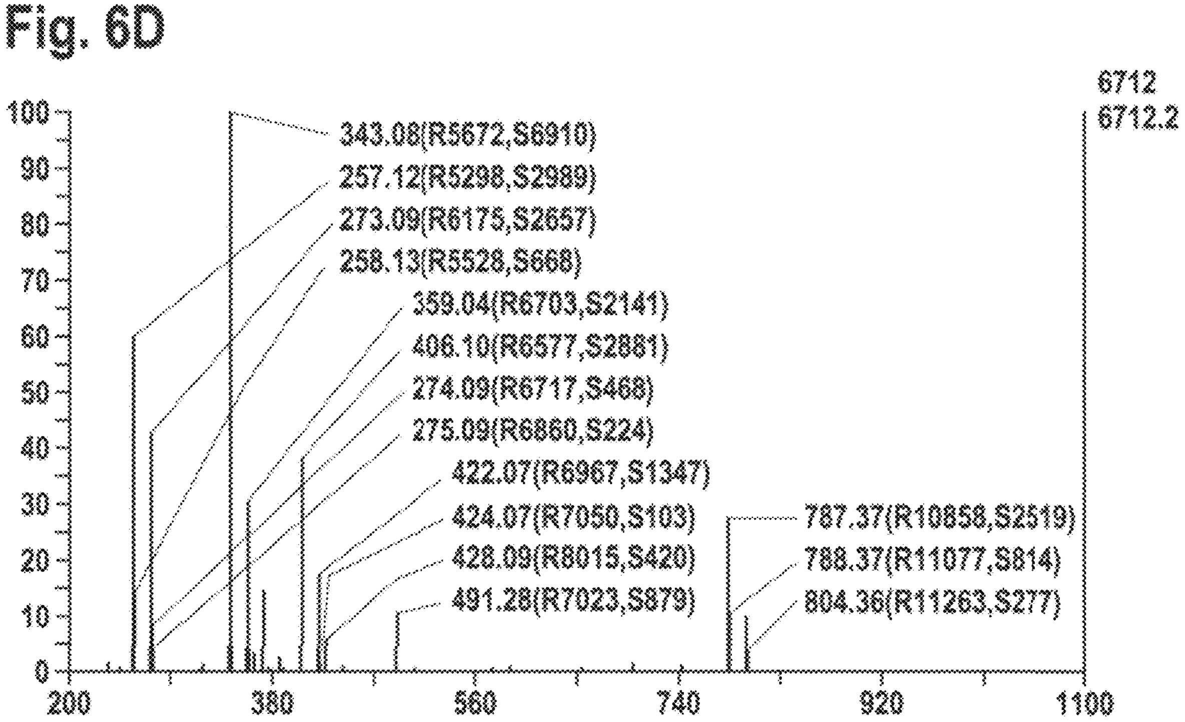

FIG. 6C and FIG. 6D show the relative intensity or absolute intensity as a function of the m/z of a mixture of seven therapeutically substances: T3, T7, T16, T37, T41, T62 and T71, each 14 μg/ml. The matrix is a bulk $WS_2$ matrix having a particle size of about 2 μm, which was sonicated. FIG. 6D is an enlargement of the MS spectrum of FIG. 6C in the m/z range of 200 to 1100. FIG. 6C and FIG. 6D demonstrate the desorption of the therapeutically substances T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 7:
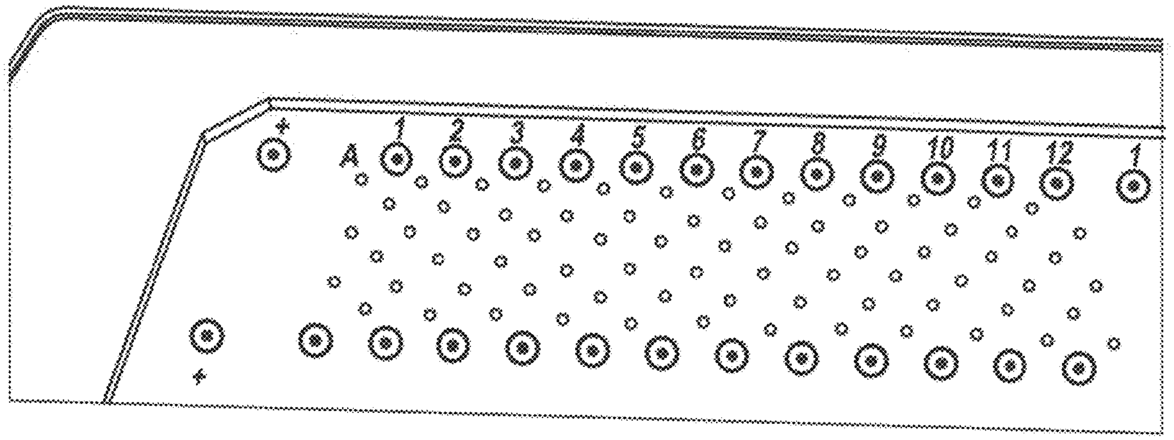
FIG. 7 shows a picture of a commercial available Indium-Tin-Oxide sample holder.

$MoS_2$ Coated on ITO-Glass Slide:

To demonstrate the universal application of the herein reported $MoS_2$ suspension and dispersion, a commercial available Indium-Tin-Oxide (ITO, see FIG. 7) coated microscopy glass slide is layered with the corresponding $MoS_2$-material, applying the dried-droplet method (preferably 2×0.7 μL). Subsequently after analyte deposition and air-drying, MALDI-TOF measurements are performed in positive mode adjusting the laser intensity to an optimal value of about 5500 units with a total of 2000 laser shots per spot. Analyte signals occurred as alkali adducts ($[M+Na]^+$ and [M+K]P).

Figure 8A:
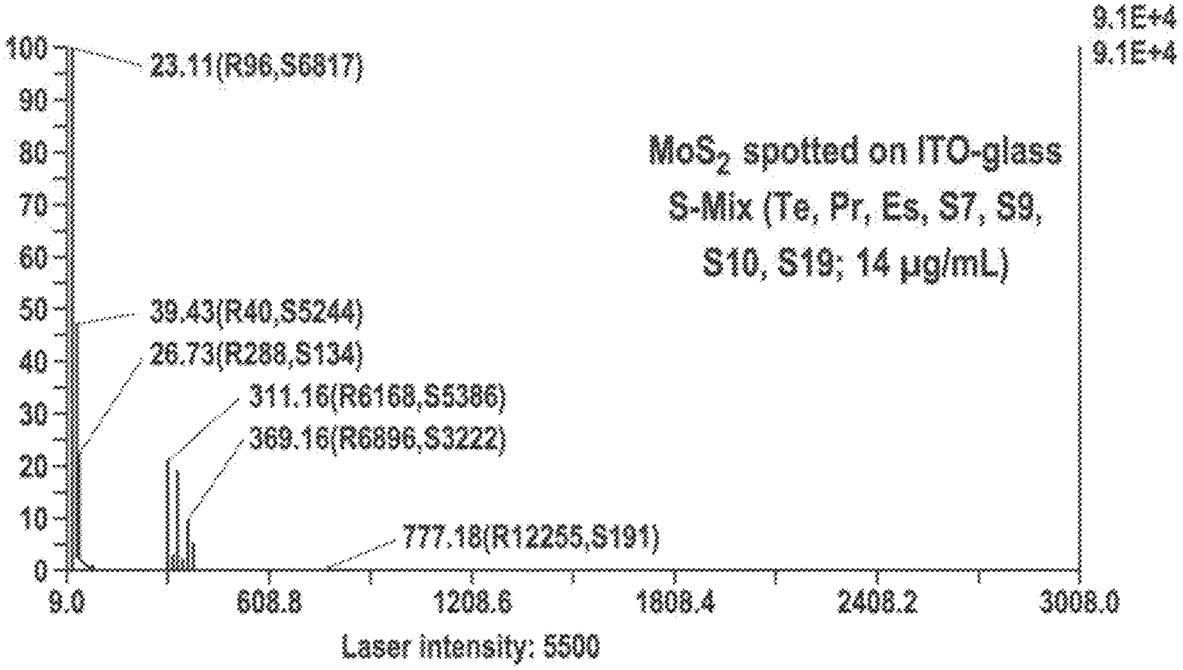
FIG. 8A to FIG. 8D show the MS spectra of a steroid mixture and therapeutically substance mixture coated on ITO glass slide as a sample holder, respectively.
Figure 8B:
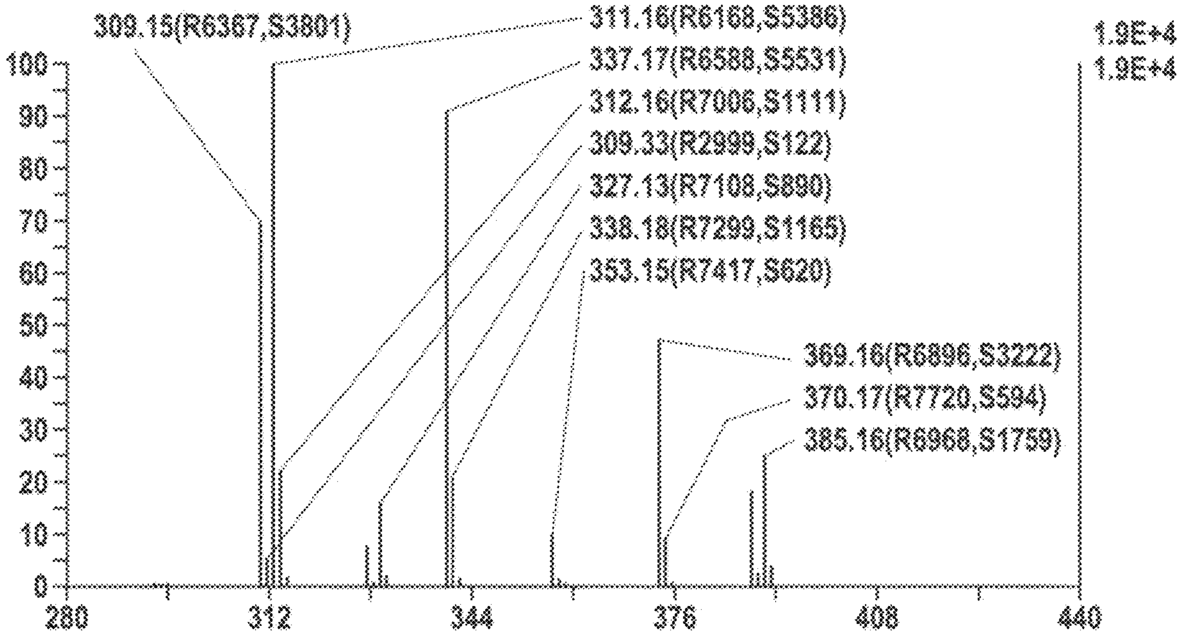

FIG. 8A and FIG. 8B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix coated on an ITO glass slide sample holder. FIG. 8B is an enlargement of the MS spectrum of FIG. 8A in the m/z range of 280 to 440. FIG. 8A and FIG. 8B demonstrate the desorption of the steroid analytes Te, Pr, S7, S9, S10 and S19, and an ionization mainly by formation of the corresponding sodium adducts $[M+Na]^+$ with also some potassium adducts formation $[M+K]^+$. Furthermore, no significant background signals can be observed.

Figure 8C:
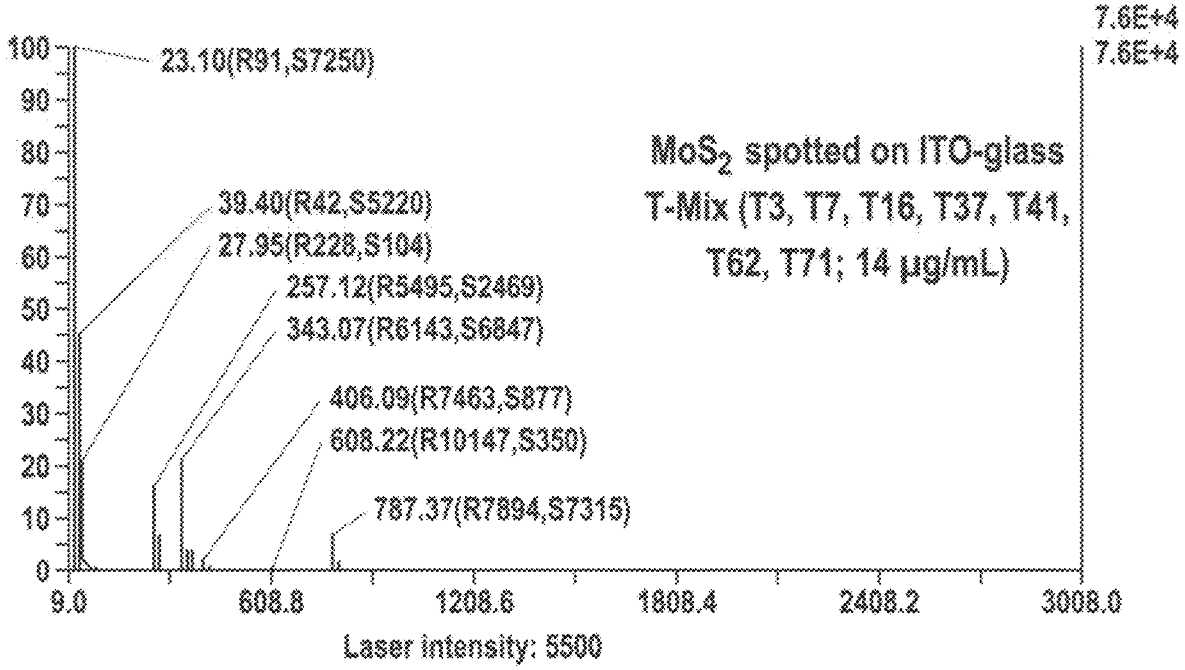
Figure 8D:
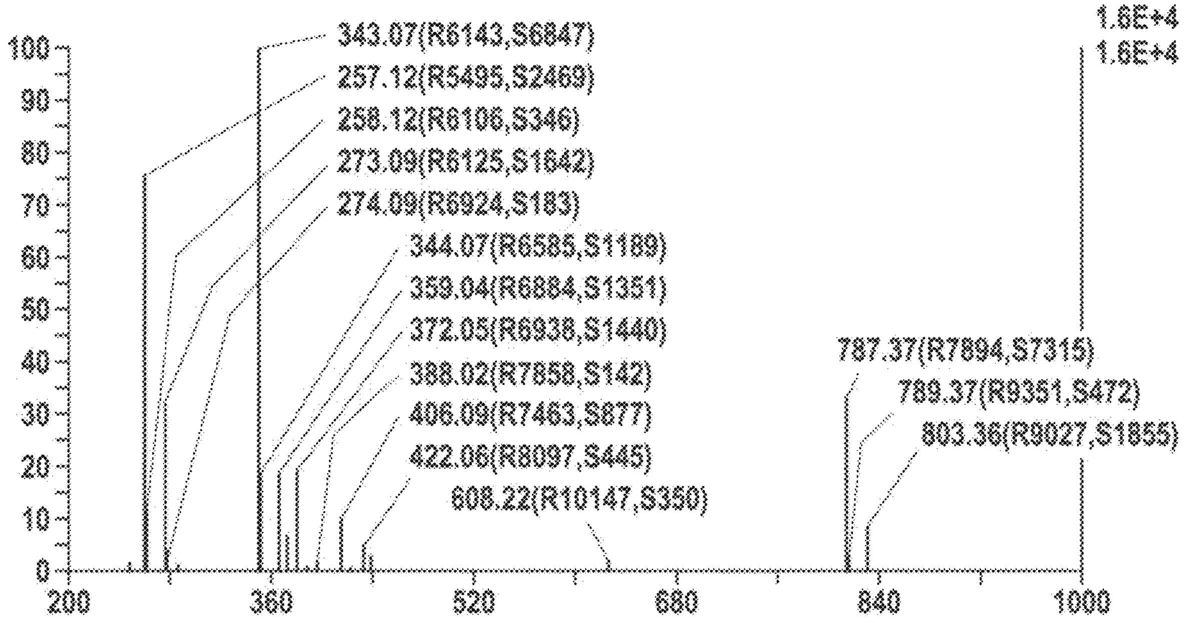

FIG. 8C and FIG. 8D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix coated on an ITO glass slide sample holder. FIG. 8D is an enlargement of the MS spectrum of FIG. 8C in the m/z range of 200 to 1000. FIG. 8C and FIG. 8D demonstrate the desorption of the therapeutically substances T3, T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 9A:
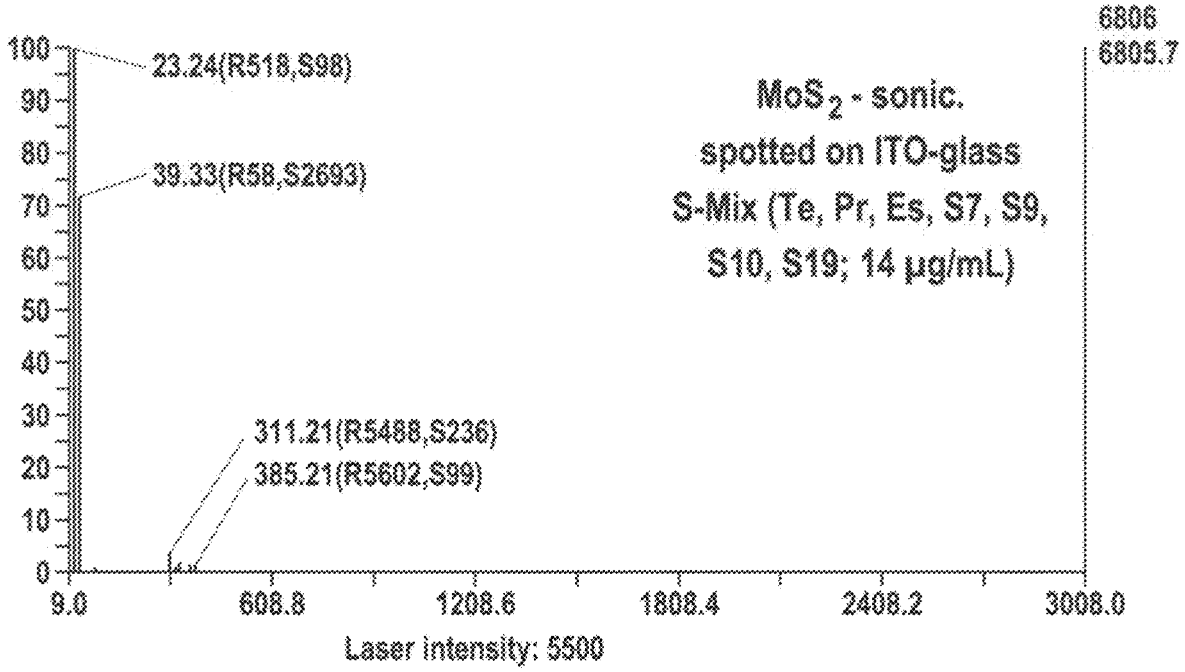
FIG. 9A to FIG. 9D show the MS spectra of a steroid mixture and therapeutically substance mixture coated on ITO glass slide as a sample holder, respectively.
Figure 9B:
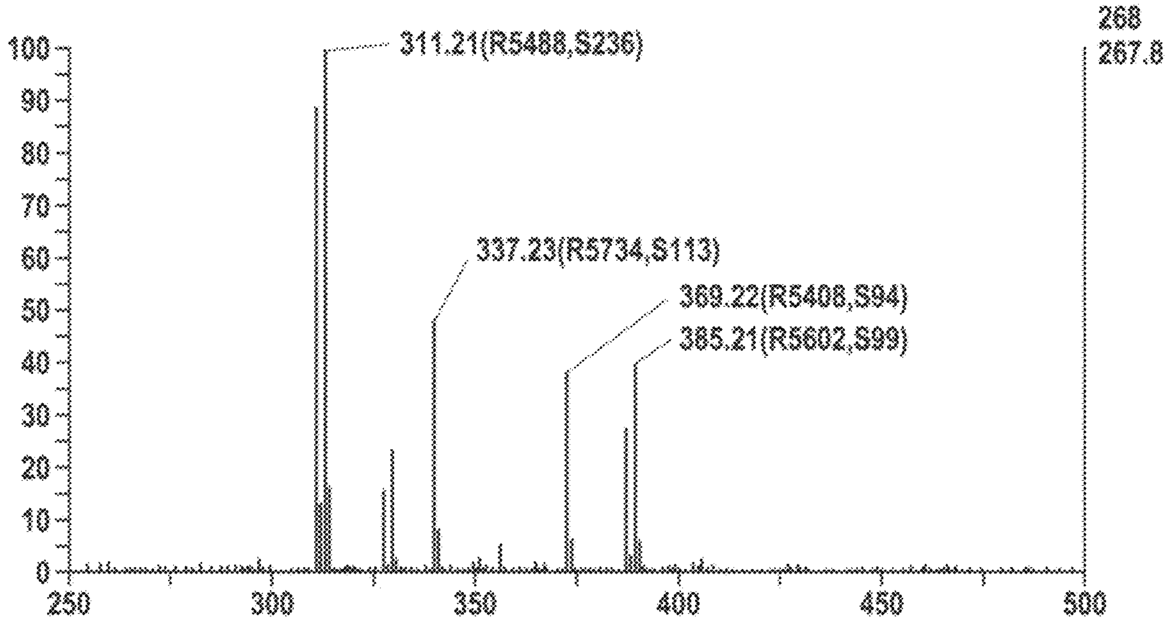

FIG. 9A and FIG. 9B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk sonicated $MoS_2$ matrix coated on an ITO glass slide sample holder. FIG. 9B is an enlargement of the MS spectrum of FIG. 9A in the m/z range of 250 to 500. FIG. 9A and FIG. 9B demonstrate the desorption of the steroid analytes Te, Pr, S7, S9, S10 and S19, and an ionization mainly by formation of the corresponding sodium adducts $[M+Na]^+$, with traces of some potassium adducts formation $[M+K]^+$. Furthermore, no significant background signals can be observed.

Figure 9C:
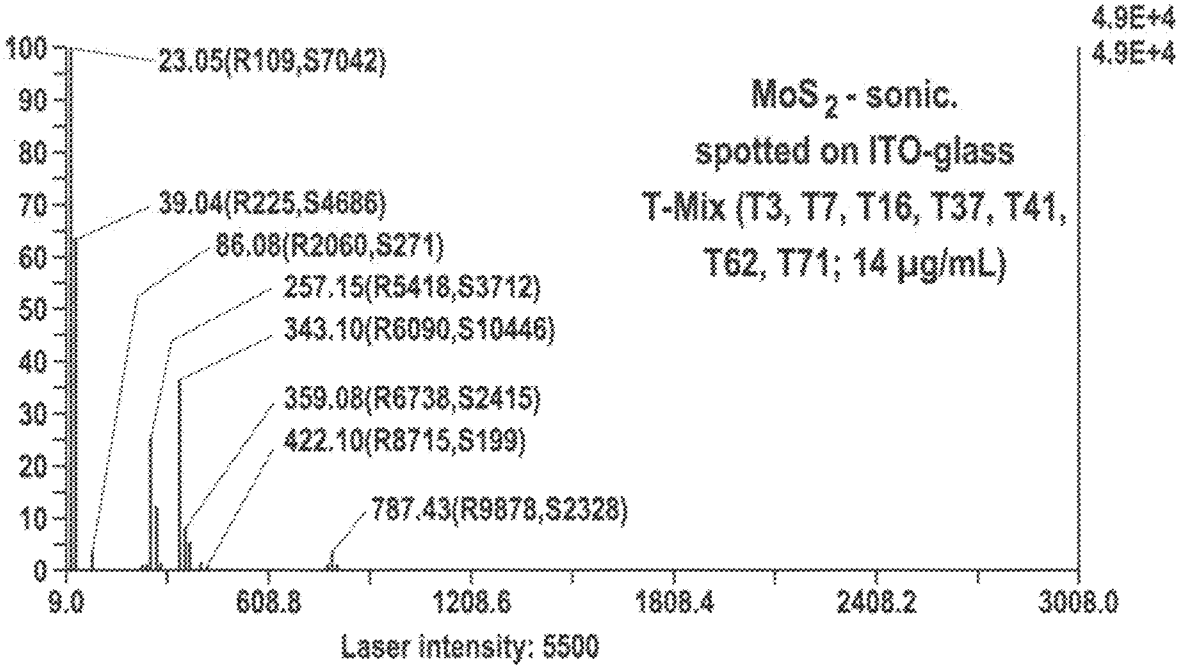
Figure 9D:
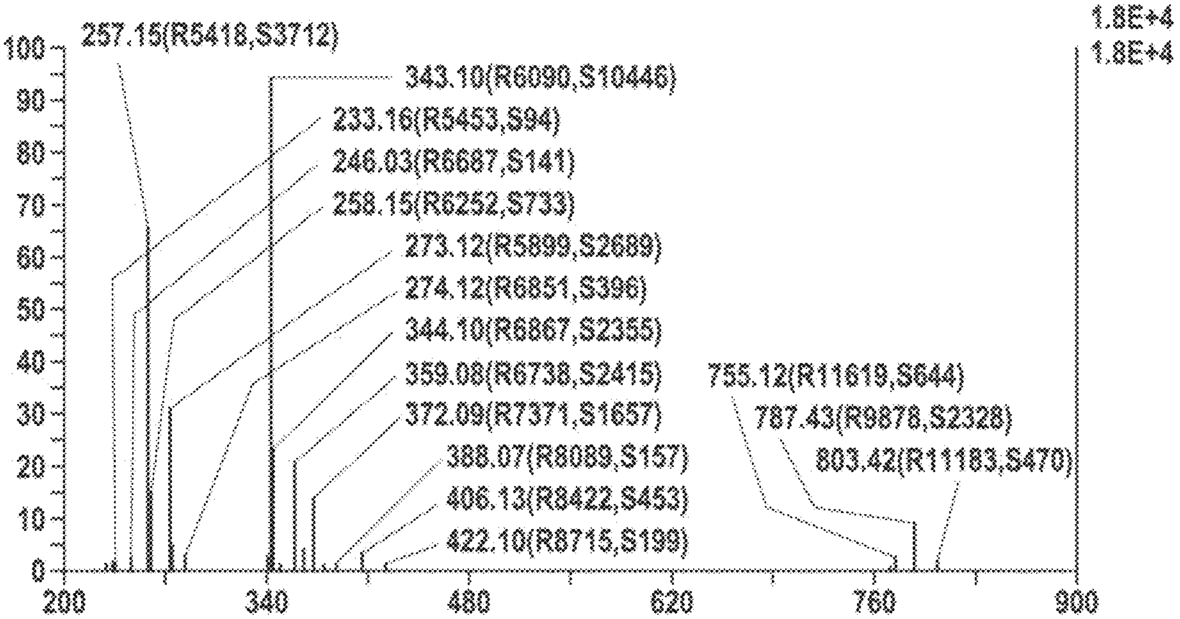

FIG. 9C and FIG. 9D show the relative intensity or absolute intensity as a function of the m/z of a mixture of seven therapeutically substances: T3, T7, T16, T37, T41, T62 and T71, each 14 μg/ml. The mixture of analytes is prepared on a bulk sonicated $MoS_2$ matrix coated on an ITO glass slide sample holder. FIG. 9D is an enlargement of the MS spectrum of FIG. 9C in the m/z range of 200 to 900. FIG. 9C and FIG. 9D demonstrate the desorption of the therapeutically substances T7, T16, T37, T41, T62 and T71, and an ionization mainly by formation of the corresponding sodium adducts $[M+Na]^+$ with some analytes (T37, T16, T62, T71) also forming potassium adducts $[M+K]^+$. Furthermore, no significant background signals can be observed.

Figure 10A:
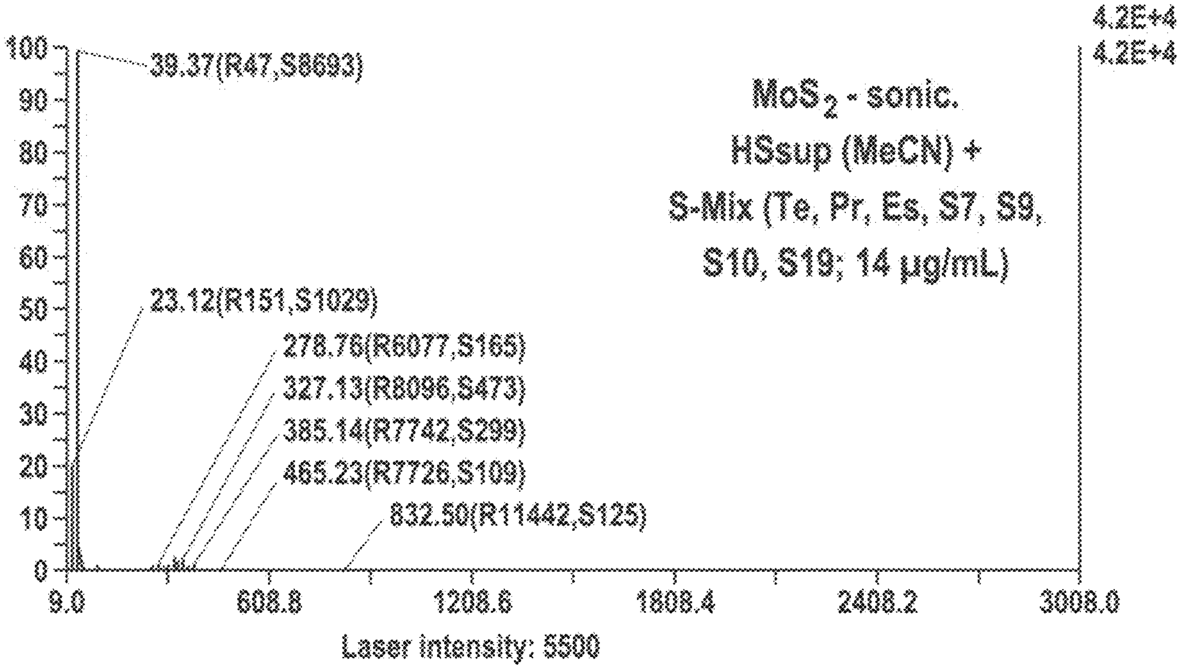
FIG. 10A to FIG. 10D show the MS spectra of a steroid mixture and therapeutically substance mixture coated on ITO glass slide as a sample holder, respectively.
Figure 10B:
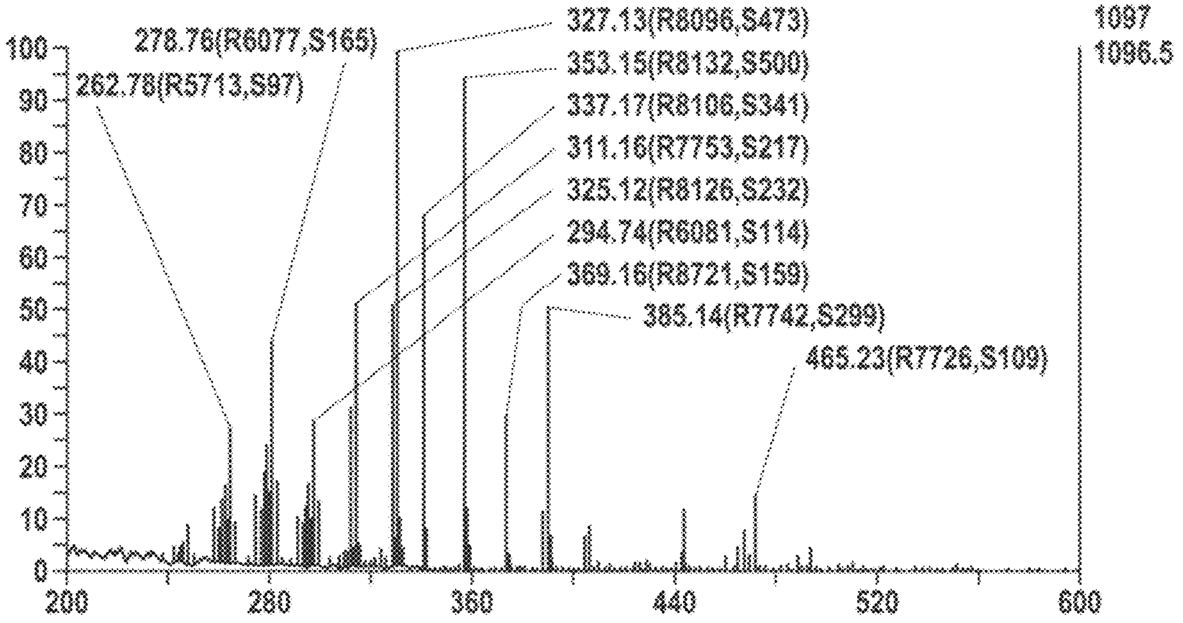

FIG. 10A and FIG. 10B show the relative intensity or absolute intensity as a function of the m/z of a steroid mixture comprising seven steroids: Te, Pr, Es, S7, S9, S10 and S19, each 1.4 μg/ml, in depleted horse serum. The mixture of analytes in depleted horse serum is prepared on a bulk sonicated $MoS_2$ matrix coated on an ITO glass slide sample holder. FIG. 10B is an enlargement of the MS spectrum of FIG. 10A in the m/z range of 200 to 600. FIG. 10A and FIG. 10B demonstrate the desorption of the steroid analytes Te, Pr, S7, S9, S10 and S19, and an ionization mainly by formation of the corresponding sodium adducts $[M+Na]^+$ with also some potassium adducts formation $[M+K]^+$. Some background signals can be observed, presumably originating from the depleted horse serum sample, especially in the range of m/z=260-300.

Figure 10C:
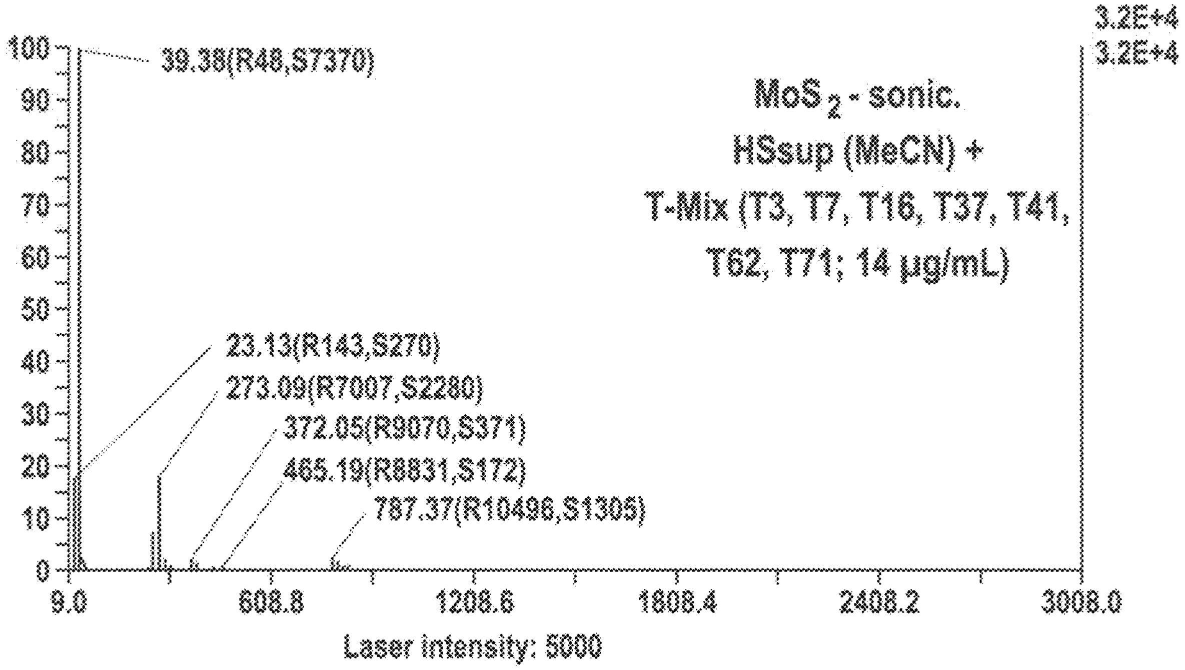
Figure 10D:
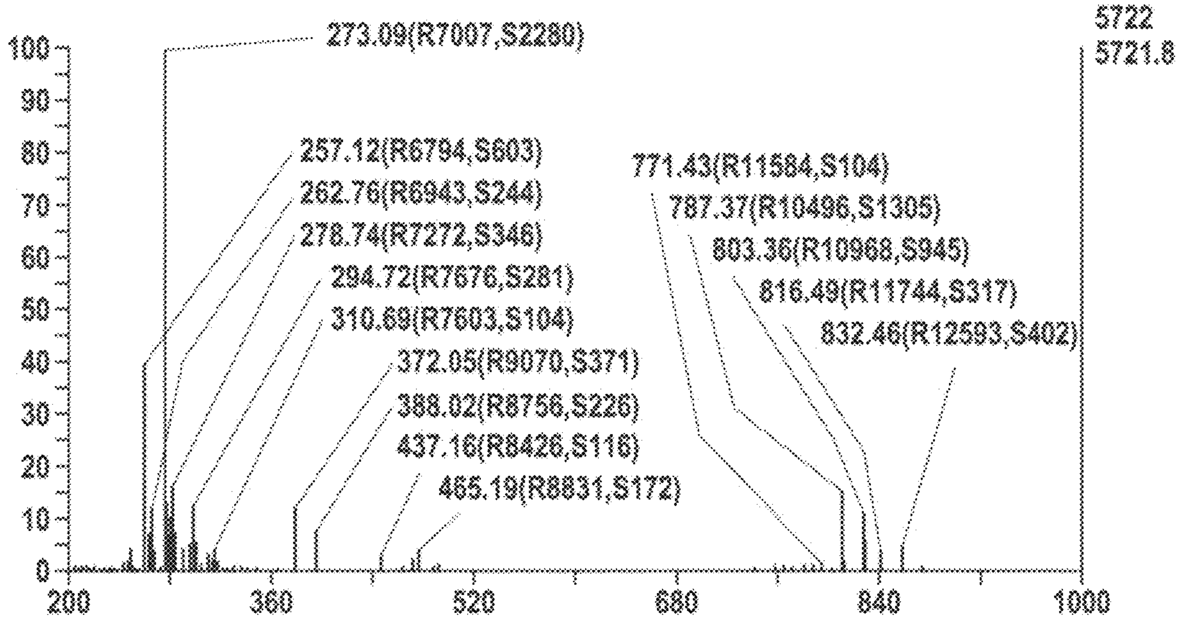

FIG. 10C and FIG. 10D show the relative intensity or absolute intensity as a function of the m/z of a mixture of seven therapeutically substances: T3, T7, T16, T37, T41, T62 and T71, each 1.4 μg/ml, in depleted horse serum. The mixture of analytes in in depleted horse serum is prepared on a bulk sonicated $MoS_2$ matrix coated on an ITO glass slide sample holder. FIG. 10D is an enlargement of the MS spectrum of FIG. 10C in the m/z range of 200 to 1000. FIG. 10C and FIG. 10D demonstrate the desorption of the therapeutically substances T7, T37, T41 and T62, T16 and T71, and an ionization by formation of the corresponding sodium adducts $[M+Na]^+$ with analytes (T37, T62, T41) also forming potassium adducts $[M+K]^+$. Some background signals can be observed, presumably originating from the depleted horse serum sample, especially in the range of m/z=230-320.

Figure 11A:
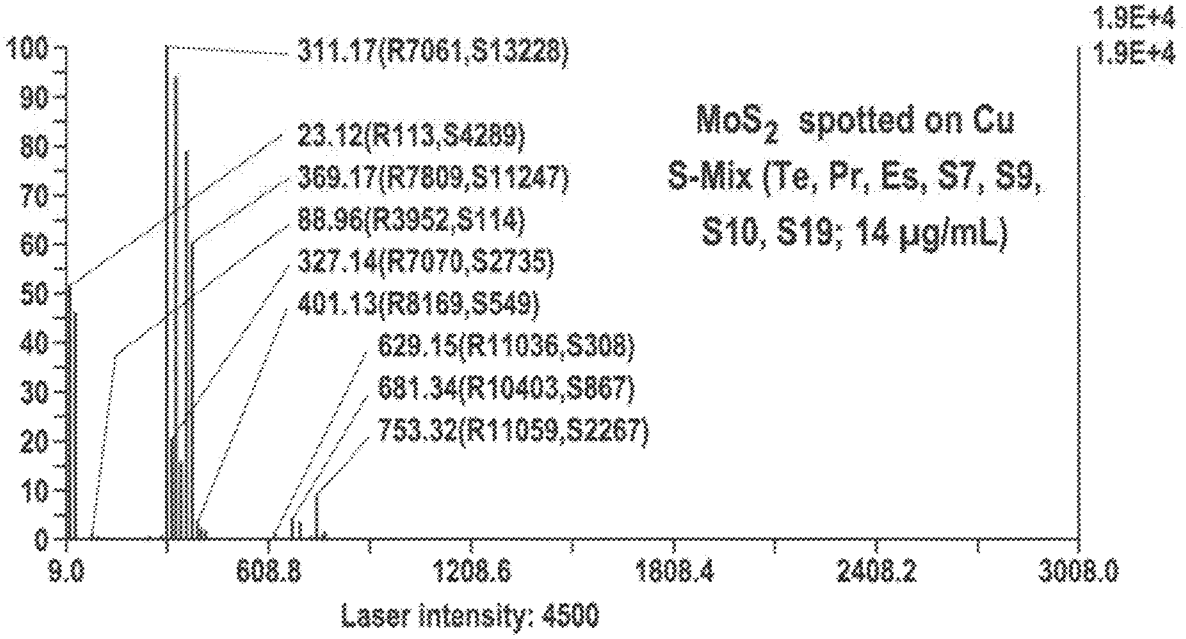
FIG. 11A to FIG. 11D show the MS spectra of a steroid mixture and therapeutically substance mixture coated on a copper conductive tape as a sample holder, respectively.
Figure 11B:
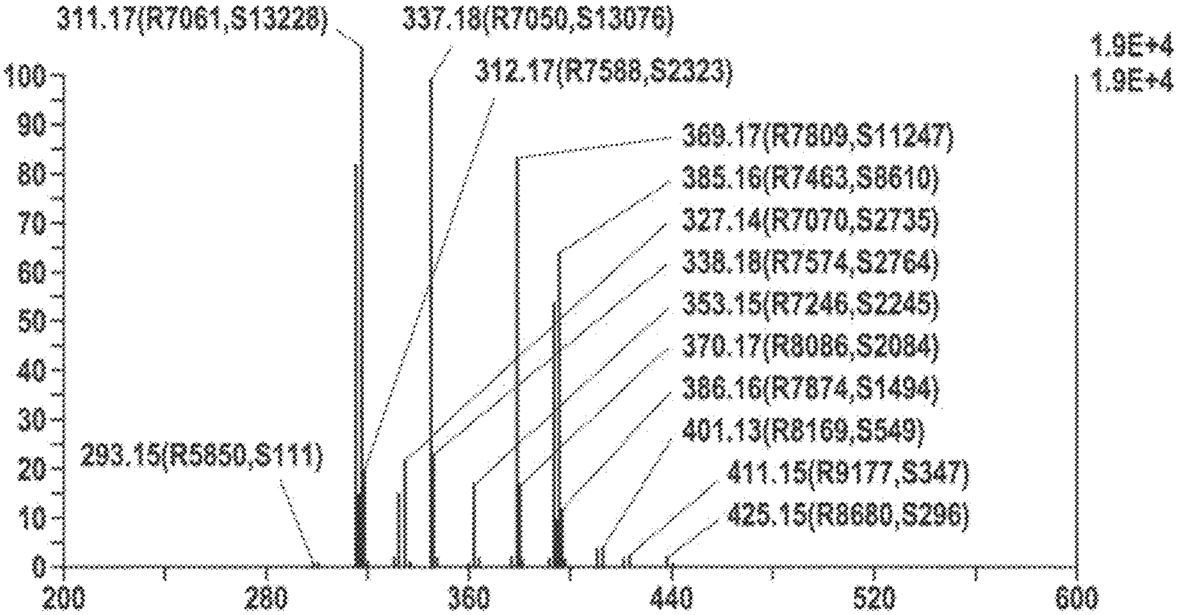

$MoS_2$ Coated on Copper Conductive Tape—Single Spots:

To demonstrate the universal application of the herein reported $MoS_2$ suspension, a commercial available copper conductive tape as a sample holder is layered with the corresponding $MoS_2$-material in single spots, applying the dried-droplet method (preferably 2×0.7 μL). Subsequently after analyte deposition and air-drying, MALDI-TOF measurements are performed in positive mode adjusting the laser intensity to an optimal value of about 4500 units with a total of 2000 laser shots per spot. Analyte signals occurred as alkali adducts ($[M+Na]^+$ and $[M+K]^+$). FIG. 11A and FIG. 11B demonstrate the desorption of the steroid analytes Es, Te, Pr, S7, S9, S10 and S19, and an ionization mainly by formation of the corresponding sodium adducts $[M+Na]^+$, with some potassium adducts formation $[M+K]^+$ and also some multiple alkali adducts formation (e.g. m/z=753 [S19-H+Na+K]$^+$). Furthermore, no significant background signals can be observed.

FIG. 11A and FIG. 11B show the relative intensity or absolute intensity as a function of the m/z of a steroid mixture comprising seven steroids: Te, Pr, Es, S7, S9, S10 and S19, each 14 μg/ml. The mixture of analytes is prepared as a single spot on a large bulk $MoS_2$ matrix coated on a copper conductive tape as a sample holder. FIG. 11B is an enlargement of the MS spectrum of FIG. 11A in the m/z range of 200 to 600.

Figure 11C:
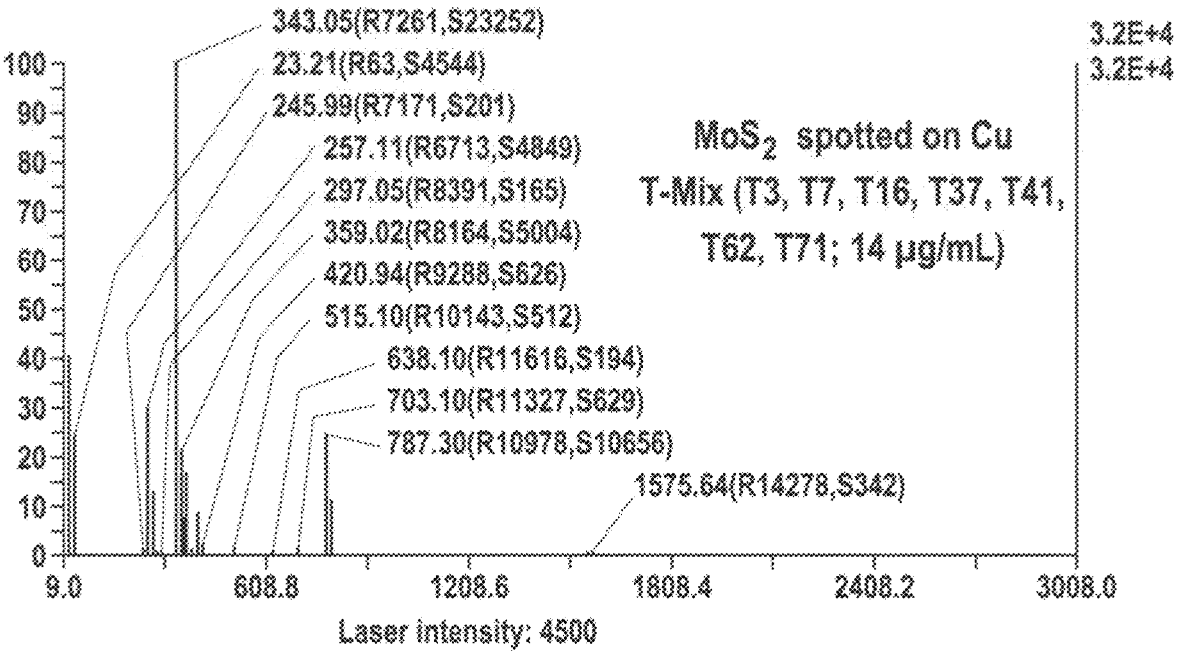
Figure 11D:
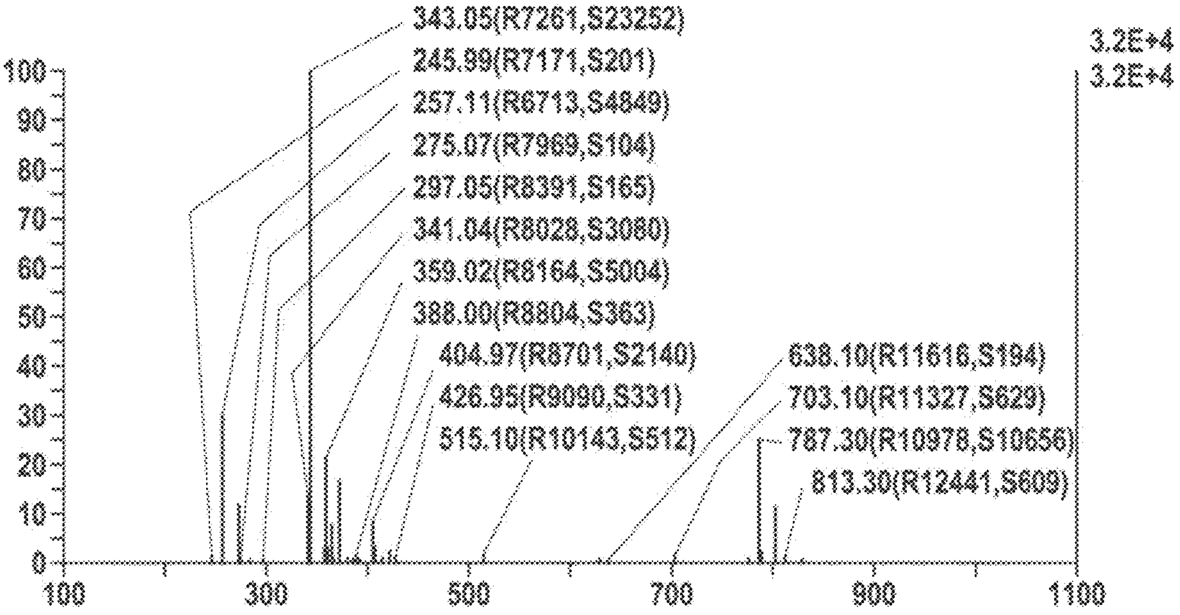

FIG. 11C and FIG. 11D show the relative intensity or absolute intensity as a function of the m/z of a mixture of seven therapeutically substances: T3, T7, T16, T37, T41, T62 and T71, each 14 μg/ml. The mixture of analytes is prepared as a single spot on a bulk $MoS_2$ matrix coated on a copper conductive tape as a sample holder. FIG. 11D is an enlargement of the MS spectrum of FIG. 11C in the m/z range of 100 to 1100. FIG. 11C and FIG. 11D demonstrate the desorption of the therapeutically substances T7, T16, T37, T41, T62 and T71, and an ionization mainly by formation of the corresponding sodium adducts [M+Na]$^+$ with some analytes (T37, T16, T62, T71, T41) also forming potassium adducts [M+K]$^+$. Furthermore, no significant background signals can be observed.

$MoS_2$ Coated on Copper Conductive Tape—Whole Area:

To demonstrate the universal application of the herein reported $MoS_2$ dispersion, the whole surface of a commercial available copper conductive tape as the sample holder is layered with the corresponding $MoS_2$-material. Therefore, the surface gets fully wetted with the $MoS_2$-dispersion, followed by complete evaporation under reduced pressure. Subsequently after analyte deposition and air-drying, MALDI-TOF measurements are performed in positive mode adjusting the laser intensity to an optimal value of about 4500 units with a total of 2000 laser shots per spot. Analyte signals occurred as alkali adducts ([M+Na]$^+$ and [M+K]$^+$).

Figure 12A:
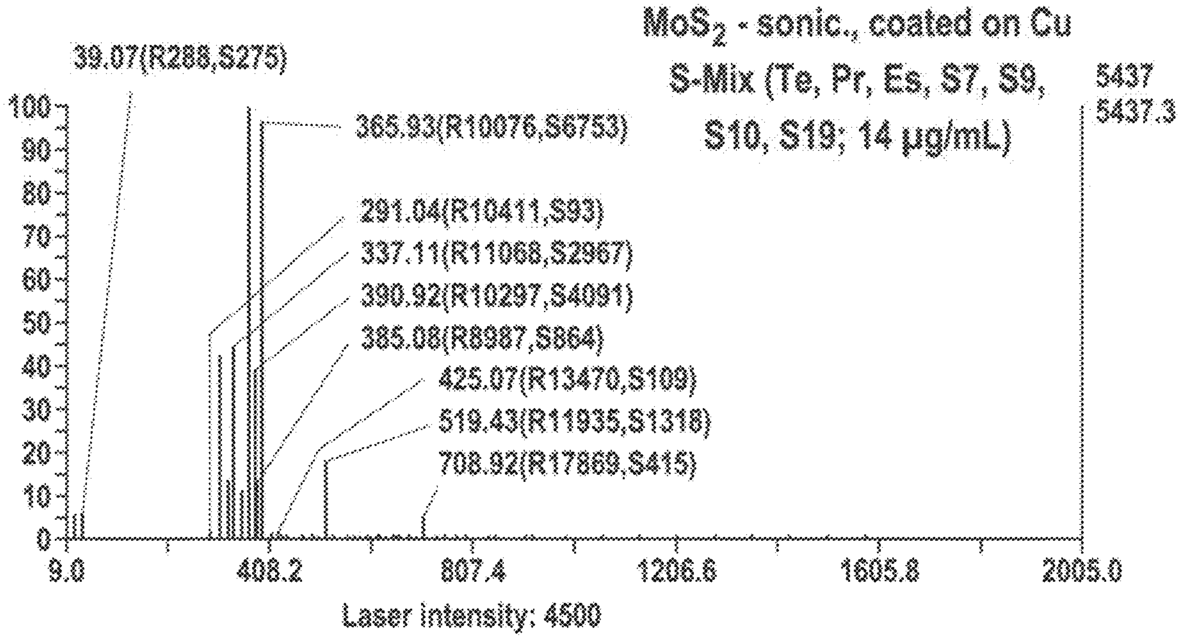
FIG. 12A to FIG. 12D show the MS spectra of a steroid mixture and therapeutically substance mixture coated on a copper conductive tape as a sample holder, respectively.
Figure 12B:
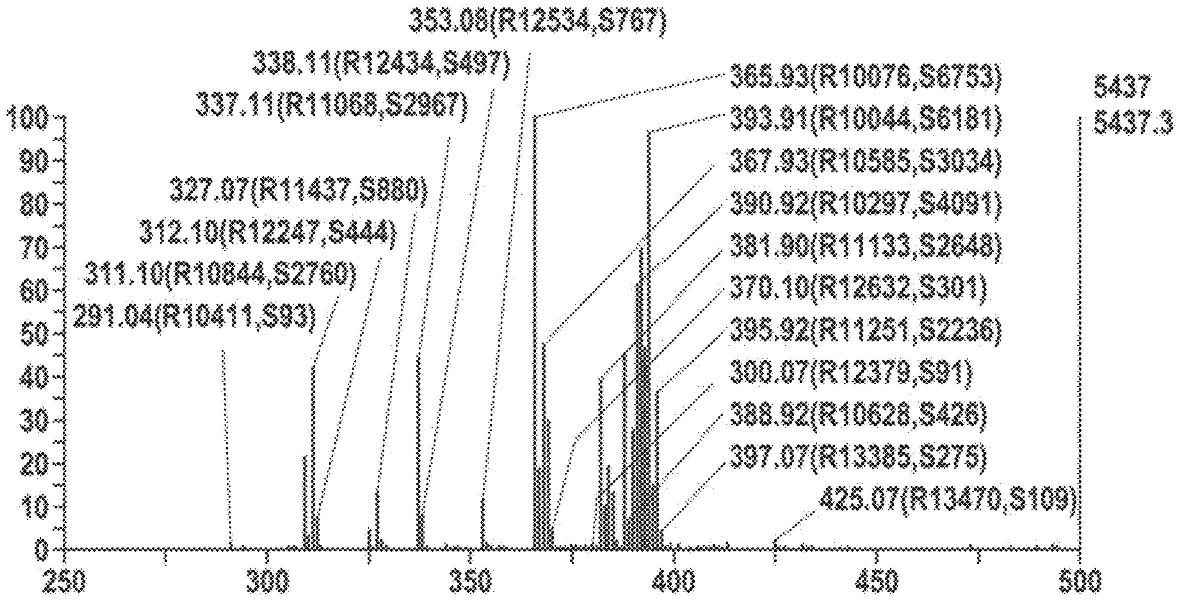

FIG. 12A and FIG. 12B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk sonicated $MoS_2$ matrix coated on the whole copper conductive tape area as a sample holder. FIG. 12B is an enlargement of the MS spectrum of FIG. 12A in the m/z range of 250 to 500. FIG. 12A and FIG. 12B demonstrate the desorption of the steroid analytes Te, Pr, S7, S9, S10 and S19. The ionization mainly occurred by formation of the corresponding sodium adducts [M+Na]$^+$, with traces of potassium adducts formation [M+K]$^+$. Some background signals can be observed, especially in the range of m/z=360-400.

Figure 12C:
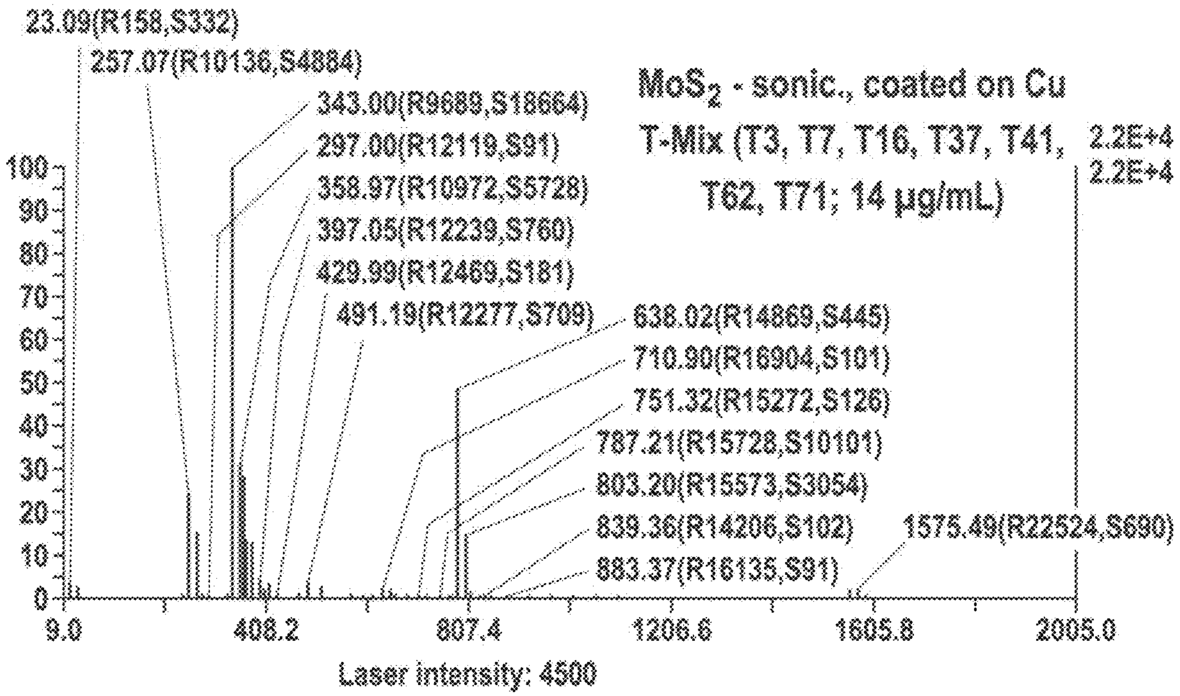
Figure 12D:
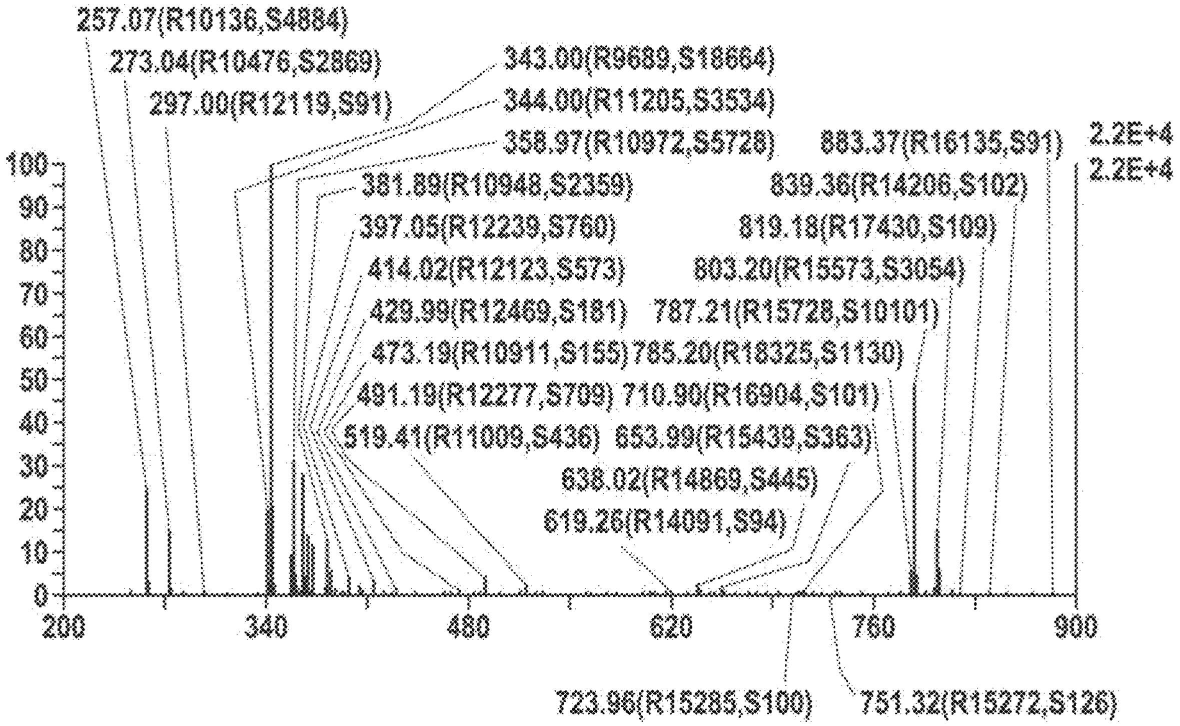

FIG. 12C and FIG. 12D show the relative intensity or absolute intensity as a function of the m/z of a mixture of seven therapeutically substances: T3, T7, T16, T37, T41, T62 and T71, each 14 μg/ml. The mixture of analytes is prepared on a bulk sonicated $MoS_2$ matrix coated on the whole copper conductive tape area as a sample holder. FIG. 12D is an enlargement of the MS spectrum of FIG. 12C in the m/z range of 200 to 900. FIG. 12C and FIG. 12D demonstrate the desorption of the therapeutically substances T7, T16, T37, T41 and T62. The ionization mainly occurred by formation of the corresponding sodium adducts [M+Na]$^+$ with some analytes (T37, T16) also forming potassium adducts [M+K]$^+$. Some background signals can be observed, especially in the range of m/z=360-430.

Control Experiment

To verify, that the desorption/ionization mechanism is based on the herein described $MoS_2$-surface, analytes are tested on the bare MALDI steel plate or bare ITO-glass slide. No detection of analytes are occurring. Additionally, a pure $MoS_2$-surface without loading of analyte molecules also does not lead to significant detection of background signals.

Figure 13A:
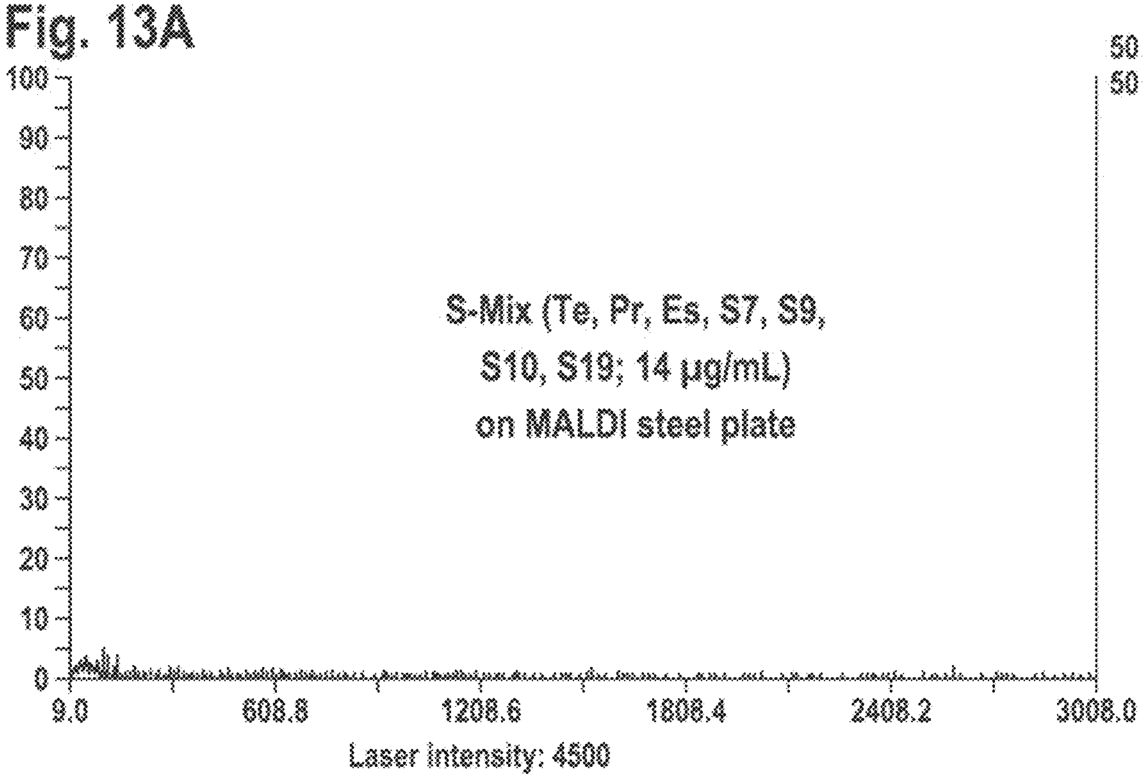
FIG. 13A and FIG. 13B show the MS spectra of control experiments.
Figure 13B:
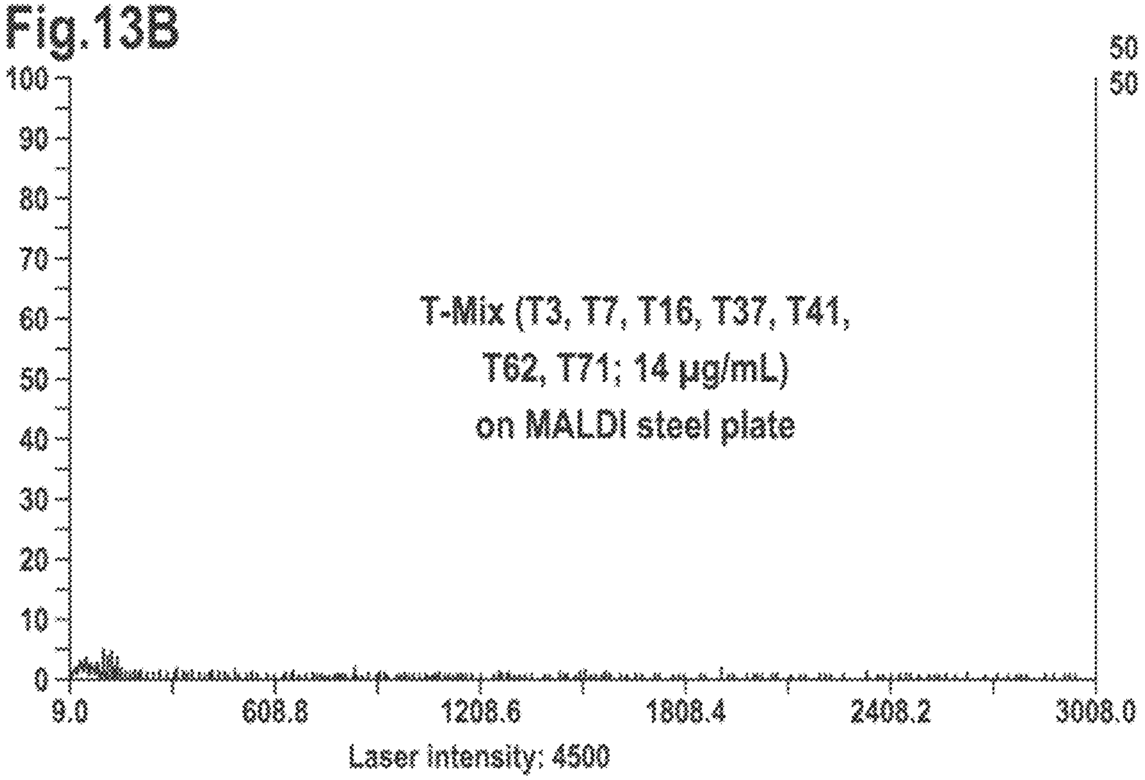

FIG. 13A and FIG. 13B show the relative intensity or absolute intensity as a function of the m/z of a steroid mixture comprising seven steroids: Te, Pr, Es, S7, S9, S10 and 519, each 14 μg/ml, and a mixture of seven therapeutically substances: T3, T7, T16, T37, T41, T62 and T71, each 14 μg/ml, respectively. The mixture of analytes is prepared on a MALDI steel plate as a sample holder without a matrix. There can be no signal detected by missing the matrix.

Figure 14:
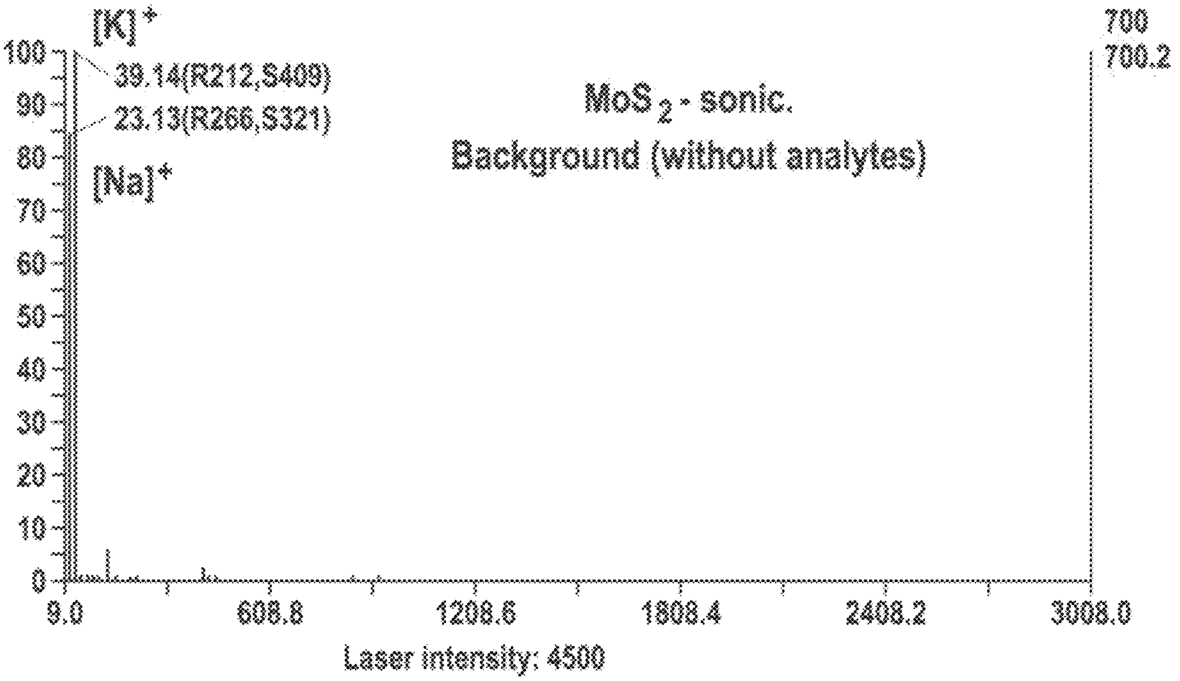
FIG. 14 shows the MS spectra of control experiments.

FIG. 14 shows the relative intensity or absolute intensity as a function of the m/z of a bulk sonicated $MoS_2$ matrix without analytes. There can be no signal detected by missing the analyte or mixtures of analytes.

Figure 15A:
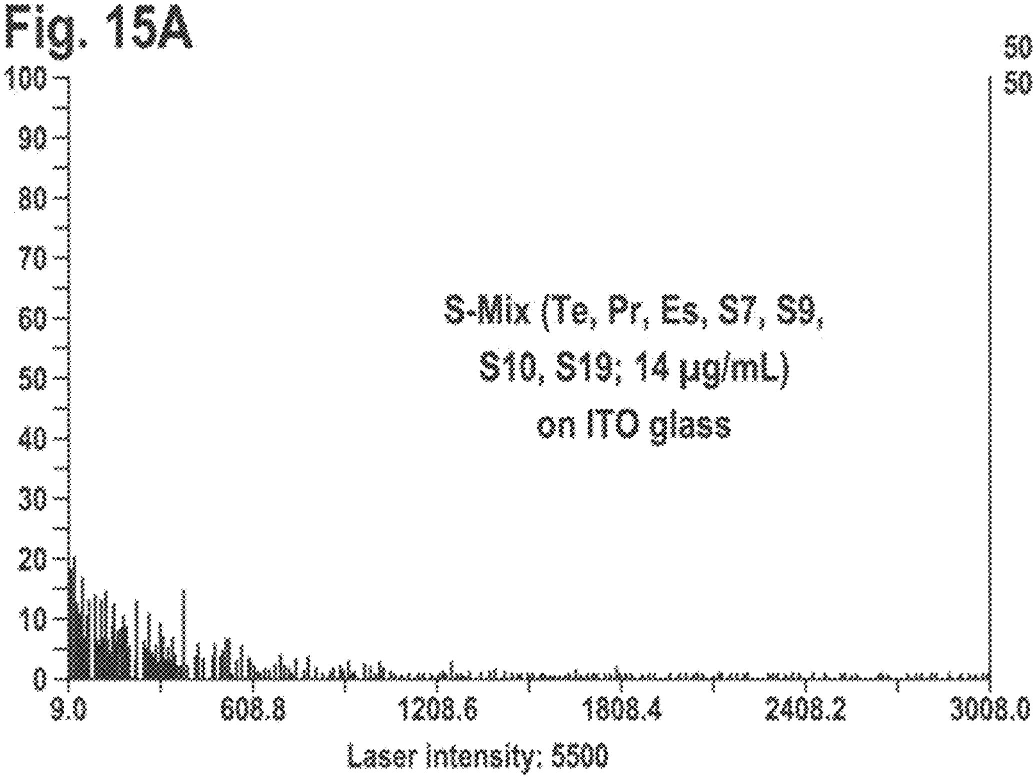
FIG. 15A and FIG. 15B show the MS spectra of control experiments.
Figure 15B:
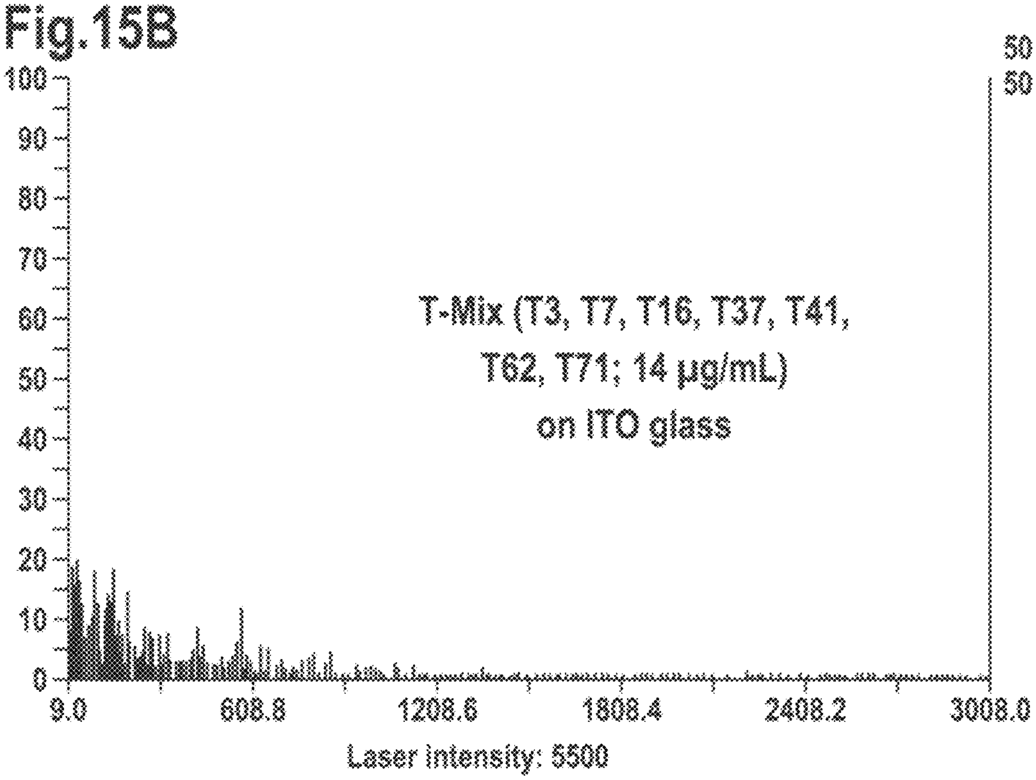

FIG. 15A and FIG. 15B show the relative intensity or absolute intensity as a function of the m/z of a steroid mixture comprising seven steroids: Te, Pr, Es, S7, S9, S10 and 519, each 14 μg/ml, and a mixture of seven therapeutically substances: T3, T7, T16, T37, T41, T62 and T71, each 14 μg/ml, respectively. The mixture of analytes is prepared on a blank ITO-glass slide as a sample holder without an matrix. There can be just basic background noise detected.

Adduct Formation in the Presence of Alkali Ions:

Enhancing the concentration of alkali ions ($Na^+$, $K^+$, $Rb^+$, $Cs^+$) in either $MoS_2$-suspensions or $MoS_2$-dispersions is performed by addition of respective alkali salt solutions ($Na_2CO_3$, potassium sodium tartrate, $K_2CO_3$, KI, RbI, CsOAc, CsI) to a final alkali salt concentration of each about 20 μg/mL. The hereby formed suspensions or dispersions can be used directly after vortexing to coat a surface suitable for MALDI-MS measurement (commonly on a MALDI-steel-plate) applying the dried-droplet-method (preferably 2×0.7

Figure 16A:
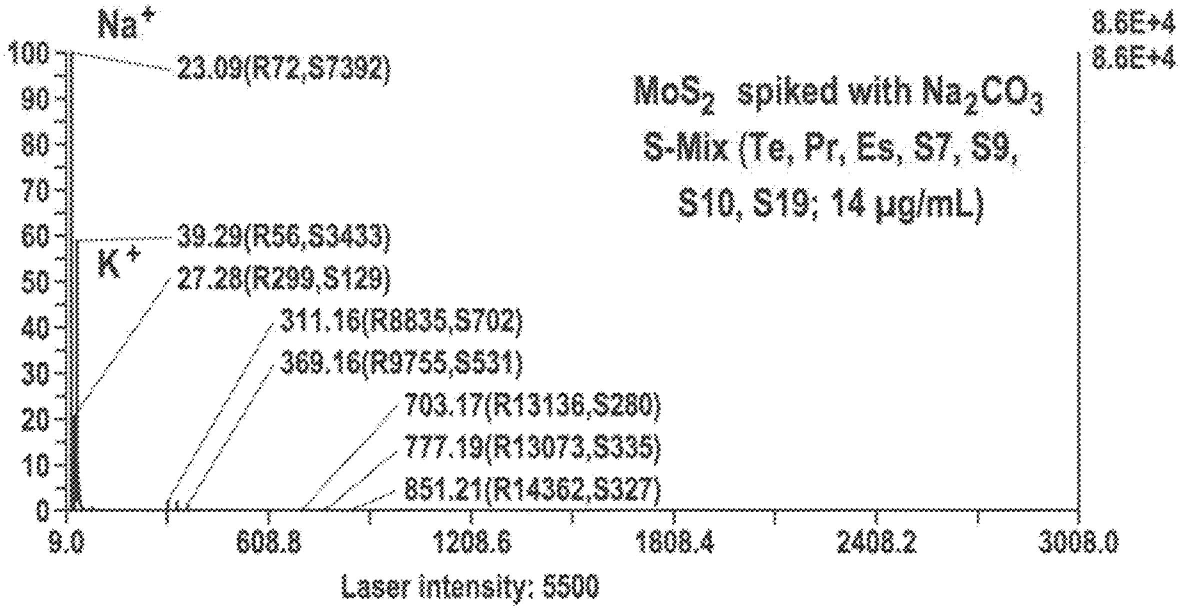
FIG. 16A to FIG. 16D show the MS spectra of a steroid mixture and therapeutically substance mixture in the presence of alkali ions, respectively.
Figure 16B:
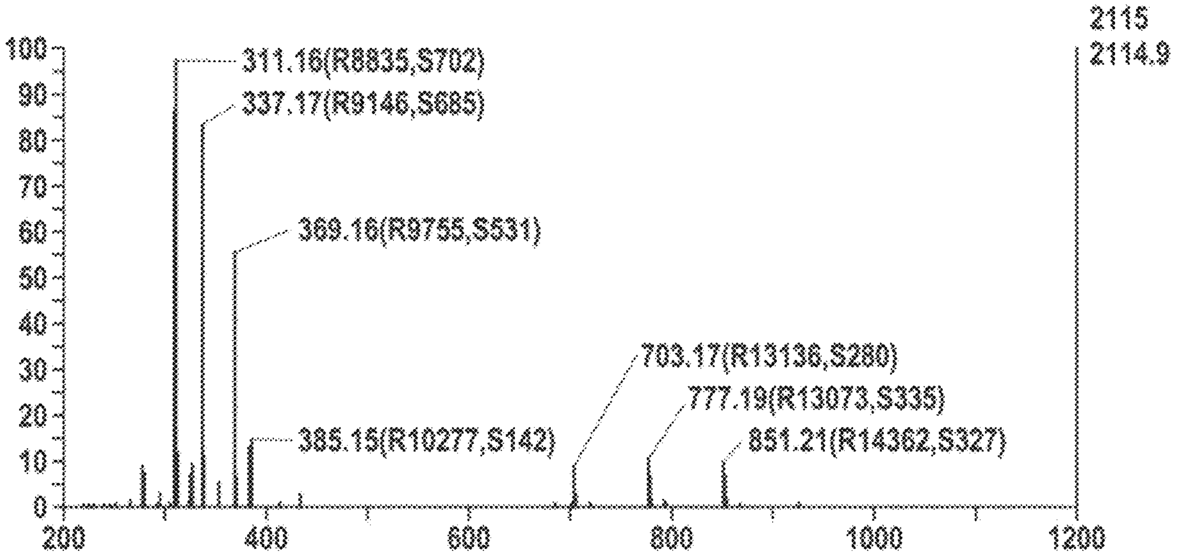

FIG. 16A and FIG. 16B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix and sodium carbonate. FIG. 16B is an enlargement of the MS spectrum of FIG. 16A in the m/z range of 200 to 1200. FIG. 16A and FIG. 16B demonstrate the desorption of the steroid analytes Es, Te, Pr, S7, S9, S10 and S19. The ionization almost exclusively occurred by formation of the corresponding sodium adducts [M+Na]$^+$, with traces of potassium adducts formation [M+K]$^+$. Some background signals, that represent presumably external impurities, can be observed especially in the range of m/z=700-860.

Figure 16C:
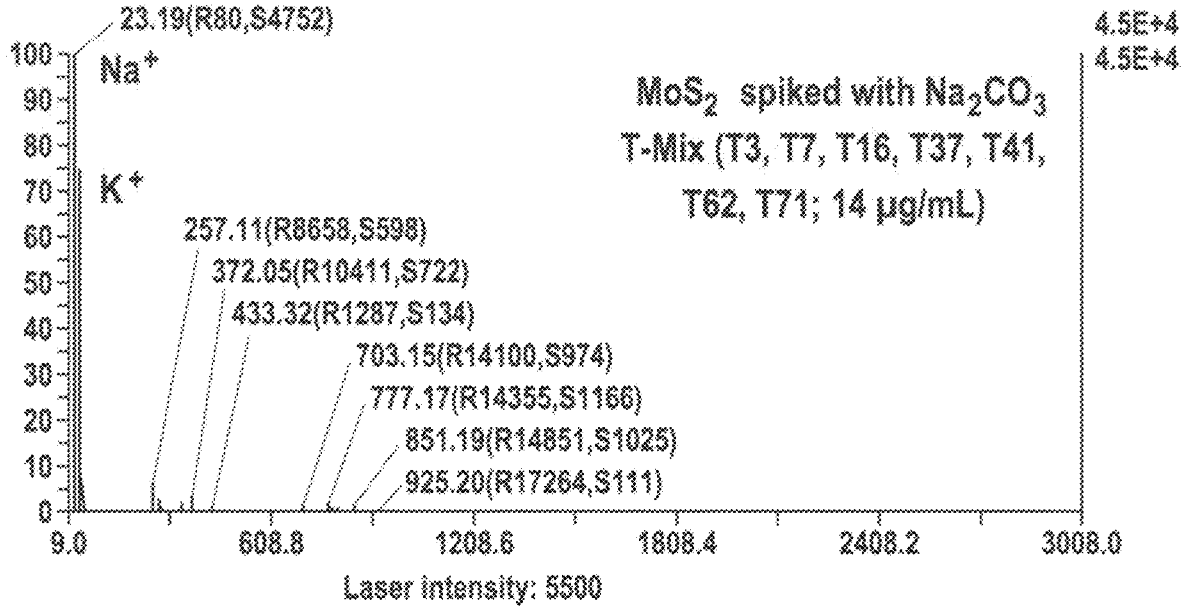
Figure 16D:
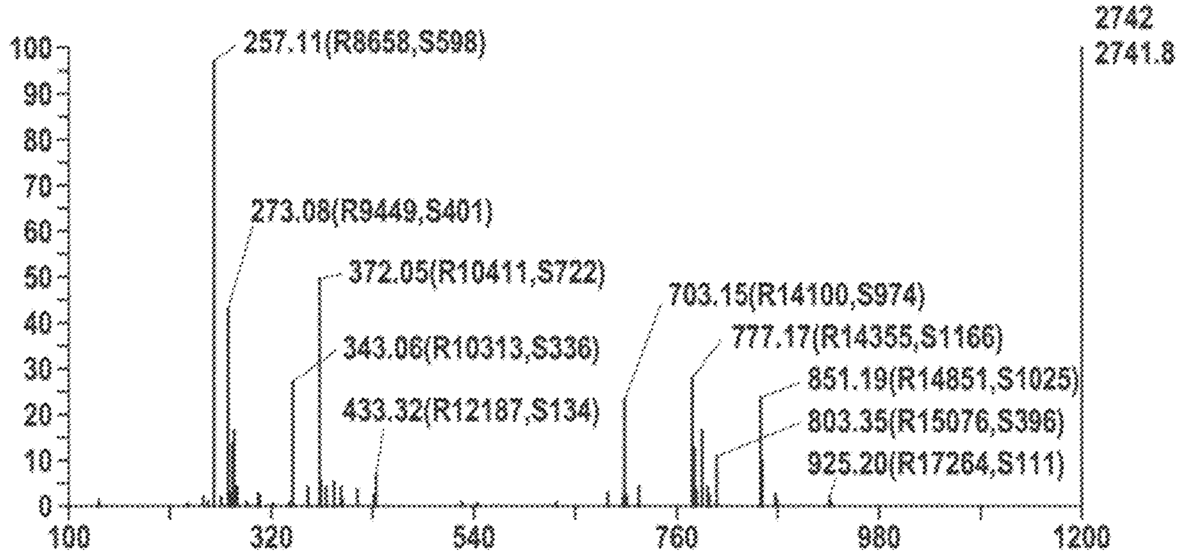

FIG. 16C and FIG. 16D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix and sodium carbonate. FIG. 16D is an enlargement of the MS spectrum of FIG. 16C in the m/z range of 100 to 1200. FIG. 16C and FIG. 16D demonstrate the desorption of the therapeutically substances T7, T16, T37, T41, T62 and T71. The ionization almost exclusively occurred by formation of the corresponding sodium adducts [M+Na]$^+$ with exception of T37 also forming its potassium adduct [M+K]$^+$. Some background signals, that represent presumably external impurities, can be observed especially in the range of m/z=700-930.

Figure 17A:
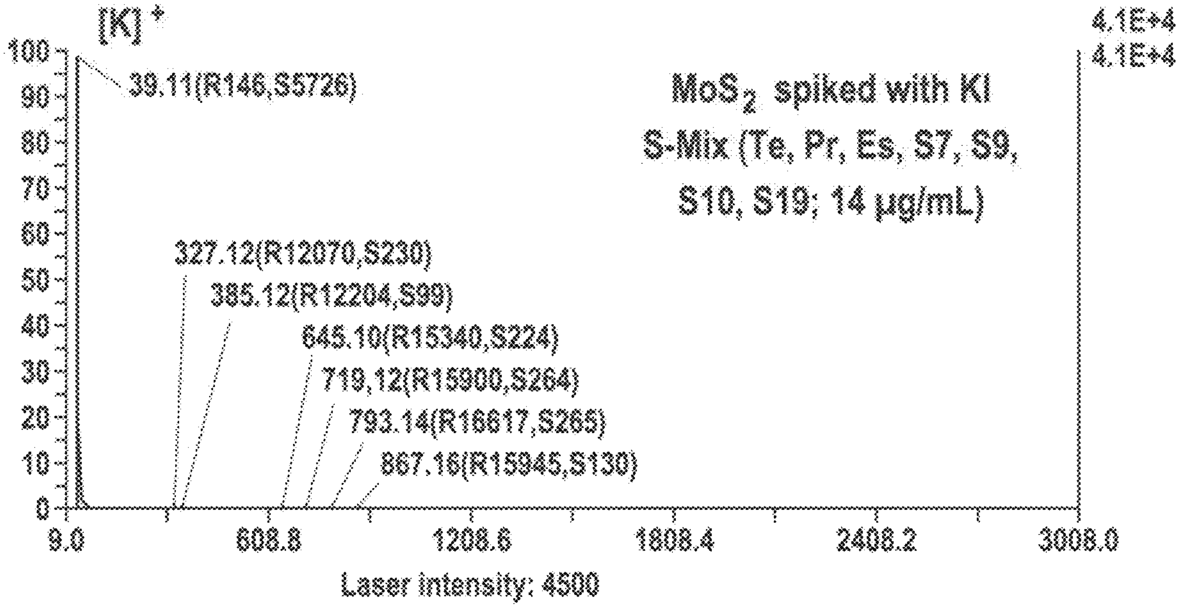
FIG. 17A to FIG. 17D show the MS spectra of a steroid mixture and therapeutically substance mixture in the presence of alkali ions, respectively.
Figure 17B:
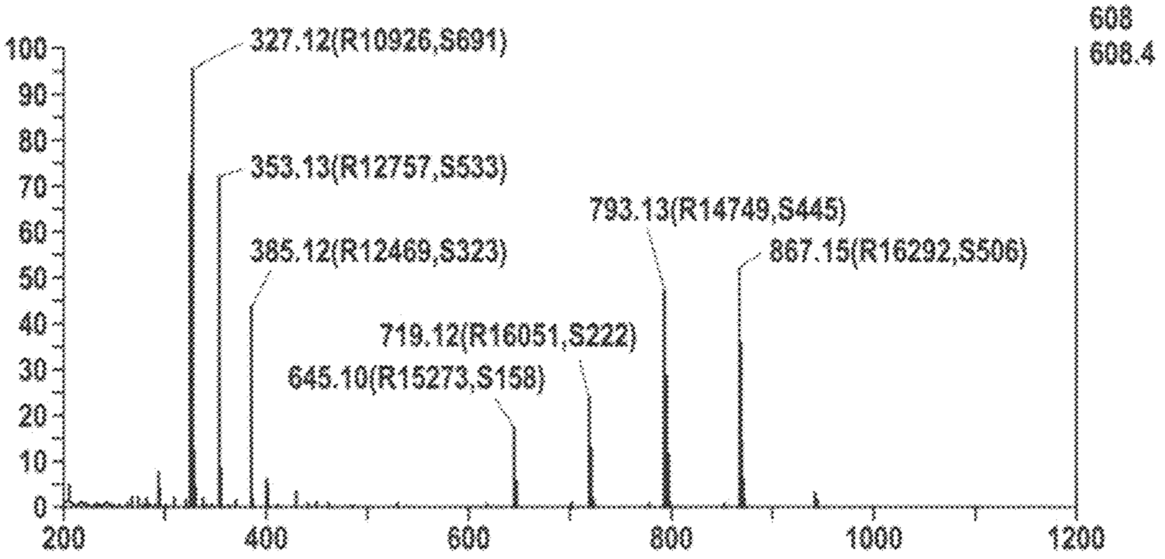

FIG. 17A and FIG. 17B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix and potassium iodide. FIG. 17B is an enlargement of the MS spectrum of FIG. 17A in the m/z range of 200 to 1200. FIG. 17A and FIG. 17B demonstrate the desorption of the steroid analytes Te, Pr, S7 and S9. The ionization almost exclusively occurred by formation of the corresponding potassium adducts $[M+K]^+$, with traces of sodium adducts $[M+Na]^+$.

Some background signals, that represent presumably external impurities, can be observed in the range of m/z=640-950.

Figure 17C:
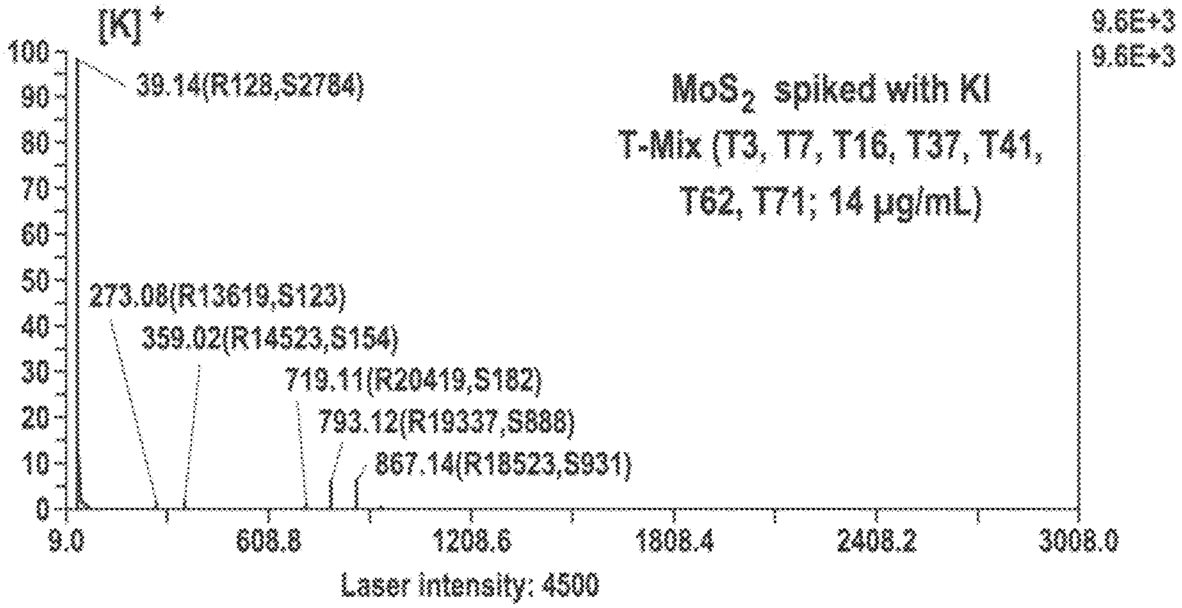
Figure 17D:
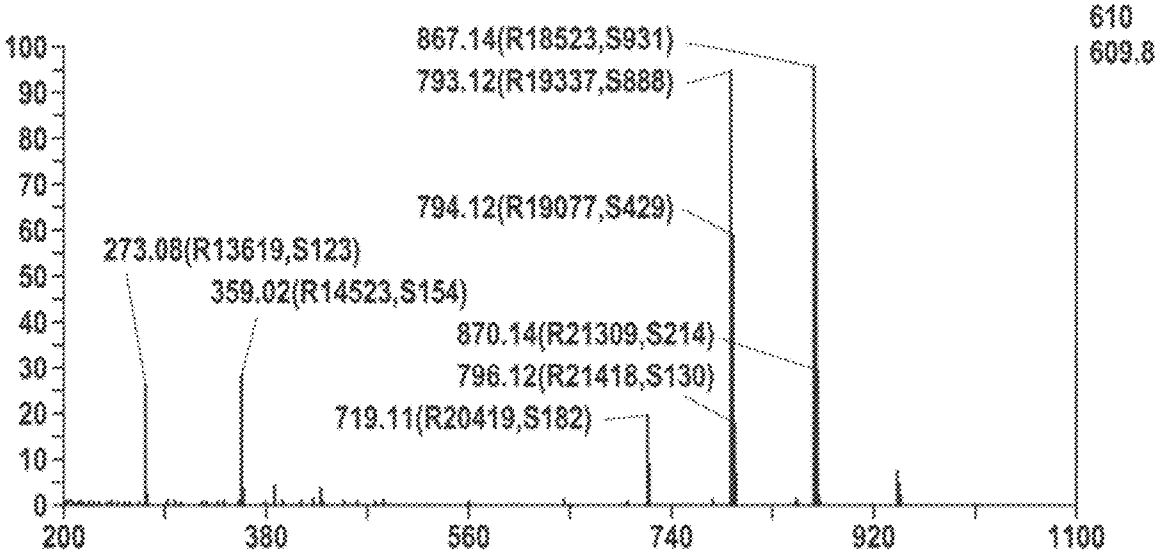

FIG. 17C and FIG. 17D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix and potassium iodide. FIG. 17D is an enlargement of the MS spectrum of FIG. 17C in the m/z range of 200 to 1100. FIGS. 17C and 17D demonstrate the desorption of the therapeutically substances T16 and T37. The ionization exclusively occurred by formation of the corresponding potassium adducts $[M+K]^+$. Some background signals, that represent presumably external impurities, can be observed especially in the range of m/z=700-930.

Figure 18A:
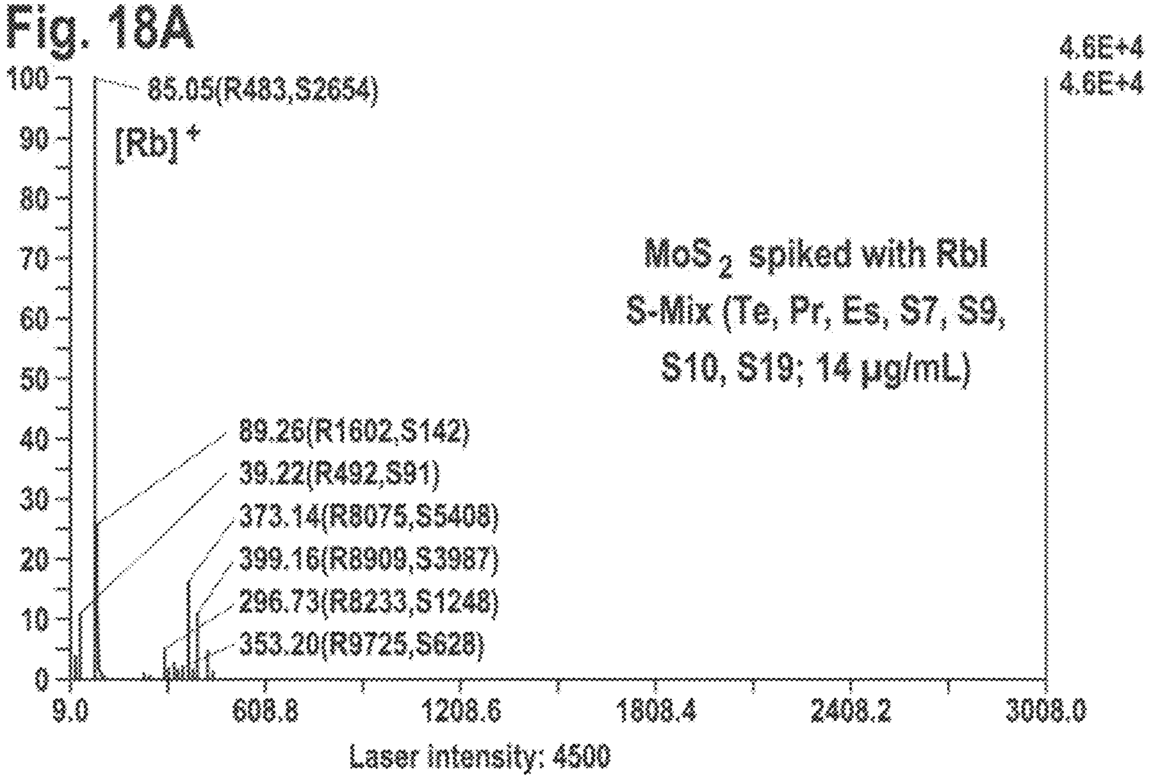
FIG. 18A to FIG. 18D show the MS spectra of a steroid mixture and therapeutically substance mixture in the presence of alkali ions, respectively.
Figure 18B:
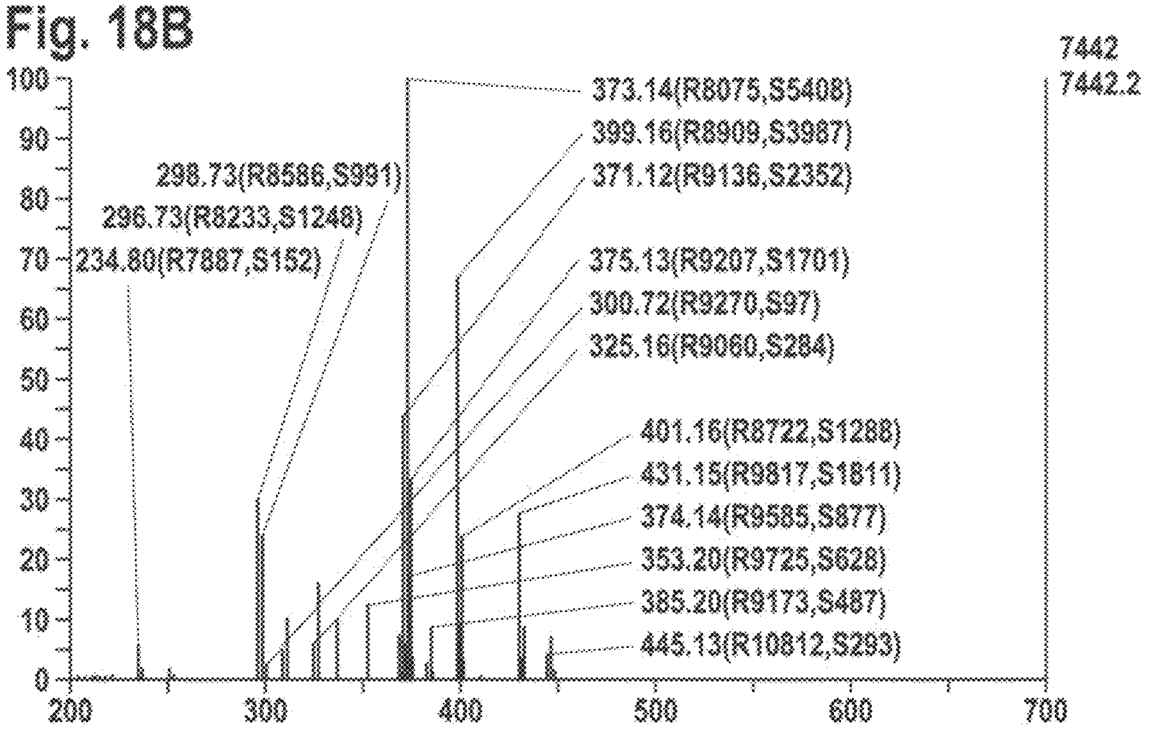

FIG. 18A and FIG. 18B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix premixed with RbI. FIG. 18B is an enlargement of the MS spectrum of FIG. 18A in the m/z range of 200 to 700. FIG. 18A and FIG. 18B demonstrate the desorption of the steroid analytes Te, Pr, S7, S9, S10 and S19. The ionization mainly occurred by formation of the corresponding rubidium adducts $[M+Rb]^+$, with minor residuals of sodium and potassium adducts $[M+Na/K]^+$. Furthermore, no significant background can be observed.

Figure 18C:
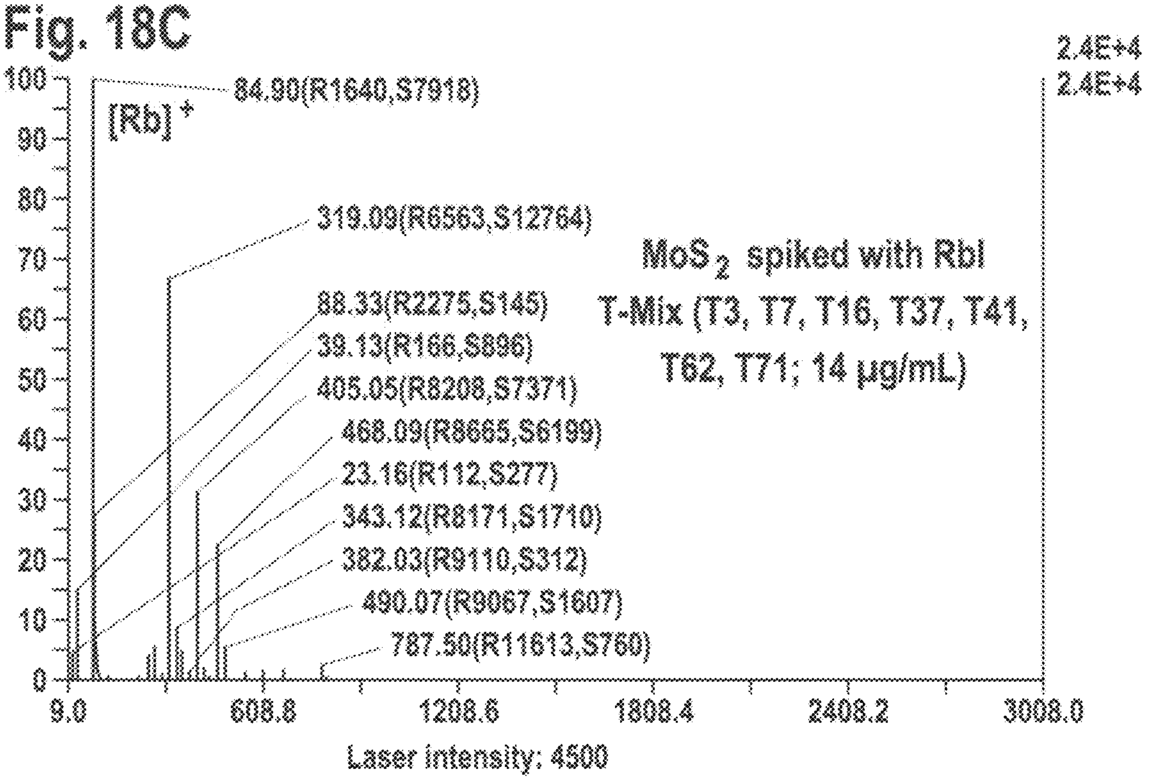
Figure 18D:
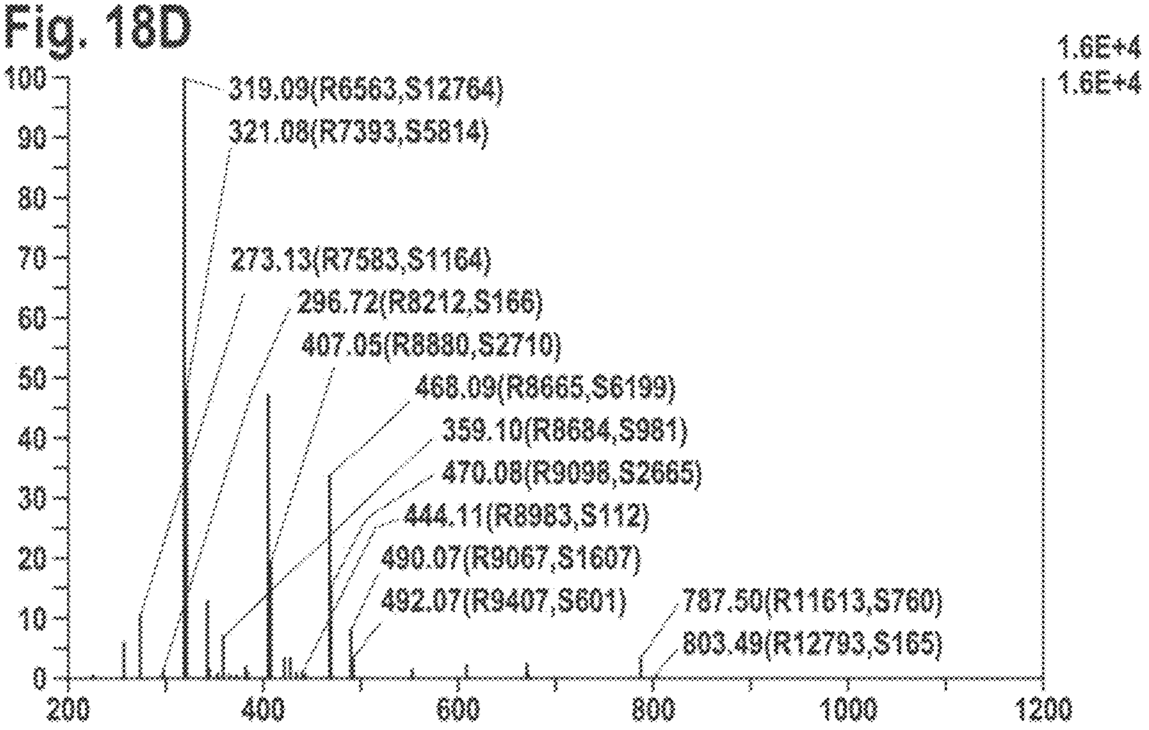

FIG. 18C and FIG. 18D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix premixed with RbI. FIG. 18D is an enlargement of the MS spectrum of FIG. 18C in the m/z range of 200 to 1200. FIG. 18C and FIG. 18D demonstrate the desorption of the therapeutically substances T3, T16, T37 and T71. The ionization mainly occurred by formation of the corresponding rubidium adducts $[M+Rb]^+$, with minor residuals of sodium and potassium adducts $[M+Na/K]^+$. Furthermore, no significant background can be observed.

Figure 19A:
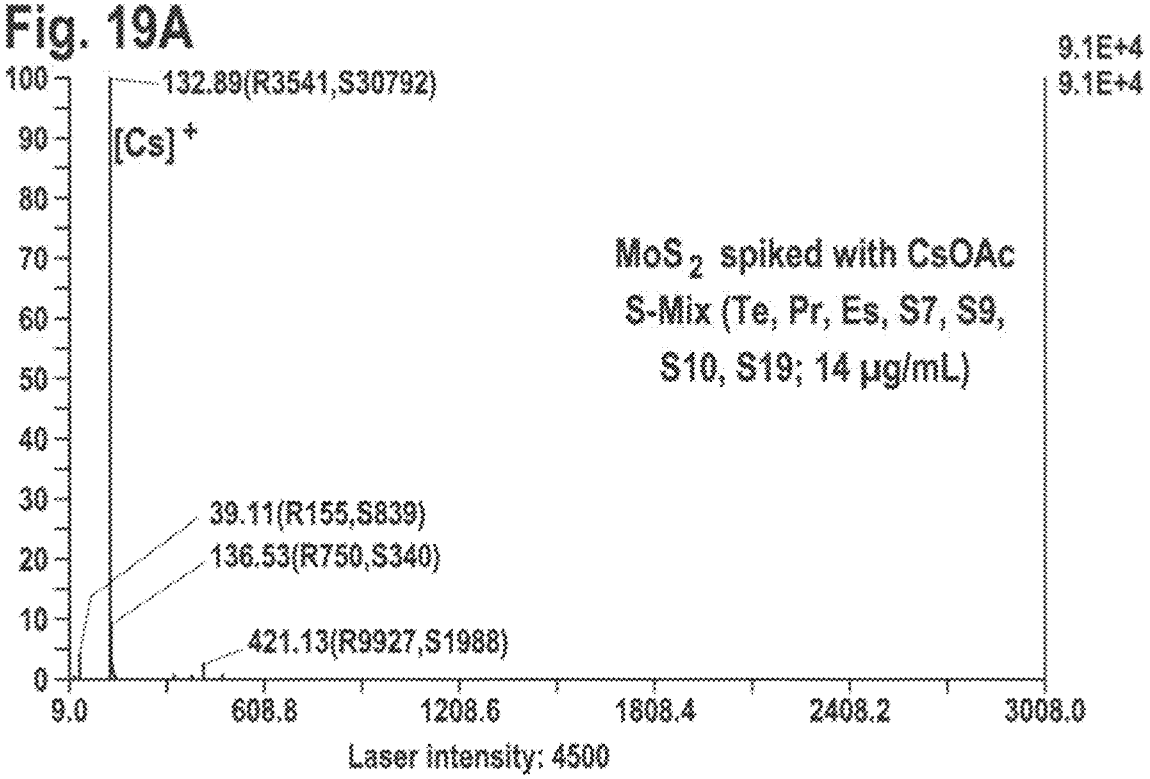
FIG. 19A to FIG. 19D show the MS spectra of a steroid mixture and therapeutically substance mixture in the presence of alkali ions, respectively.
Figure 19B:
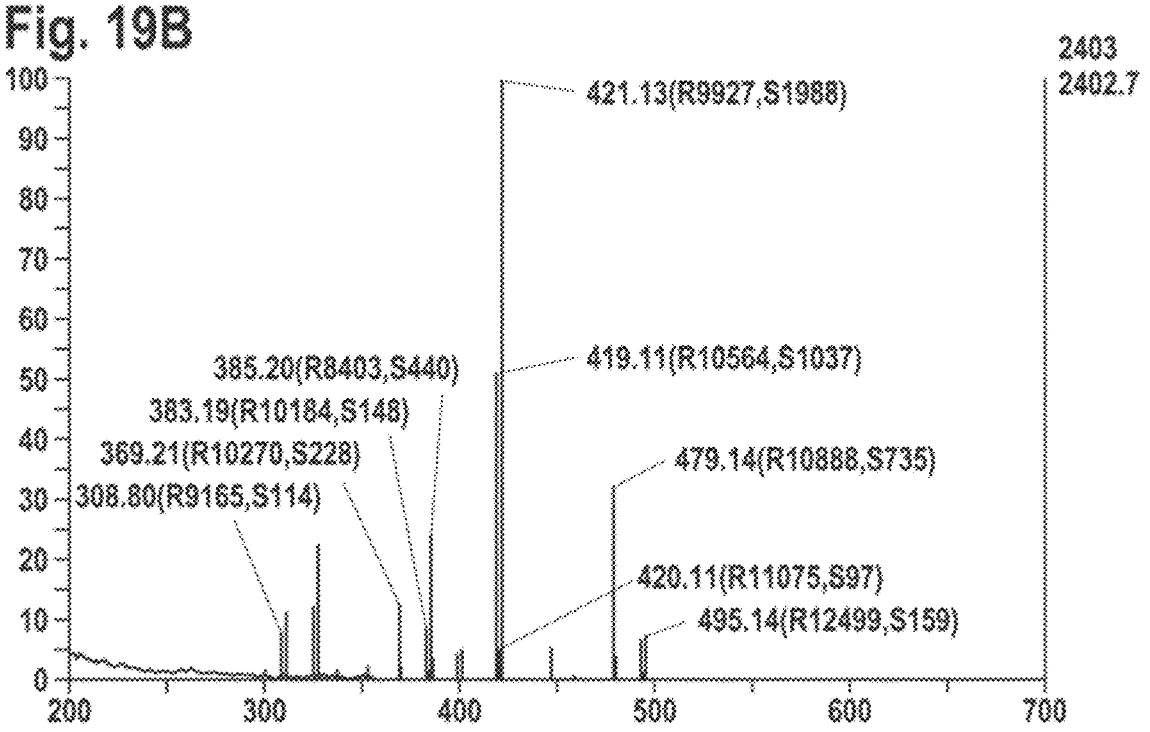

FIG. 19A and FIG. 19B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix premixed with CsOAc. FIG. 19B is an enlargement of the MS spectrum of FIG. 19A in the m/z range of 200 to 700. FIG. 19A and FIG. 19B demonstrate the desorption of the steroid analytes Te, Pr, S7, S9, S10 and S19. The ionization mainly occurred by formation of the corresponding cesium adducts $[M+Cs]^+$, with minor residuals of sodium and potassium adducts $[M+Na/K]^+$. Furthermore, no significant background can be observed.

Figure 19C:
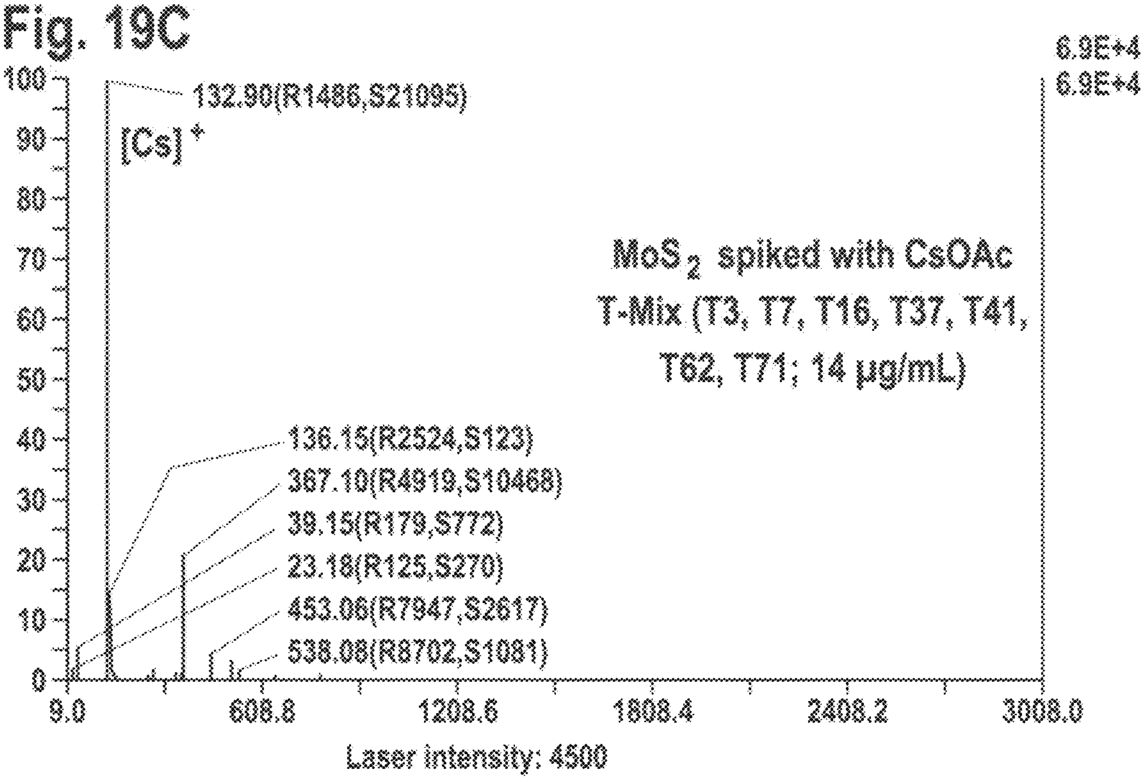
Figure 19D:
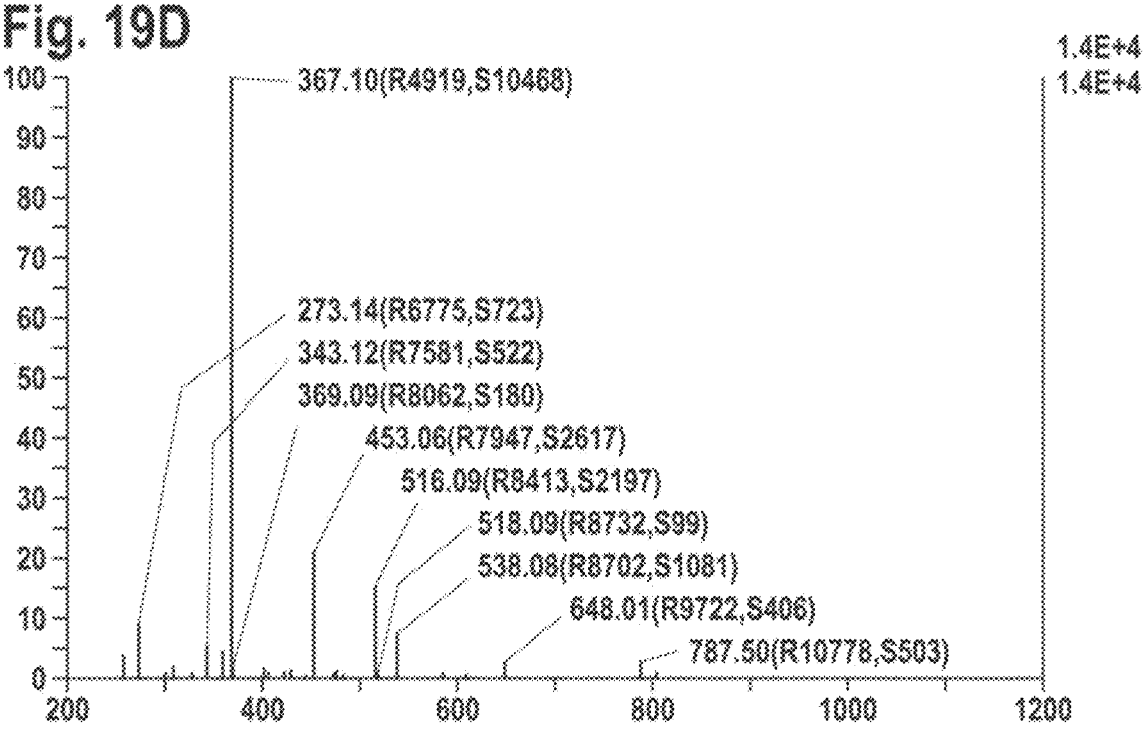

FIG. 19C and FIG. 19D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix premixed with CsOAc. FIG. 19D is an enlargement of the MS spectrum of FIG. 19C in the m/z range of 200 to 1200. FIG. 19C and FIG. 19D demonstrate the desorption of the therapeutically substances T16, T37 and T71. The ionization mainly occurred by formation of the corresponding cesium adducts $[M+Cs]^+$, with minor residuals of sodium and potassium adducts $[M+Na/K]^+$. Furthermore, no significant background can be observed.

Experiments to Enhance K-Pseudomolecular Ion Species:

An additional method to enhance the presence of the potassium-adduct species is shown in the presence of a crown ether (18-crown-6). Therefore, a bulk $MoS_2$-suspension ($MeCN/H_2O$=50/50) gets spiked with a solution of 18-crown-6 ($MeCN/H_2O$=50/50), to a final concentration of 20 μg/mL of the latter one. After vigorously vortexing, a sample is taken, that gets additionally spiked with a solution of $K_2CO_3$ ($MeCN/H_2O$=50/50), to a final concentration of 20 μg/mL of the latter one. Both obtained suspensions can be used directly to coat a surface suitable for MALDI-MS measurement (commonly on a MALDI-steel-plate, ITO-glass slide, or similar) applying the dried-droplet method (preferably 2×0.7 μL). Subsequently after analyte deposition and air-drying, MALDI-TOF measurements are performed in positive mode adjusting the laser intensity to an optimal value of about 4500 units with a total of 2000 laser shots per spot. Analyte signals occurred with bulk-$MoS_2$+18-crown-6 as alkali adducts ($[M+Na]^+$ and $[M+K]^+$, whereas samples on bulk-$MoS_2$+18-crown-6 spiked with $K_2CO_3$ resulted almost completely in pure $[M+K]^+$-adduct species.

Figure 20A:
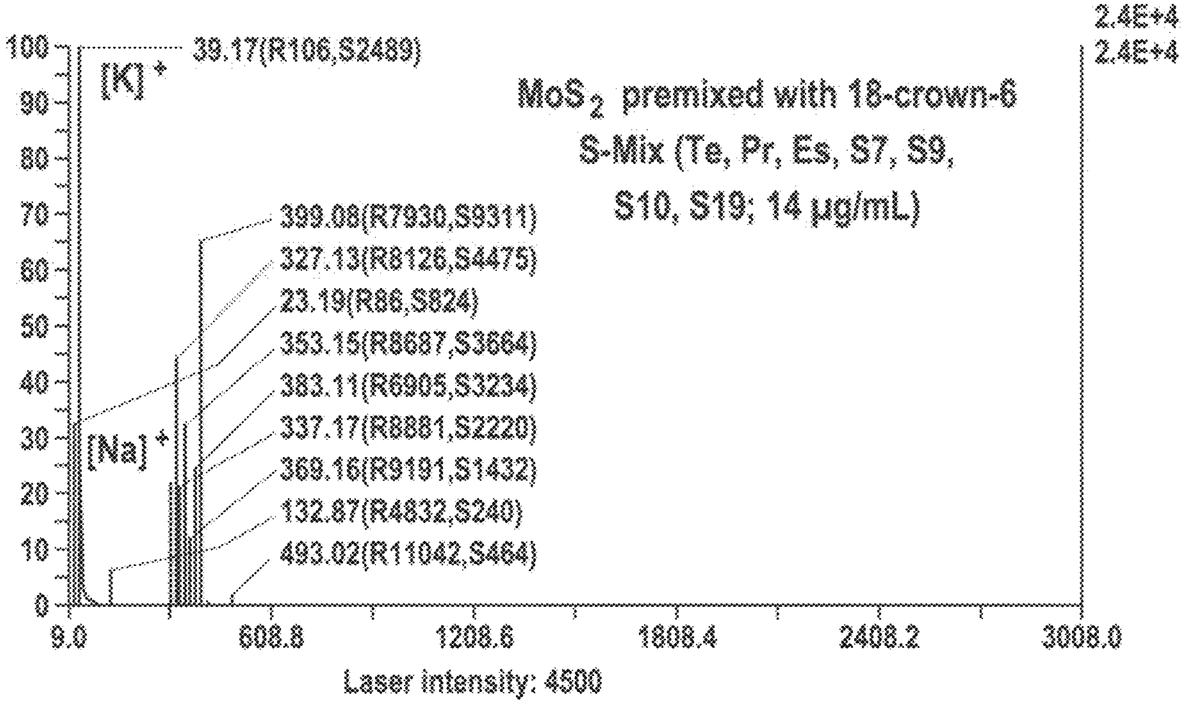
FIG. 20A to FIG. 20D show the MS spectra of a steroid mixture and therapeutically substance mixture premixed with 18-crown 6 ether, respectively.
Figure 20B:
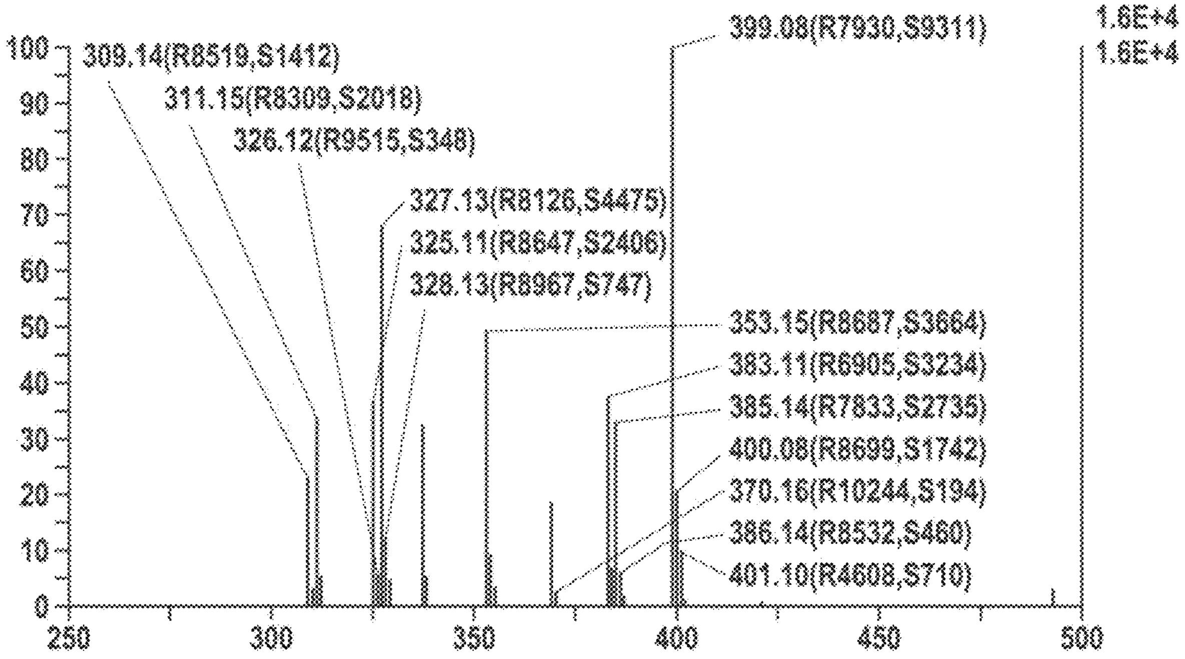

FIG. 20A and FIG. 20B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix premixed with 18-crown-6 ether. FIG. 20B is an enlargement of the MS spectrum of FIG. 20A in the m/z range of 250 to 500. FIG. 20A and FIG. 20B demonstrate the desorption of the steroid analytes Te, Pr, S7, S9, S10 and S19. The ionization occurred by formation of the corresponding sodium or potassium adducts $[M+Na/K]^+$. Besides an additional signal at m/z=399, no significant background can be observed.

Figure 20C:
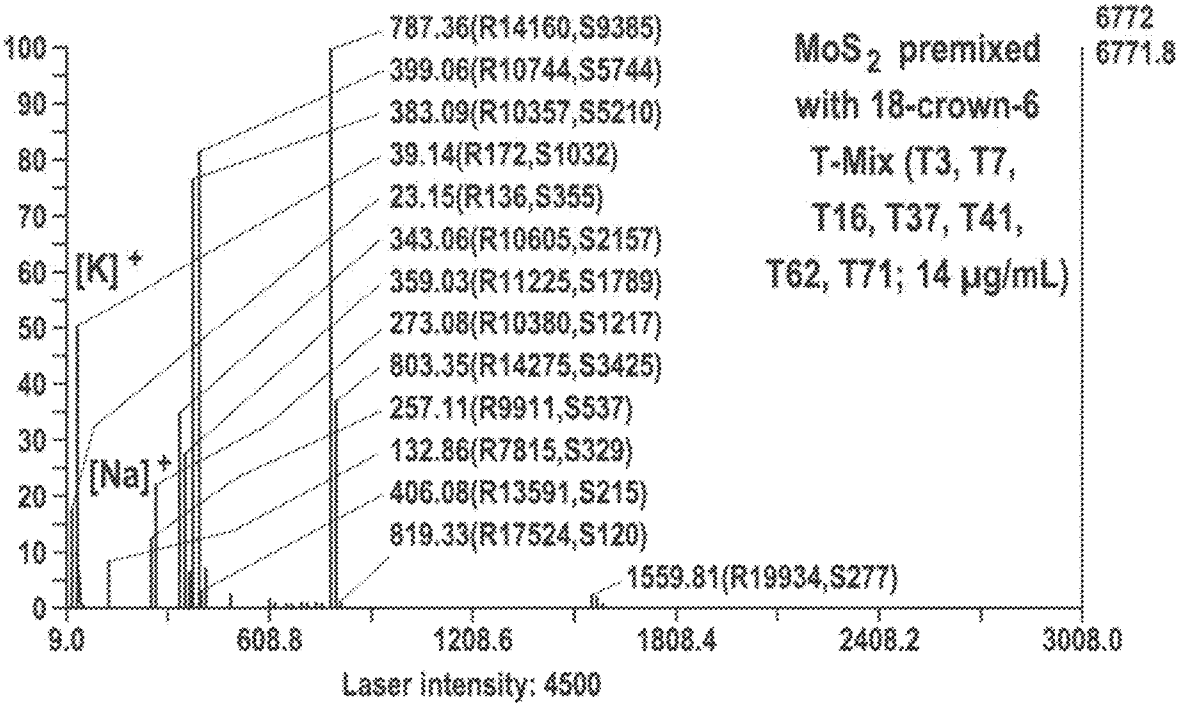
Figure 20D:
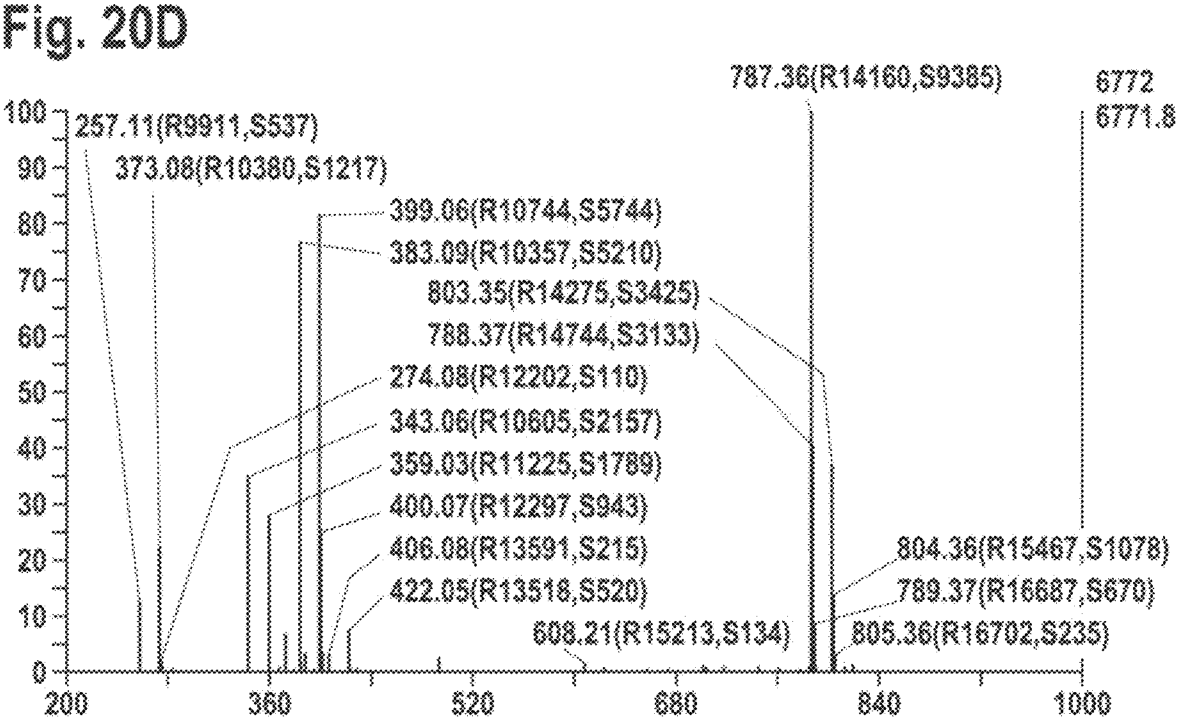

FIG. 20C and FIG. 20D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix premixed with 18-crown-6 ether. FIG. 20D is an enlargement of the MS spectrum of FIG. 20C in the m/z range of 200 to 1000. FIG. 20C and FIG. 20D demonstrate the desorption of the therapeutically substances T3, T16, T37 and T71. The ionization occurred by formation of the corresponding sodium or potassium adducts $[M+Na/K]^+$. Besides an additional signal at m/z=383 and m/z=399, no significant background can be observed.

Figure 21A:
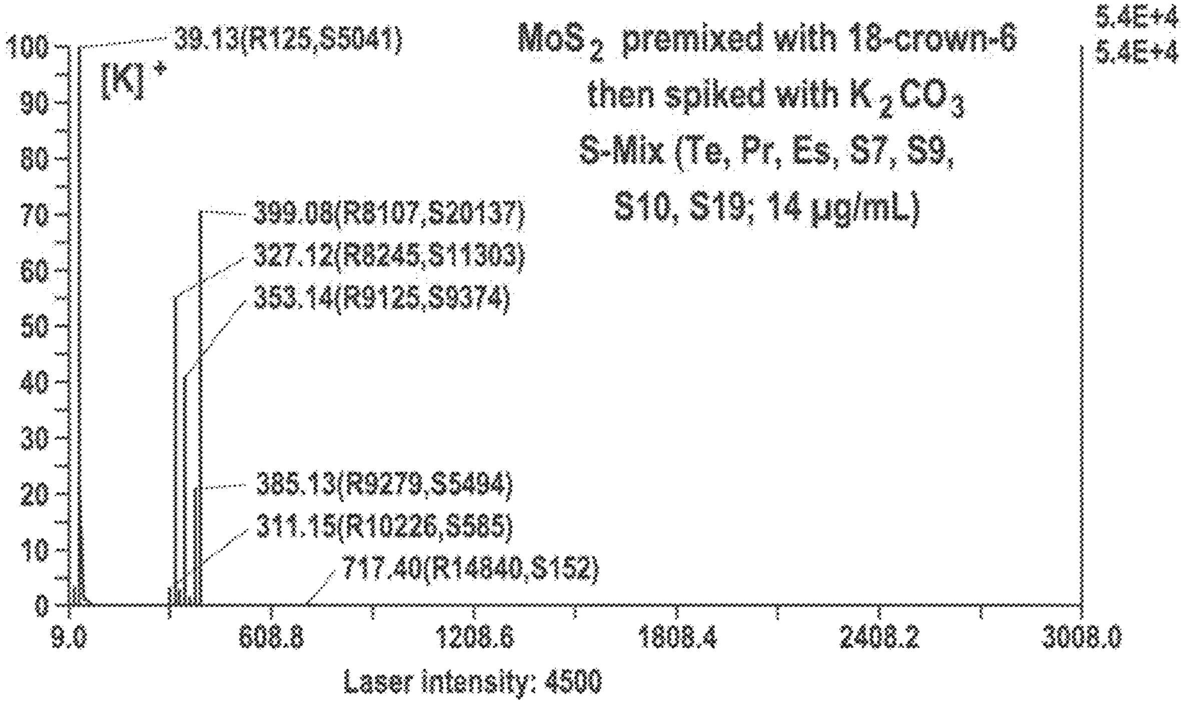
FIG. 21A to FIG. 21D show the MS spectra of a steroid mixture and therapeutically substance mixture premixed with 18-crown 6 ether, respectively.
Figure 21B:
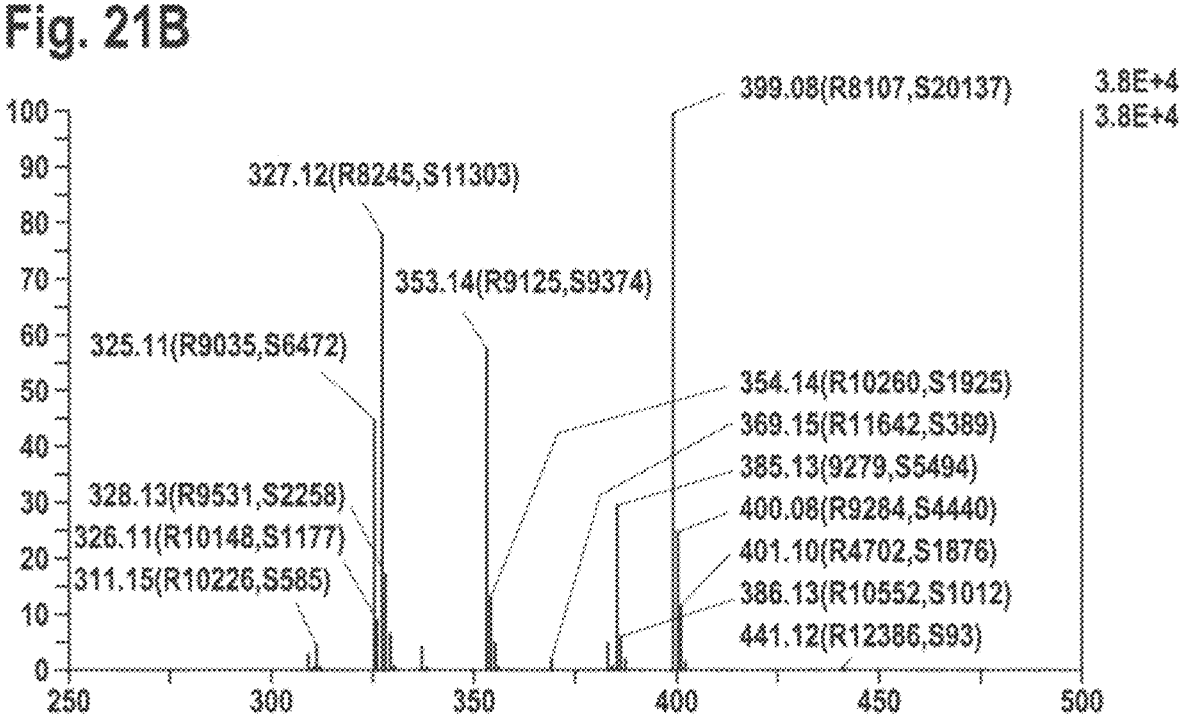

FIG. 21A and FIG. 21B show the relative intensity or absolute intensity as a function of the m/z of a steroid mixture comprising seven steroids: Te, Pr, Es, S7, S9, S10 and S19, each 14 μg/ml. The mixture of analytes is prepared on a bulk $MoS_2$ matrix premixed with 18-crown-6 ether, then $K_2CO_3$. FIG. 21B is an enlargement of the MS spectrum of FIG. 21A in the m/z range of 250 to 500. FIG. 21A and FIG. 21B demonstrate the desorption of the steroid analytes Es, Te, Pr, S7, S9, S10 and S19. The ionization almost exclusively occurred by formation of the corresponding potassium adducts $[M+K]^+$, with traces of sodium adducts $[M+Na]^+$. Besides an additional signal at m/z=399, no significant background can be observed.

Figure 21C:
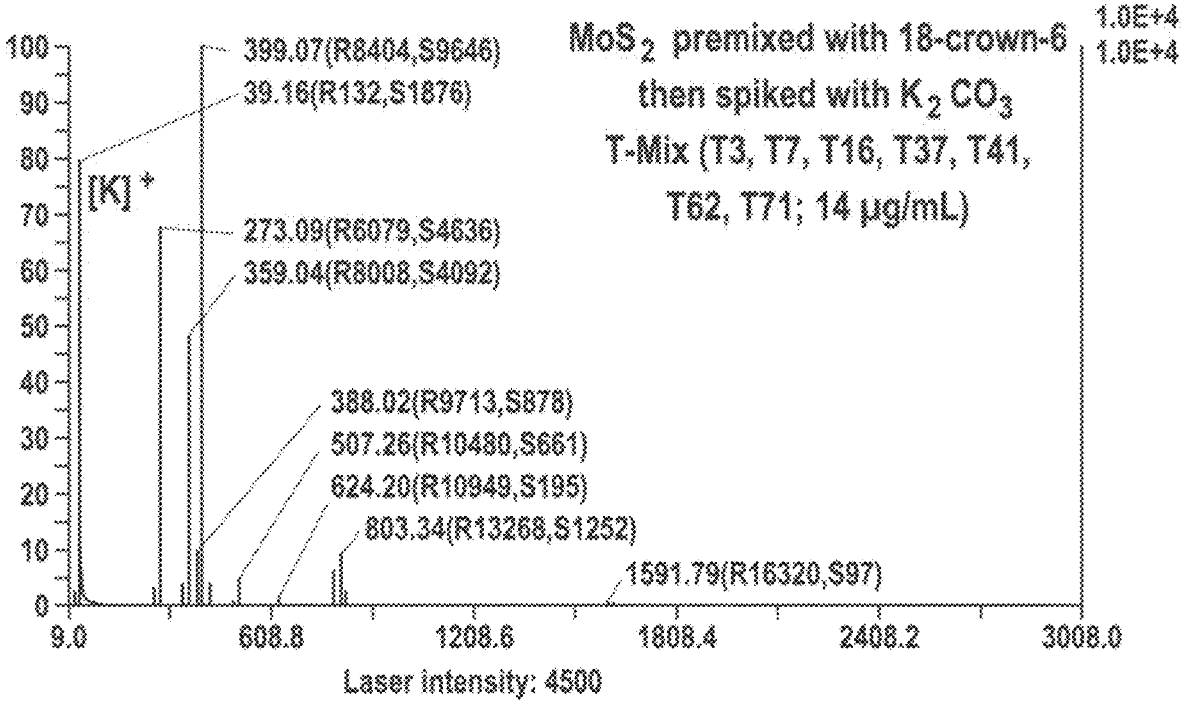
Figure 21D:
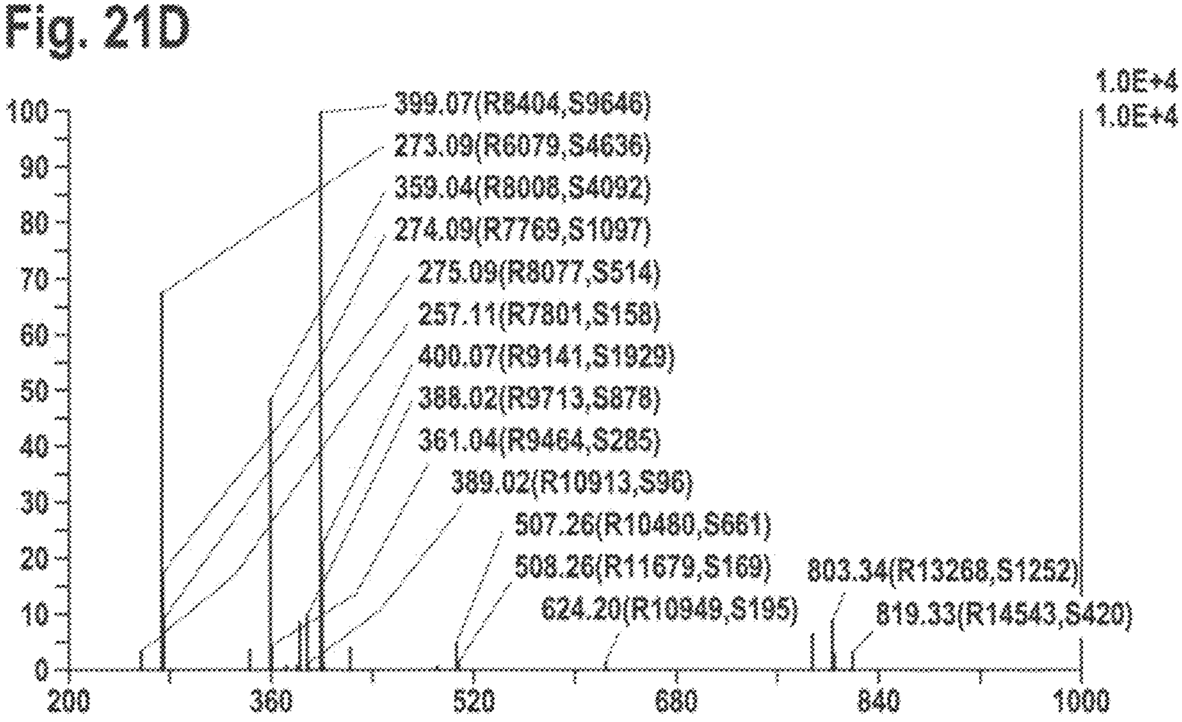

FIG. 21C and FIG. 21D show the relative intensity or absolute intensity as a function of the m/z of a mixture of seven therapeutically substances: T3, T7, T16, T37, T41, T62 and T71, each 14 μg/ml. The mixture of analytes is prepared on a bulk $MoS_2$ matrix premixed with 18-crown-6 ether, then $K_2CO_3$. FIG. 21D is an enlargement of the MS spectrum of FIG. 21C in the m/z range of 200 to 1000. FIG. 20C and FIG. 20D demonstrate a desorption of the therapeutically substances T3, T7, T16, T37, T41 and T71. The ionization almost exclusively occurred by formation of the corresponding potassium adducts $[M+K]^+$, with traces of sodium adducts $[M+Na]^+$. Besides an additional signal at m/z=399, no significant background can be observed.

Li-Intercalated $MoS_2$/$WS_2$ (State of the Art):

To compare the herein described method with the more effortful literature known lithium-exfolation process (Xu et al., ACS Sens. 2018, 3, 806-814), commercially available Li-intercalated $MoS_2$ and $WS_2$ material is applied on a comparable way. This is performed sonicating the $MoS_2$/$WS_2$ Li-intercalated suspension (MeCN/$H_2O$=50/50, 10 mg/mL) for 4 h in an ultrasonic bath followed by centrifugation (3000 rpm) to remove unexfoliated $MoS_2$/$WS_2$-material and an additional washing step to obtain $MoS_2$/$WS_2$-monolayer solutions. With a subsequent SALDI-measurement, only sonicated $MoS_2$-monolayer solution was able to desorbtion/ionization the tested steroid molecules and also some of the therapeutic molecules (resulting in alkali adducts $[M+Li]^+$, $[M+Na]^+$ and $[M+K]^+$), while sonicated $WS_2$-material—prepared by the Li-intercalation method—was not compatible to LDI of analytes.

Figure 22A:
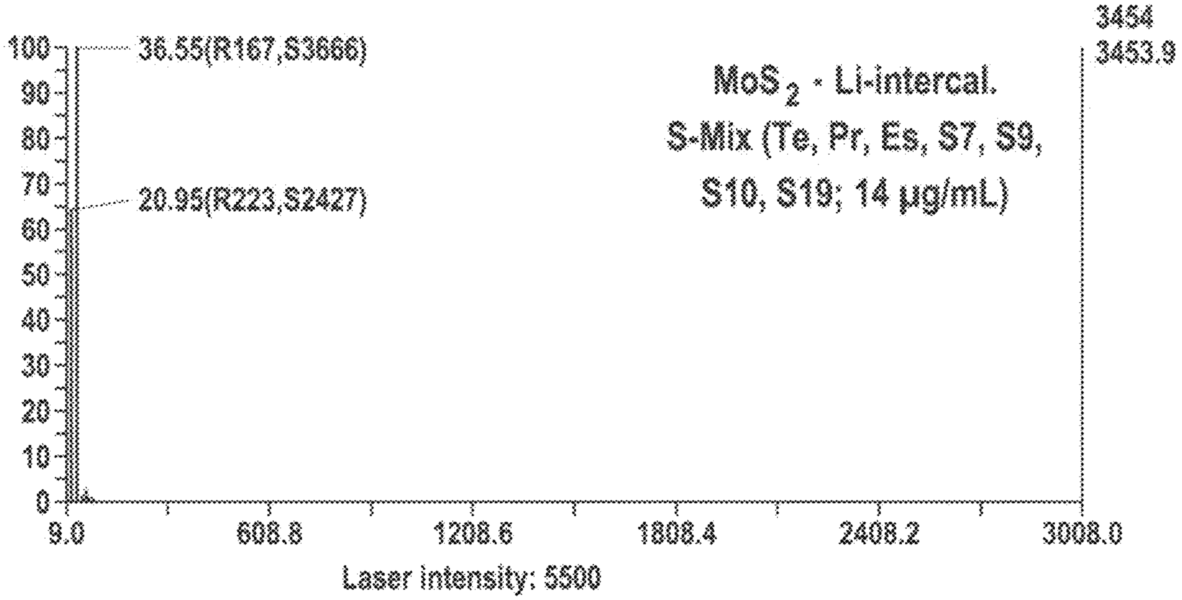
FIG. 22A to FIG. 22D show the MS spectra of a steroid mixture and therapeutically substance mixture premixed prepared on a Li-intercalated $MoS_2/WS_2$ matrix, respectively.
Figure 22B:
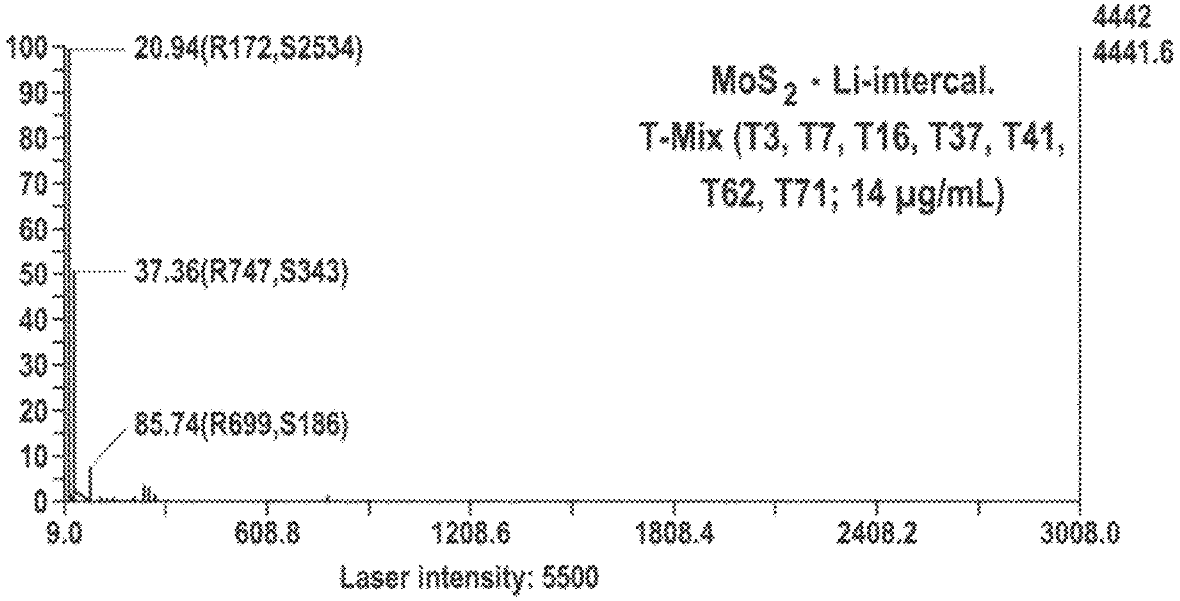

FIG. 22A and FIG. 22B show the relative intensity or absolute intensity as a function of the m/z of a steroid mixture comprising seven steroids: Te, Pr, Es, S7, S9, S10 and S19, each 14 μg/ml, and a mixture of seven therapeutically substances: T3, T7, T16, T37, T41, T62 and T71, each 14 μg/ml, respectively. The mixture of analytes is prepared on a $MoS_2$ Li intercalated matrix. There can no analyte signal be detected.

Figure 22C:
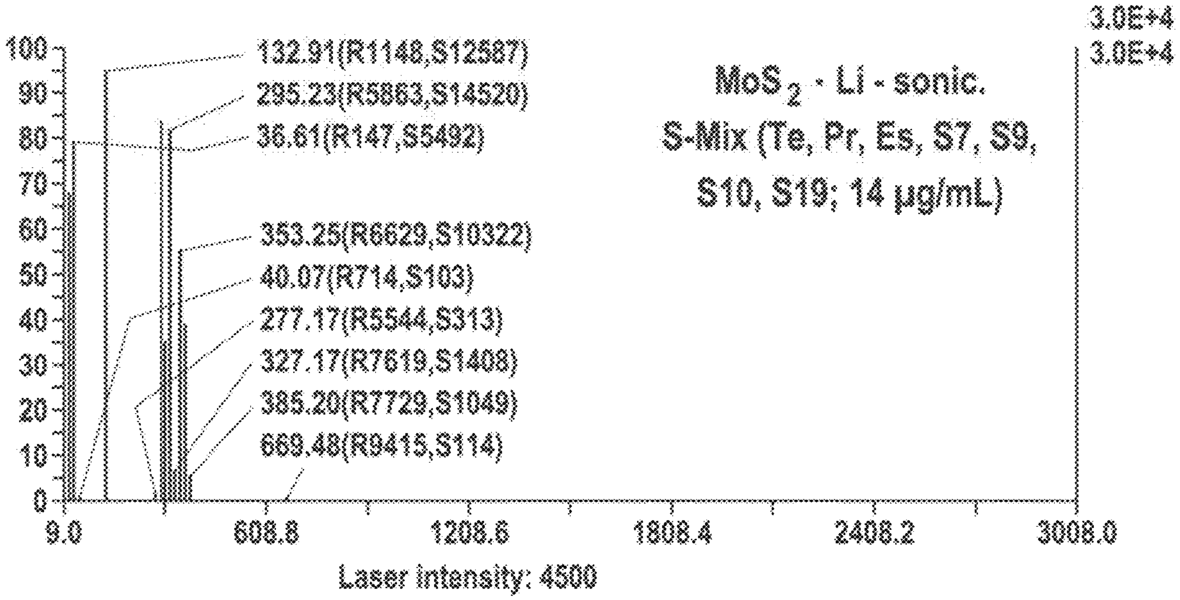
Figure 22D:
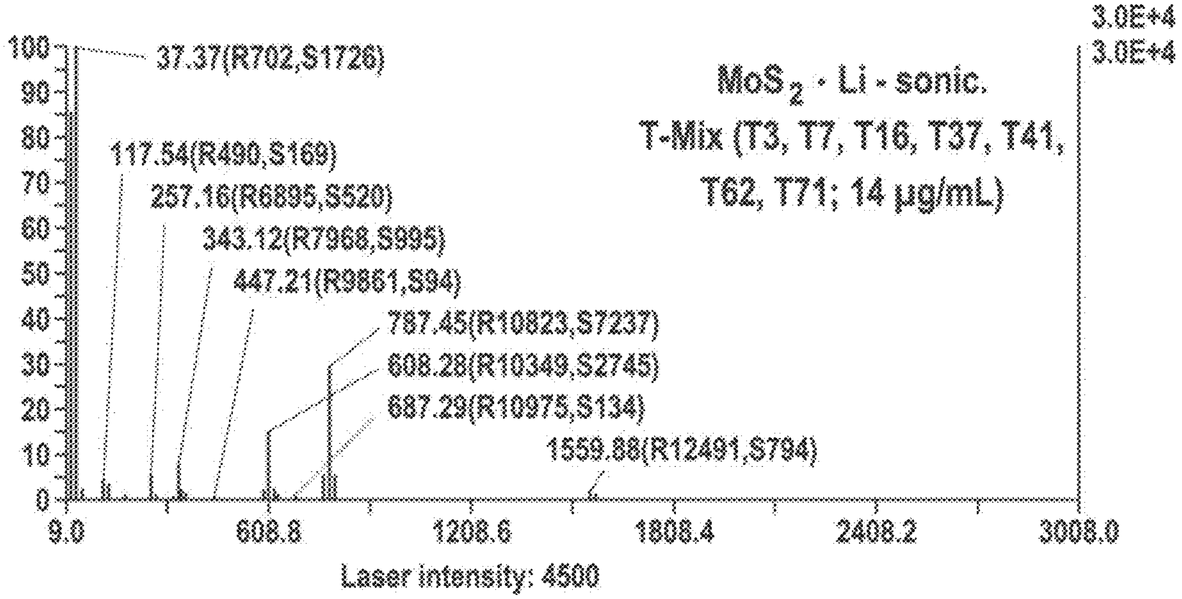

FIG. 22C and FIG. 22D show the relative intensity or absolute intensity as a function of the m/z of a steroid mixture comprising seven steroids: Te, Pr, Es, S7, S9, S10 and S19, each 14 μg/ml, and a mixture of seven therapeutically substances: T3, T7, T16, T37, T41, T62 and T71, each 14 μg/ml, respectively. The mixture of analytes is prepared on a $MoS_2$ Li intercalated matrix (sonicated and centrifuged). In comparison to the herein described $MoS_2$-matrix, the as prepared and sonicated Li intercalated $MoS_2$ matrix showed a more complex outcome resulting in lithium, sodium and potassium adducts formation of the tested steroids $[M+Li/Na/K]^+$. Due to the splittion of molecular peak intensity onto three independent ion species (Na+, K+, Li+) the quantification limit capability of the method is only ⅓ of the capability if only one ion species (e.g. $Na^+$ or $K^+$) is observed. Therefore as low as possible different ion adduct species are preferred.

Figure 23A:
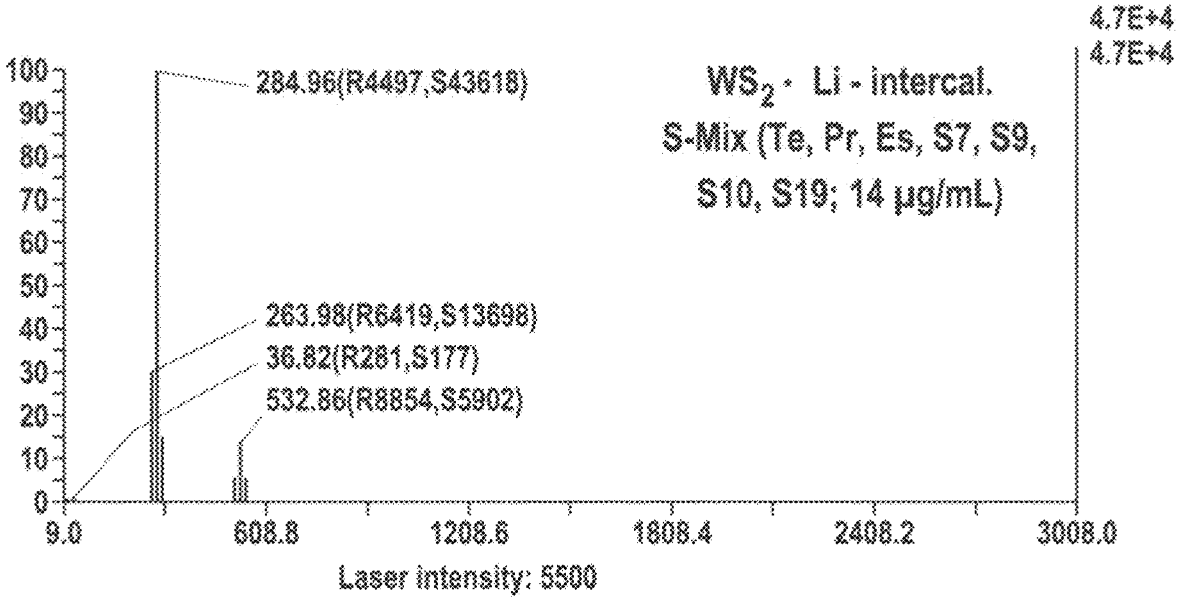
FIG. 23A to FIG. 23D show the MS spectra of a steroid mixture and therapeutically substance mixture premixed prepared on a Li-intercalated $MoS_2/WS_2$ matrix, respectively.
Figure 23B:
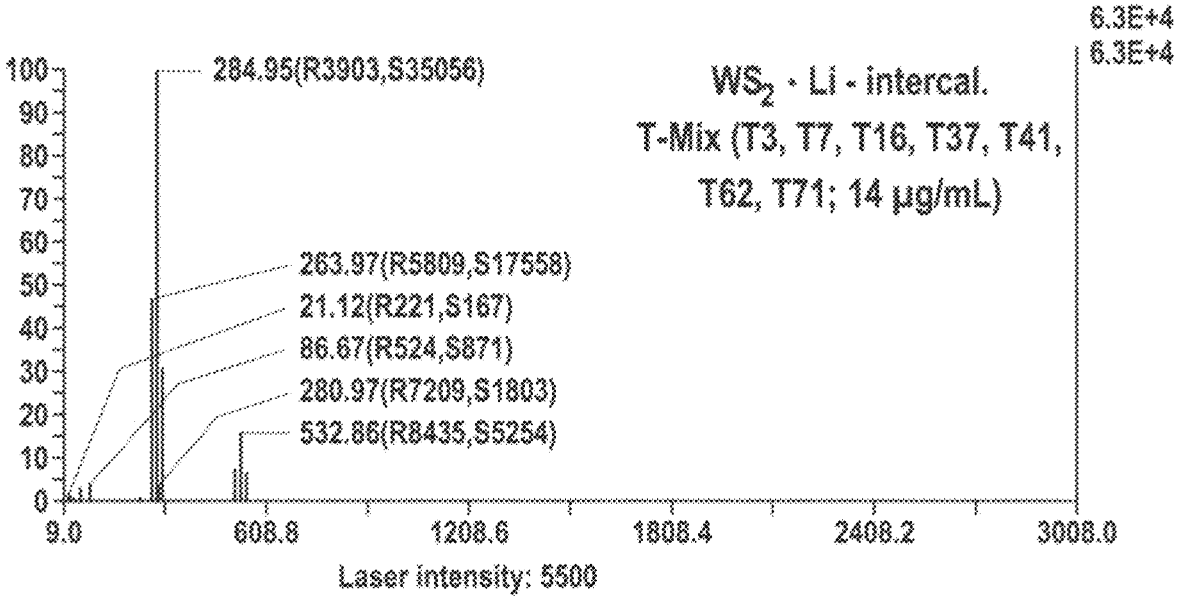

FIG. 23A and FIG. 23B show the relative intensity or absolute intensity as a function of the m/z of a steroid mixture comprising seven steroids: Te, Pr, Es, S7, S9, S10 and S19, each 14 μg/ml, and a mixture of seven therapeutically substances: T3, T7, T16, T37, T41, T62 and T71, each 14 μg/ml, respectively. The mixture of analytes is prepared on a $WS_2$ Li intercalated matrix. There can just background signal be detected.

Figure 23C:
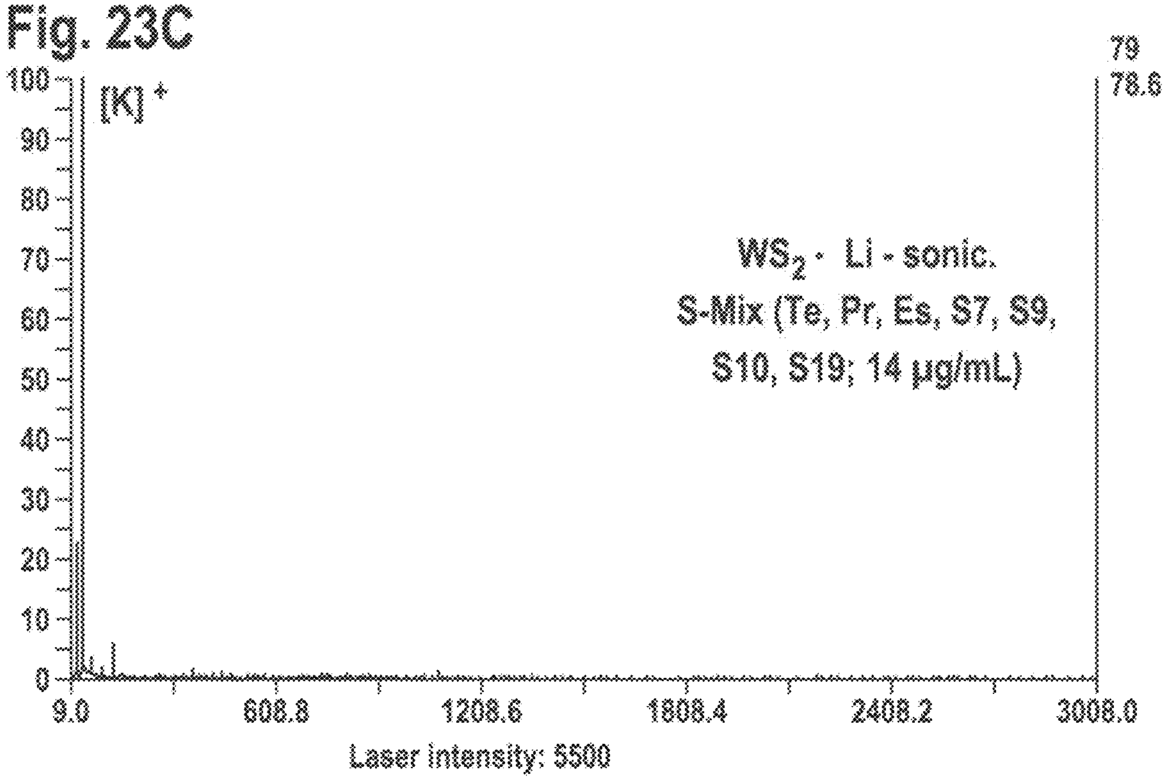
Figure 23D:
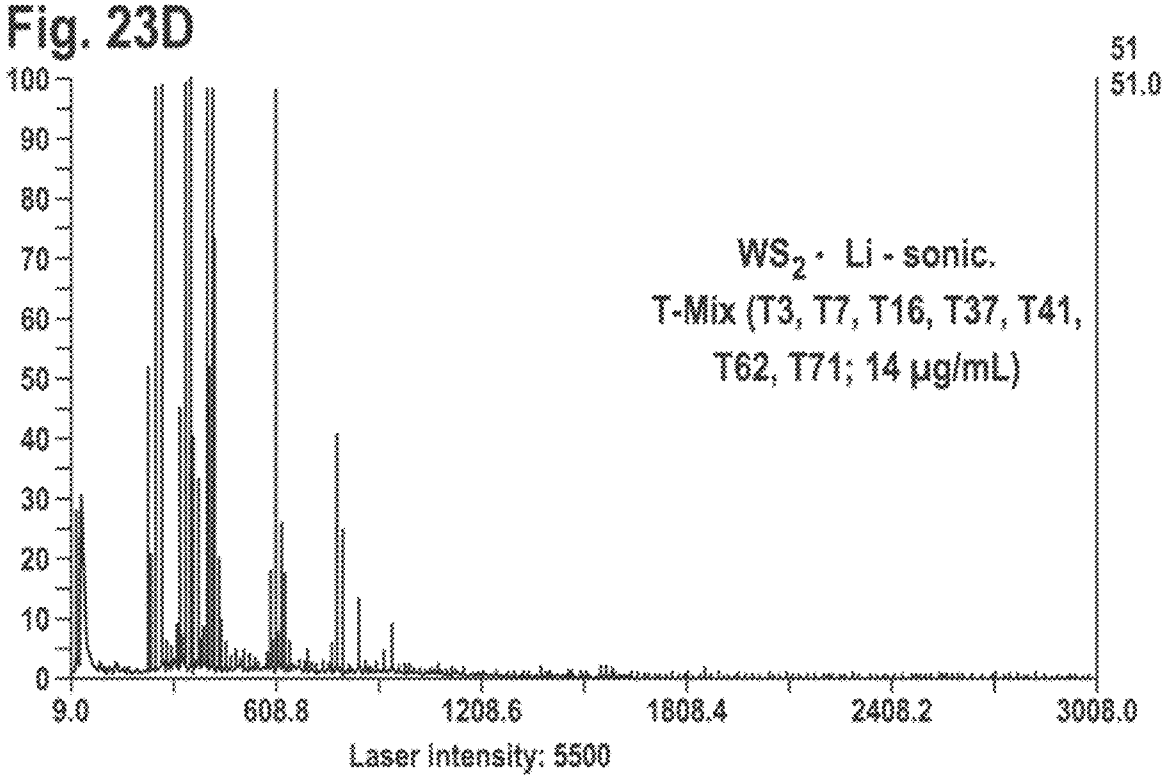

FIG. 23C and FIG. 23D show the relative intensity or absolute intensity as a function of the m/z of a steroid mixture comprising seven steroids: Te, Pr, Es, S7, S9, S10 and S19, each 14 μg/ml, and a mixture of seven therapeutically substances: T3, T7, T16, T37, T41, T62 and T71, each 14 μg/ml, respectively. The mixture of analytes is prepared on a $WS_2$ Li intercalated matrix (sonicated and centrifuged). At least no desorption or ionization of analytes is detectable.

Graphene/Graphene Oxide (State of the Art):

To compare the herein described materials applying as matrix for LDI-MS with literature known graphene based compounds (Wang et al., Anal. Chem. 2010, 82, 6208-6214; Min et al., Chem. Eur. J. 2015, 21, 7217-7223), commercial available graphene nanoplatelets (GR) as well as monolayer graphene oxide dispersion (GO) are evaluated. Therefore, a suspension of GR (5 mg/mL, MeCN/$H_2O$) is produced and the concentration of the GO dispersion is adjusted (1 mg/mL, $H_2O$/MeCN). After vigorously vortexing, both are used directly to coat the surface of a MALDI-steel-plate, applying the dried-droplet method (2×0.5 μL). Subsequently after analyte deposition and air-drying, MALDI-TOF measurements are performed in positive mode adjusting the laser intensity to a value of about 5500 units (GR) or 5000 units (GO) with a total of 2000 laser shots per spot. Analyte signals occurred as alkali adducts ($[M+Na]^+$ and $[M+K]^+$), whereat GR shows a lower desorption/ionization of analytes compared to $MoS_2$/$WS_2$/$TiS_2$/$SnS_2$, while GO results in significant occurrence of background signals itself.

Figure 24A:
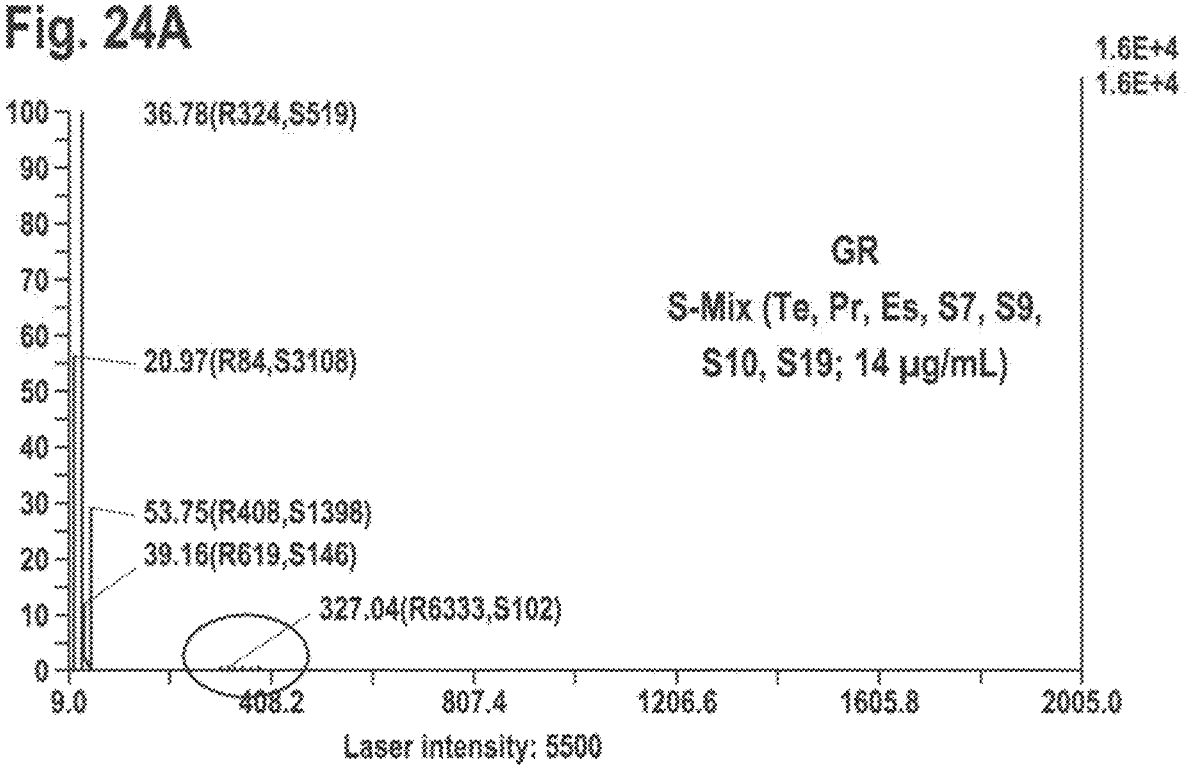
FIG. 24A to FIG. 24D show the MS spectra of a steroid mixture and therapeutically substance mixture premixed prepared on graphene based compounds matrix, respectively.
Figure 24B:
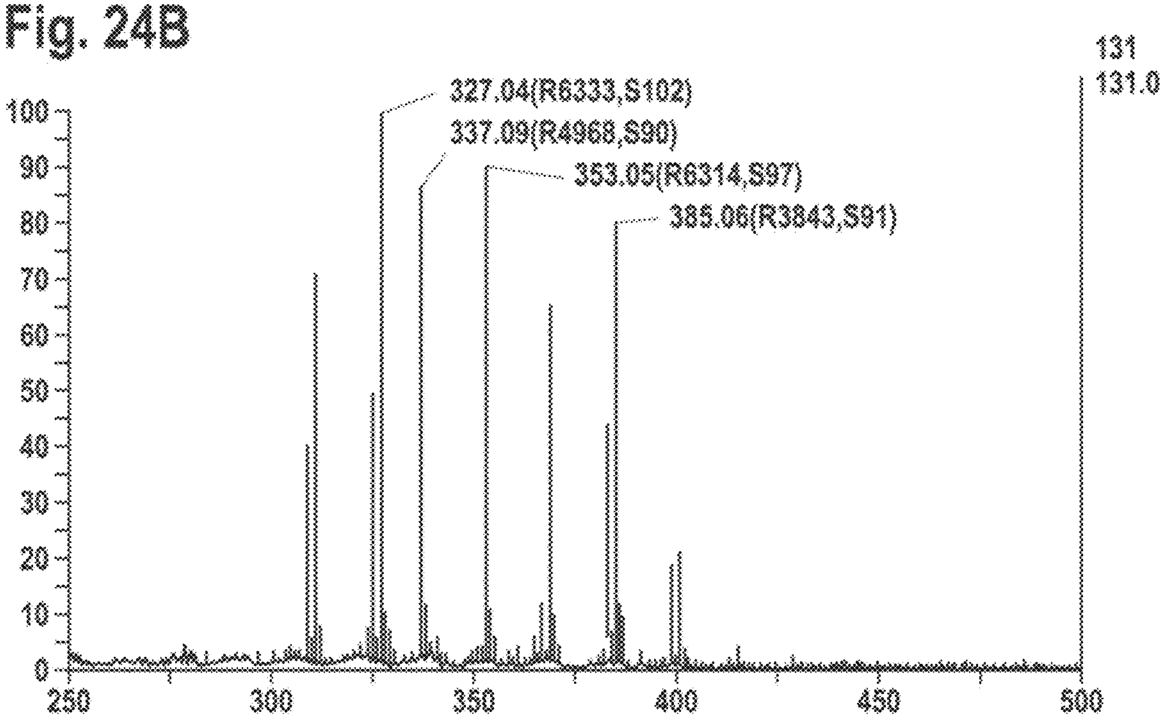

FIG. 24A and FIG. 24B show the relative intensity or absolute intensity as a function of the m/z of a steroid mixture comprising seven steroids: Te, Pr, Es, S7, S9, S10 and S19, each 14 μg/ml. The mixture of analytes is prepared on a graphene nanoplatelets (GR, size 25 μm, thickness 6 to 8 μm). In comparison to the herein described $MoS_2$-matrix, the analysis on graphene nanoplatelets showed just minor desorption/ionization of the tested steroid analytes.

Figure 24C:
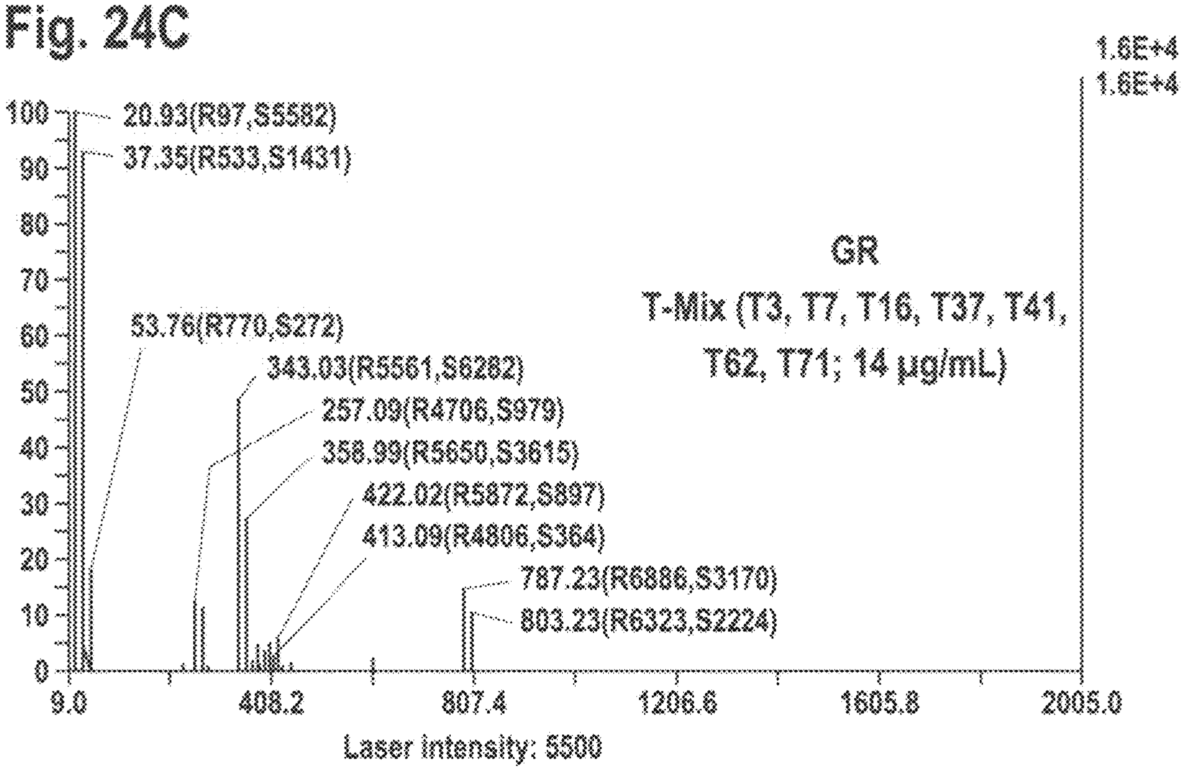
Figure 24D:
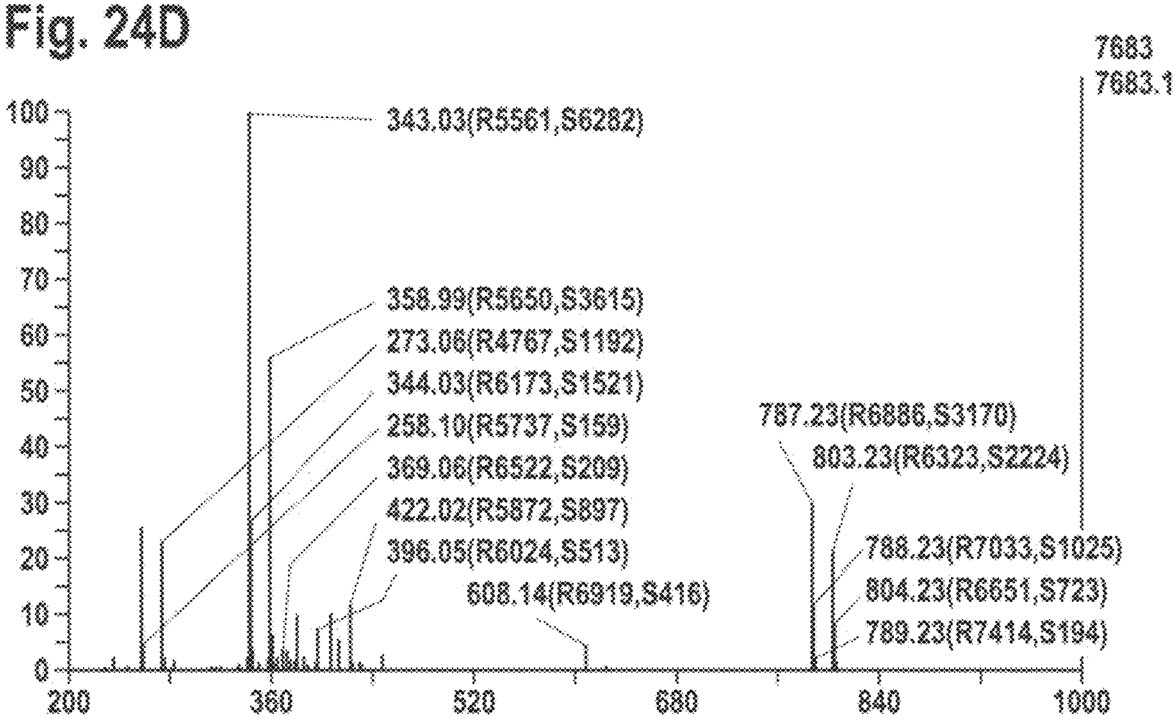

FIG. 24C and FIG. 24D show the relative intensity or absolute intensity as a function of the m/z of a mixture of seven therapeutically substances: T3, T7, T16, T37, T41, T62 and T71, each 14 μg/ml. The mixture of analytes is prepared on a graphene nanoplatelets (GR, size 25 μm, thickness 6 to 8 μm).

Figure 25A:
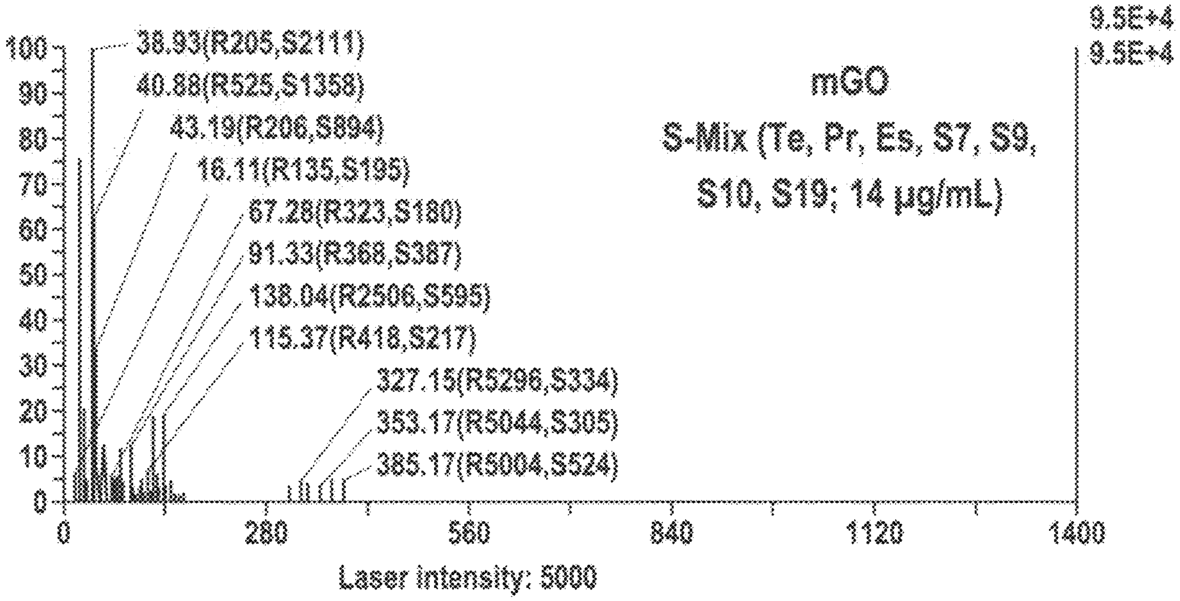
FIG. 25A to FIG. 25C show the MS spectra of a steroid mixture and therapeutically substance mixture premixed prepared on graphene based compounds matrix, respectively.
Figure 25B:
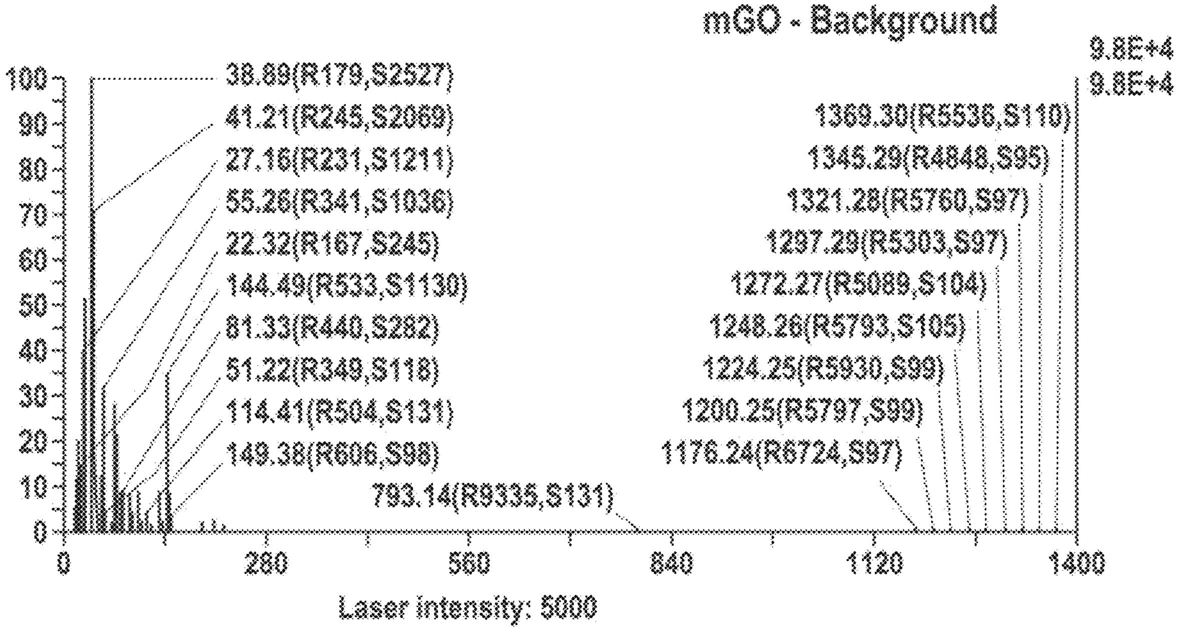
Figure 25C:
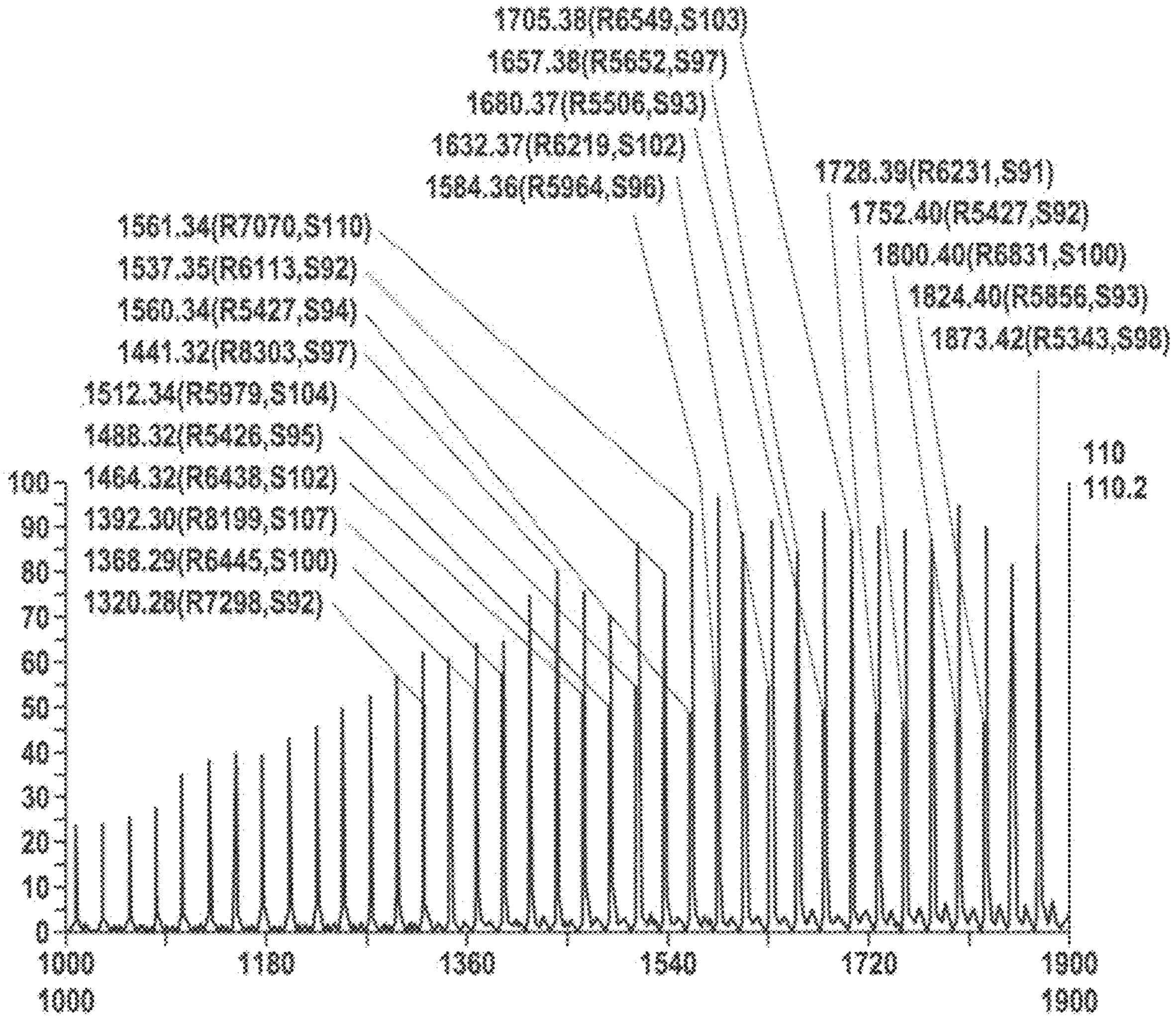

FIG. 25A shows the relative intensity or absolute intensity as a function of the m/z of a steroid mixture comprising seven steroids: Te, Pr, Es, S7, S9, S10 and S19, each 14 μg/ml. The mixture of analytes is prepared on a monolayer GO dispersion (mGO, FIG. 25B and FIG. 25C). FIG. 25C is an enlargement of the MS spectrum of FIG. 25A. In comparison to the herein described ($MoS_2$-)matrix, the analysis on a monolayer GO dispersion showed just minor desorption/ionization of the tested steroid analytes, while significant background can be observed especially in the range of m/z<150, with additional carbon derived fragments over a broad mass range (as can be seen in FIG. 25C). Further, the production of a well defined graphene compared to the matrix described herein is not satisfied.

Figure 26:
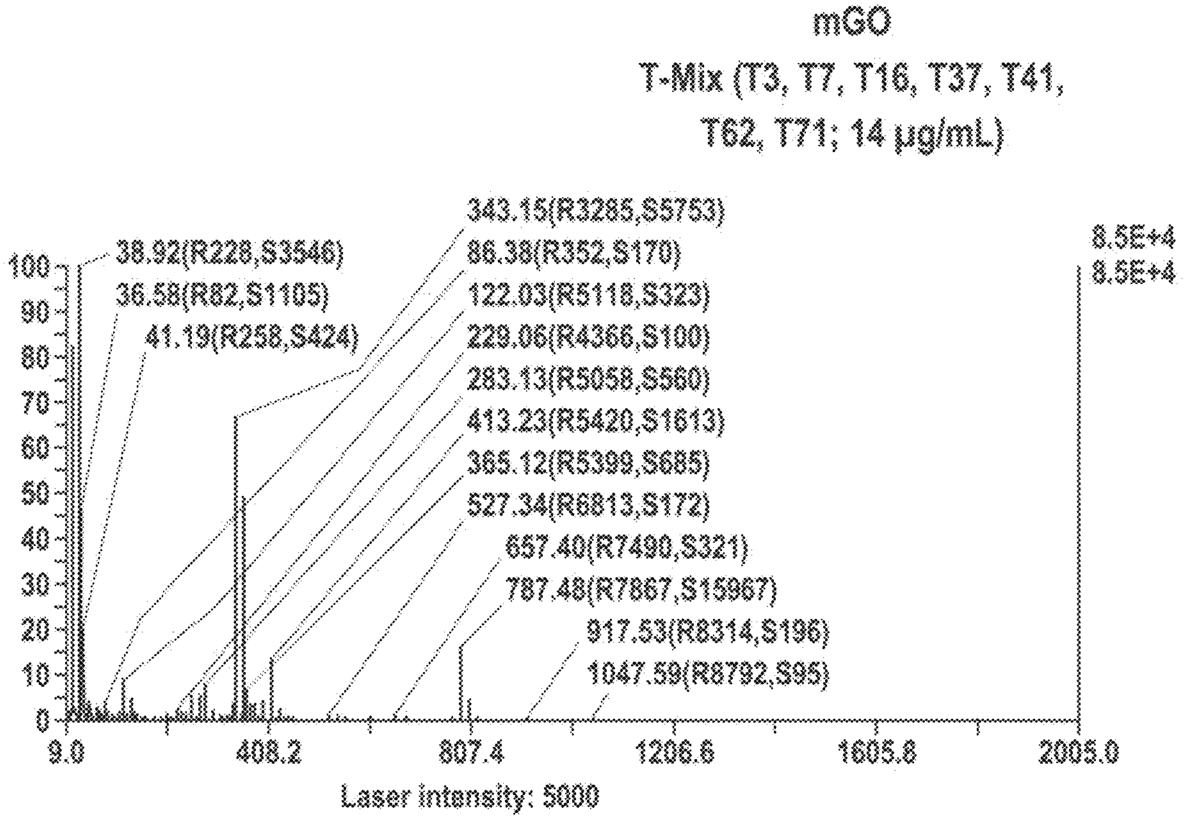
FIG. 26 shows the MS spectra of a steroid mixture and therapeutically substance mixture premixed prepared on graphene based compounds matrix, respectively.

FIG. 26 shows the relative intensity or absolute intensity as a function of the m/z of a mixture of seven therapeutically substances: T3, T7, T16, T37, T41, T62 and T71, each 14 μg/ml. The mixture of analytes is prepared on a monolayer GO dispersion (mGO). In comparison to the herein described $MoS_2$-matrix, the analysis on a monolayer GO dispersion showed just minor desorption/ionization of the tested therapeutic analytes, while significant background can be observed especially in the range of m/z<150.

Figure 27A:
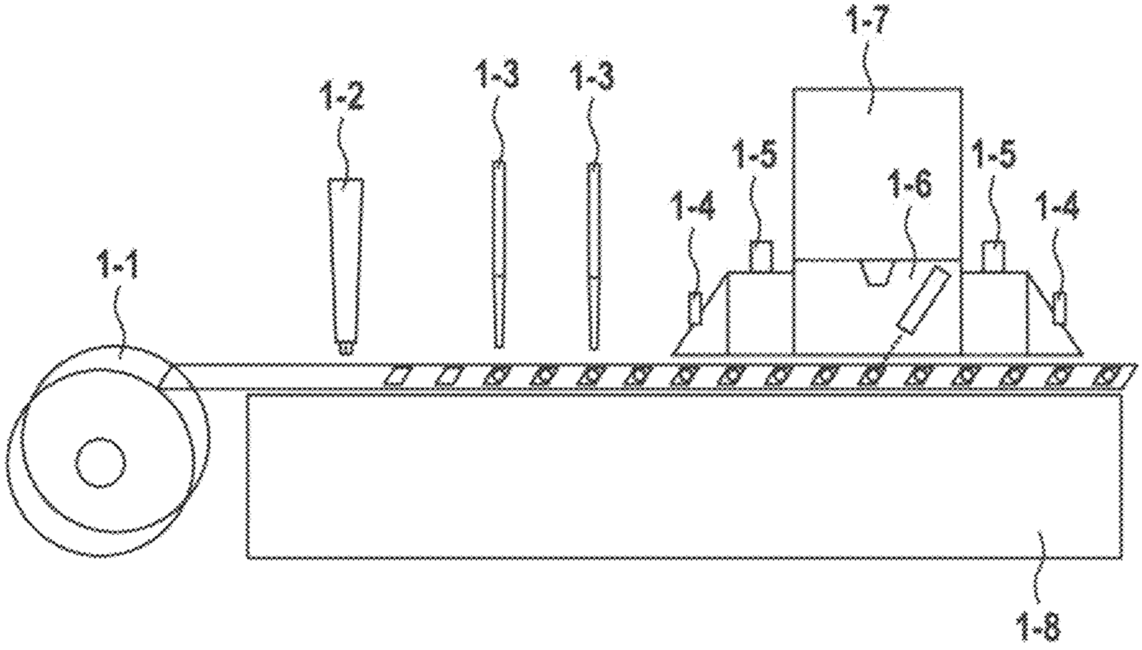
FIG. 27A and FIG. 27B show a continuous MALDI-system in combination with a structured sample surface.
Figure 27B:
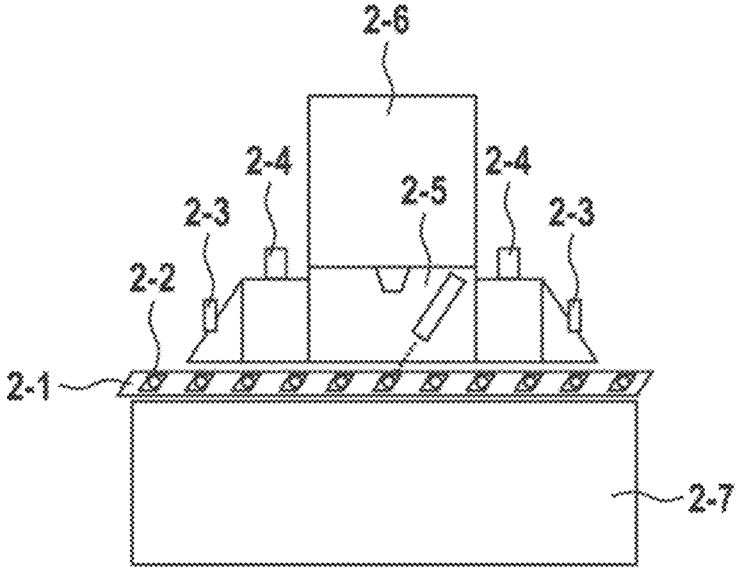

FIG. 27A and FIG. 27B show a continuous MALDI-system in combination with a structured sample surface.

FIG. 27A shows the preparation of the sample and the sample holder 1-1. In this case the sample holder 1-1 is a conductive material strip, e.g. made of copper. The sample holder 1-1 is structured. The structuring is a microstructuring. The microstructuring can comprise or, consist of several cavities, each in in the range of 100 μm to 1000 μm. The structuring is produced by a microstructuring stamp 1-2. The microstructuring stamp 1-2 stamps an adequate shape of the structuring into the sample holder 1-1. After structuring the sample holder 1-1, the sample holder 1-1 can be loaded with the sample 1-3 comprising the matrix and the at least one analyte of interest by using pipetting unit(s). The sample 1-3 is pipetted on the structured surface of a sample holder 1-1. The pipetting workflow can contain precoating with the herein described matrix as a suspension and the deposition of the analyte as a solution. For a continuous MALDI operation, a pass through vacuum system 1-4, 1-5, comprising or consisting of at least two vacuum zones (e.g. high and low vacuum) is preferred. The mass spectrometry unit 1-7 comprises a quadrupole with subsequent ion trapping, isobaric separation via ion mobility, fragmentation in a collision cell and is followed by quadrupole or time-of-flight (ToF) mass analysis (1-6—ultraviolet laser optics, 1-8—analysis module). Other techniques of ion manipulations, like magnetic sector, and different combinations of the corresponding units are also possible.

FIG. 27B shows a method for determining at least one analyte of interest. The prepared sample 2-2 comprising a matrix and the at least one analyte of interest is provided on a surface of a sample holder 2-1, in particular a conducting material strip, e.g. made of copper. Then, the sample 2-2 is ionized via laser irradiation having a wavelength of smaller than 400 nm. The laser irradiation is produced by ultraviolet laser optics 2-5. Then, the analyte of interest is determined using mass spectrometry 2-6 (2-3—vacuum chamber (low vacuum), 2-4—vacuum chamber (high vacuum), 2-7—analysis module).

Figure 28A:
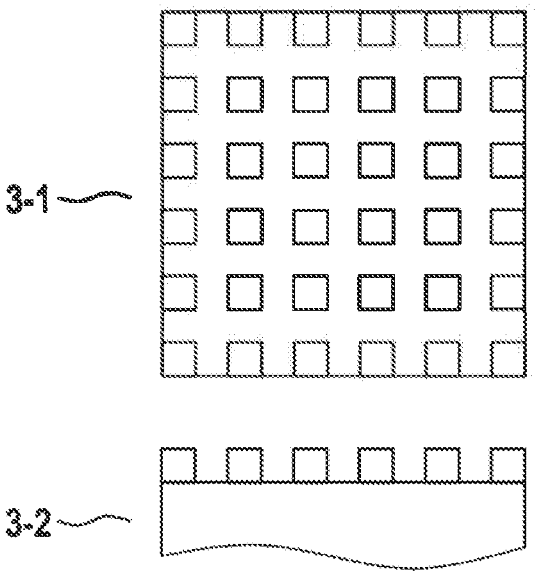
FIG. 28A and FIG. 28B show the microstructured cavities of the sample holder.
Figure 28B:
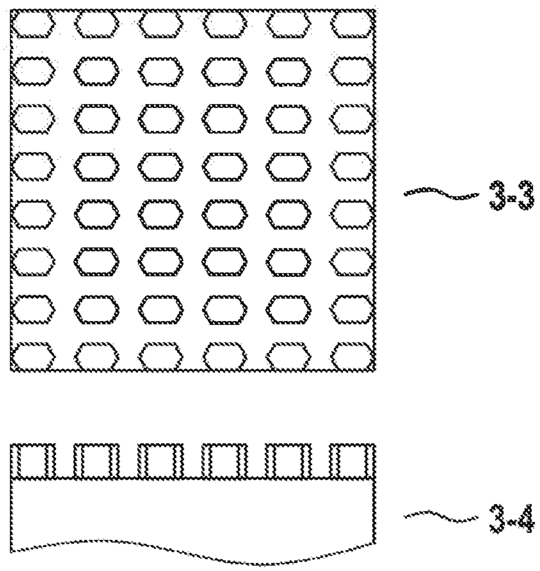

FIG. 28A and FIG. 28B show the top views (3-1 and 3-3) and side views (3-2 and 3-4) of the structured sample holder. The structured sample holder, e.g. a conductive material stripe, comprises microstructured cavities, which are produced by a microstructuring stamp. The uniformly shaped structures can be quadratic (3-1, 3-2) or hexagonal (3-3, 3-4) and can ensure a better distribution of the matrix as a suspension and the analyte as a solution on top of the cavities, without the presence of the commonly observed coffee-ring-effect. The coffee-ring-effect is known for a skilled person and thus is not explained in detail.

Figure 29:
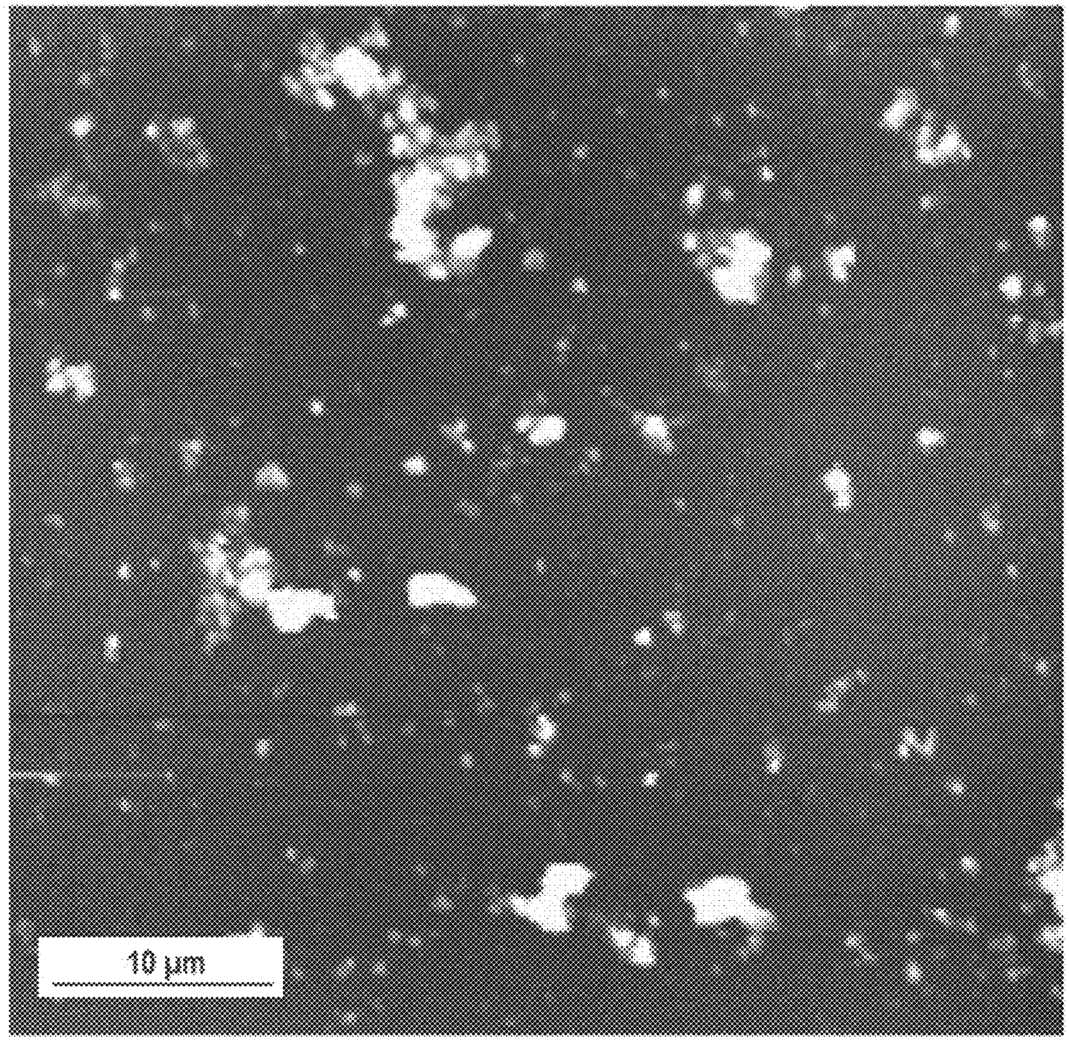
FIG. 29 shows an AFM (atomic force microscopy) image of a single layer of bulk $MoS_2$ matrix having a particle size of about 6 μm, which was sonicated.

FIG. 29 shows the AFM image of a single layer of bulk $MoS_2$ matrix having a initial particle size of about 6 μm, which was sonicated. The resulting particles have dimensions mainly in the range of 0.5 to 3 μm and the heights are observed mainly in the range of 20 to 300 nm with some smaller or larger particles also visible.

This patent application claims the priority of the European patent application 20190319.2, wherein the content of this European patent application is hereby incorporated by references.

The invention claimed is:

1. A method for determining at least one analyte of interest comprising the following steps:

a) preparing a sample comprising a matrix and the at least one analyte of interest on a surface of a sample holder, wherein the matrix comprises at least one transition metal disulfide, wherein the transition metal disulfide is formed as particles having a particle size in the range of 1 nm to 6 μm, wherein step a) comprises:

applying the sample in liquid form on the surface of a sample holder and drying the sample, wherein the applying comprises (i) a combined applying of the matrix and the analyte of interest, followed by drying, or (ii) a sequentially applying of the matrix and the analyte of interest, wherein in the case of the sequentially applying of the matrix and the analyte of interest, the drying is followed after each sequentially applying of the matrix and the analyte of interest, b) ionizing the at least one analyte of interest via laser irradiation having a wavelength of smaller than 400 nm, and c) determining the analyte of interest using mass spectrometry, wherein the method is free of silver nanoparticles, intercalated lithium, a lithium mediated exfoliation step, a sodium hydroxide assisted exfoliation step and a porous nanostructuring step.

2. The method of claim 1, wherein said method is capable of detecting alkali ions and/or earth-alkali ions by a direct ionization in step b), wherein the alkali ions and/or earth-alkali ions are selected from the group consisting of $Na^+$, $K^+$, $Rb^+$, $Cs^+$, $Mg^{2+}$, $Ca^{2+}$, $Sr^{2+}$, and $Ba^{2+}$.

3. The method of claim 1, wherein before step a) a further step al) is carried out:

a1) sonication of the matrix.

4. The method of claim 1, wherein the surface is an electrically conductive surface, wherein the electrically conductive surface is structured.

5. The method of claim 1, wherein the analyte of interest has a molecular weight of smaller than 2000 Da.

6. The method of claim 1, wherein the analyte of interest is selected from the group consisting of a nucleic acid, an amino acid, a peptide, a protein, a metabolite, hormones, a fatty acid, a lipid, a carbohydrate, a steroid, a ketosteroid, a secosteroid, a molecule characteristic of a certain modification of another molecule, a substance that has been internalized by the organism, and a metabolite of such a substance, and combinations thereof.

7. The method of claim 1, wherein the transition metal disulfide is selected from the group consisting of MoS2, TiS2, and combinations thereof.

8. The method of claim 1, wherein in step a) the particles of the transition metal disulfide have a particle size in the range of 80 nm to 150 nm.

* * * * *